(12) United States Patent
Auld et al.

(10) Patent No.: US 11,224,537 B2
(45) Date of Patent: Jan. 18, 2022

(54) INTRAOCULAR GAS INJECTOR

(71) Applicant: Alcon Inc., Fribourg (CH)

(72) Inventors: Jack Robert Auld, Laguna Niguel, CA (US); John Christopher Huculak, Mission Viejo, CA (US); James Lescoulie, Costa Mesa, CA (US); Christopher McCollam, Fountain Valley, CA (US); Marcus Antonio Souza, Costa Mesa, CA (US)

(73) Assignee: Alcon Inc., Fribourg (CH)

( * ) Notice: Subject to any disclaimer, the term of this patent is extended or adjusted under 35 U.S.C. 154(b) by 217 days.

(21) Appl. No.: 16/165,140

(22) Filed: Oct. 19, 2018

(65) Prior Publication Data

US 2020/0121499 A1 Apr. 23, 2020

(51) Int. Cl.
| | | |
|---|---|---|
| *A61F 9/007* | (2006.01) | |
| *A61D 1/00* | (2006.01) | |
| *A61M 5/31* | (2006.01) | |
| *A61M 5/315* | (2006.01) | |

(Continued)

(52) U.S. Cl.
CPC .............. *A61F 9/007* (2013.01); *A61D 1/00* (2013.01); *A61M 5/3145* (2013.01); *A61M 5/31596* (2013.01); *A61D 7/00* (2013.01); *A61M 5/145* (2013.01); *A61M 5/3158* (2013.01); *A61M 2005/3128* (2013.01); *A61M 2202/02* (2013.01); *A61M 2210/0612* (2013.01)

(58) Field of Classification Search
CPC ... A61F 9/007; A61F 9/00727; A61M 5/3145; A61M 5/31596; A61M 5/145; A61M 2005/3128; A61M 5/31553; A61M 5/3158; A61M 5/165; A61M 5/16804; A61M 5/30; A61M 5/3007; A61M 2210/0612; A61M 2202/02; A61M 2005/1657; A61M 2205/75; A61M 11/003; A61M 11/007; A61B 17/3203; A61B 2017/32035; A61D 1/00; A61D 7/00

See application file for complete search history.

(56) References Cited

U.S. PATENT DOCUMENTS

| | | |
|---|---|---|
| 3,004,686 A | 10/1961 | Mckee |
| 3,341,082 A | 9/1967 | Meshberg |
| 3,481,323 A | 12/1969 | Cook et al. |

(Continued)

FOREIGN PATENT DOCUMENTS

| | | |
|---|---|---|
| DE | 2543284 A1 | 3/1977 |
| JP | 2004-049726 A | 2/2004 |

(Continued)

OTHER PUBLICATIONS

Chinese Office Action in Application 201380024227.9 dated Aug. 5, 2016 in 6 pages, (partial translation).

(Continued)

*Primary Examiner* — Amber R Stiles
*Assistant Examiner* — Alexandra Lalonde

(57) ABSTRACT

A gas mixture apparatus includes a measurement control system, an activation system, a pressurized chamber with one or more gases, and a mixing chamber. A filter can be preattached to the outlet of the mixture apparatus, allowing (Continued)

excess gas to be discharged therethrough and then atmospheric air to be drawn into the mixture apparatus through the filter for creating a therapeutic gas mixture.

20 Claims, 31 Drawing Sheets

(51) Int. Cl.
*A61D 7/00* (2006.01)
*A61M 5/145* (2006.01)

(56) References Cited

U.S. PATENT DOCUMENTS

| | | | |
|---|---|---|---|
| 3,537,622 A | 11/1970 | Baker et al. |
| 3,853,157 A | 12/1974 | Madaio |
| 4,429,421 A | 2/1984 | Levy |
| 4,490,351 A | 12/1984 | Clark |
| 4,498,904 A | 2/1985 | Turner et al. |
| 4,573,998 A | 3/1986 | Mazzocco |
| 4,615,703 A | 10/1986 | Callahan et al. |
| 4,619,256 A | 10/1986 | Horn |
| 4,634,423 A | 1/1987 | Bailey, Jr. |
| 4,670,006 A | 6/1987 | Sinnett et al. |
| 4,699,140 A | 10/1987 | Holmes et al. |
| 4,715,373 A | 12/1987 | Mazzocco et al. |
| 4,717,384 A | 1/1988 | Waldeisen |
| 4,726,367 A | 2/1988 | Shoemaker |
| 4,747,404 A | 5/1988 | Jampel et al. |
| 4,760,865 A | 8/1988 | Rilett |
| 4,763,650 A | 8/1988 | Hauser |
| 4,765,329 A | 8/1988 | Cumming et al. |
| 4,822,360 A | 4/1989 | Deacon |
| 4,844,065 A | 7/1989 | Faulkner |
| 4,844,093 A | 7/1989 | Jampel et al. |
| 4,852,566 A | 8/1989 | Callahan et al. |
| 4,862,885 A | 9/1989 | Cumming |
| 4,880,000 A | 11/1989 | Holmes et al. |
| 4,906,247 A | 3/1990 | Fritch |
| 4,919,130 A | 4/1990 | Stoy et al. |
| 4,934,363 A | 6/1990 | Smith et al. |
| 5,007,913 A | 4/1991 | Dulebohn et al. |
| 5,019,037 A | 5/1991 | Wang |
| 5,032,111 A | 7/1991 | Morris et al. |
| 5,037,384 A | 8/1991 | Chang |
| 5,047,009 A | 9/1991 | Morris et al. |
| 5,064,413 A | 11/1991 | McKinnon et al. |
| 5,066,276 A | 11/1991 | Wang |
| 5,066,297 A | 11/1991 | Cumming |
| 5,098,439 A | 3/1992 | Hill et al. |
| 5,123,905 A | 6/1992 | Kelman |
| 5,222,972 A | 1/1993 | Hill et al. |
| 5,190,552 A | 3/1993 | Kelman |
| 5,304,182 A | 4/1994 | Rheinish et al. |
| 5,329,975 A | 7/1994 | Heitel |
| 5,334,163 A | 8/1994 | Sinnett |
| 5,336,175 A | 8/1994 | Mames |
| 5,354,333 A | 10/1994 | Kammann et al. |
| 5,487,725 A | 1/1996 | Peyman |
| 5,496,328 A | 3/1996 | Nakajima et al. |
| 5,547,473 A | 8/1996 | Peyman |
| 5,562,676 A | 10/1996 | Brady et al. |
| 5,582,613 A | 12/1996 | Brady et al. |
| 5,582,614 A | 12/1996 | Feingold |
| 5,616,148 A | 4/1997 | Eagles et al. |
| 5,620,422 A | 4/1997 | Halbich |
| 5,630,821 A | 5/1997 | Klaas |
| 5,643,275 A | 7/1997 | Blake |
| 5,643,276 A | 7/1997 | Zaleski |
| 5,676,888 A | 10/1997 | Kuckens et al. |
| 5,693,057 A | 12/1997 | Dusek |
| 5,716,364 A | 2/1998 | Makker et al. |
| 5,772,666 A | 6/1998 | Feingold et al. |
| 5,772,667 A | 6/1998 | Blake |
| 5,776,138 A | 7/1998 | Vidal et al. |
| 5,803,925 A | 9/1998 | Yang et al. |
| 5,807,400 A | 9/1998 | Chambers et al. |
| 5,810,833 A | 9/1998 | Brady et al. |
| 5,860,984 A | 1/1999 | Chambers et al. |
| 5,868,751 A | 2/1999 | Feingold |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,921,989 A | 7/1999 | Deacon et al. |
| 5,944,725 A | 8/1999 | Cicenas et al. |
| 5,947,975 A | 9/1999 | Kikuchi et al. |
| 5,947,976 A | 9/1999 | Van Noy et al. |
| 5,997,498 A | 12/1999 | De Juan, Jr. |
| 6,024,719 A | 2/2000 | Morris |
| 6,050,957 A | 4/2000 | Desch |
| 6,073,759 A | 6/2000 | Lamborne et al. |
| 6,159,161 A | 12/2000 | Hodosh |
| 6,254,575 B1 | 7/2001 | Thorne |
| 6,299,618 B1 | 10/2001 | Sugiura |
| 6,312,433 B1 | 11/2001 | Butts et al. |
| 6,334,862 B1 | 1/2002 | Vidal et al. |
| 6,336,932 B1 | 1/2002 | Figueroa et al. |
| 6,342,058 B1 | 1/2002 | Portney |
| 6,371,960 B2 | 4/2002 | Heyman et al. |
| 6,387,101 B1 | 5/2002 | Butts et al. |
| 6,398,789 B1 | 6/2002 | Capetan |
| 6,428,545 B2 | 8/2002 | Portney |
| 6,439,276 B1 | 8/2002 | Wood |
| 6,468,282 B2 | 10/2002 | Kikuchi et al. |
| 6,491,697 B1 | 12/2002 | Clark et al. |
| 6,494,314 B1 | 12/2002 | Lamborne et al. |
| 6,500,181 B1 | 12/2002 | Portney |
| 6,503,275 B1 | 1/2003 | Cumming |
| 6,506,176 B1 | 1/2003 | Mittelstein et al. |
| 6,506,195 B2 | 1/2003 | Chambers et al. |
| 6,533,769 B2 | 3/2003 | Holmén |
| 6,537,281 B1 | 3/2003 | Portney |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,582,445 B1 | 6/2003 | Koons |
| 6,585,972 B2 | 7/2003 | Peyman |
| 6,599,271 B1 | 7/2003 | Easley |
| 6,599,280 B1 | 7/2003 | Pynson et al. |
| 6,601,609 B2 | 8/2003 | Taylor |
| 6,607,537 B1 | 8/2003 | Binder |
| 6,629,979 B1 | 10/2003 | Feingold et al. |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,726,666 B2 | 4/2004 | De Juan, Jr. |
| 6,733,507 B2 | 5/2004 | McNicholas et al. |
| 6,858,033 B2 | 2/2005 | Kobayashi |
| 6,866,142 B2 | 3/2005 | Lamborne et al. |
| 6,899,877 B2 | 5/2005 | Peyman |
| 6,921,405 B2 | 7/2005 | Feingold et al. |
| 6,923,815 B2 | 8/2005 | Brady et al. |
| 6,976,989 B1 | 12/2005 | Vincent |
| 6,981,612 B2 | 1/2006 | Siimes et al. |
| 6,986,763 B2 | 1/2006 | Holmén |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,037,328 B2 | 5/2006 | Vincent |
| 7,131,976 B2 | 11/2006 | Kobayashi et al. |
| 7,137,994 B2 | 11/2006 | De Juan, Jr. et al. |
| 7,156,855 B2 | 1/2007 | Oda |
| 7,276,071 B2 | 10/2007 | Lin et al. |
| 7,279,006 B2 | 10/2007 | Vincent |
| 7,316,676 B2 | 1/2008 | Peyman et al. |
| 7,328,700 B2 | 2/2008 | Baker et al. |
| 7,335,209 B2 | 2/2008 | Meyer |
| RE40,185 E | 3/2008 | Kikuchi et al. |
| 7,348,038 B2 | 3/2008 | Makker et al. |
| 7,422,604 B2 | 9/2008 | Vaquero et al. |

(56) References Cited

U.S. PATENT DOCUMENTS

| | | |
|---|---|---|
| 7,429,263 B2 | 9/2008 | Vaquero et al. |
| 7,458,976 B2 | 12/2008 | Peterson et al. |
| 7,476,229 B2 | 1/2009 | Meyer |
| 7,476,230 B2 | 1/2009 | Ohno et al. |
| 7,585,291 B1 | 9/2009 | Campion |
| 7,645,300 B2 | 1/2010 | Tsai |
| 7,687,097 B2 | 3/2010 | Makker et al. |
| 7,704,258 B2 | 4/2010 | Feingold et al. |
| 7,740,636 B2 | 6/2010 | Lee et al. |
| 7,744,580 B2 | 6/2010 | Reboul |
| 7,744,603 B2 | 6/2010 | Zadno-Azizi et al. |
| 7,867,240 B2 | 1/2011 | Peterson et al. |
| 7,883,496 B2 | 2/2011 | Campion |
| 7,892,202 B2 | 2/2011 | Lampropoulos et al. |
| 7,892,283 B2 | 2/2011 | Shepherd |
| 7,901,414 B2 | 3/2011 | Tourrette et al. |
| 7,947,049 B2 | 5/2011 | Vaquero |
| 7,988,701 B2 | 8/2011 | Vaquero et al. |
| 8,021,423 B2 | 9/2011 | Tanaka |
| 8,048,085 B2 | 11/2011 | Peterson et al. |
| 8,062,360 B2 | 11/2011 | Pollock |
| 8,080,017 B2 | 12/2011 | Tanaka |
| 8,114,095 B2 | 2/2012 | Rathert |
| 8,123,804 B2 | 2/2012 | Tanaka |
| 8,142,498 B2 | 3/2012 | Tsai |
| 8,152,817 B2 | 4/2012 | Tanaka |
| 8,216,629 B2 | 7/2012 | Mentak |
| 8,246,631 B2 | 8/2012 | Pynson |
| 8,252,053 B2 | 8/2012 | Pynson |
| 8,308,700 B2 | 11/2012 | Campion |
| 8,308,736 B2 | 11/2012 | Boukhny et al. |
| 8,308,799 B2 | 11/2012 | Chen et al. |
| 8,353,314 B2 | 2/2013 | Radford et al. |
| 8,568,367 B2 | 10/2013 | Griffiths et al. |
| 8,986,242 B2 | 3/2015 | Auld et al. |
| 9,693,895 B2 | 7/2017 | Auld et al. |
| 9,764,088 B2 | 9/2017 | Huculak |
| 10,434,010 B2 | 10/2019 | Auld |
| 2001/0007942 A1 | 7/2001 | Kikuchi et al. |
| 2002/0189705 A1 | 12/2002 | Reihl |
| 2002/0193803 A1 | 12/2002 | Portney |
| 2003/0187455 A1 | 10/2003 | Kobayashi et al. |
| 2003/0209455 A1 | 11/2003 | Pynson et al. |
| 2003/0212406 A1 | 11/2003 | Kobayashi et al. |
| 2003/0212407 A1 | 11/2003 | Kikuchi et al. |
| 2003/0216745 A1 | 11/2003 | Brady et al. |
| 2004/0035491 A1 | 2/2004 | Castellano |
| 2004/0059343 A1 | 3/2004 | Shearer et al. |
| 2004/0127911 A1 | 7/2004 | Figueroa et al. |
| 2004/0215207 A1 | 10/2004 | Cumming |
| 2004/0267359 A1 | 12/2004 | Makker et al. |
| 2005/0033308 A1 | 2/2005 | Callahan et al. |
| 2005/0171555 A1 | 8/2005 | Tran et al. |
| 2005/0222577 A1 | 10/2005 | Vaquero |
| 2005/0267403 A1 | 12/2005 | Landau et al. |
| 2005/0267486 A1 | 12/2005 | Holmen |
| 2005/0283162 A1 | 12/2005 | Stratas |
| 2005/0283163 A1 | 12/2005 | Portney et al. |
| 2005/0283164 A1 | 12/2005 | Wu et al. |
| 2006/0085013 A1 | 4/2006 | Dusek et al. |
| 2006/0089594 A1 | 4/2006 | Landau |
| 2006/0111667 A1 | 5/2006 | Matsuura |
| 2006/0142780 A1 | 6/2006 | Pynson et al. |
| 2006/0142781 A1 | 6/2006 | Pynson et al. |
| 2006/0167466 A1 | 7/2006 | Dusek |
| 2006/0184181 A1 | 8/2006 | Cole et al. |
| 2006/0264971 A1 | 11/2006 | Akahoshi |
| 2006/0271063 A1 | 11/2006 | Sunada et al. |
| 2006/0287655 A1 | 12/2006 | Khuray et al. |
| 2006/0293694 A1 | 12/2006 | Futamura |
| 2007/0060925 A1 | 3/2007 | Pynson |
| 2007/0203502 A1 | 8/2007 | Makker et al. |
| 2007/0265574 A1 | 11/2007 | Tennican et al. |
| 2007/0270881 A1 | 11/2007 | Hishinuma et al. |
| 2007/0270945 A1 | 11/2007 | Kobayashi et al. |
| 2008/0027460 A1 | 1/2008 | Kobayashi |
| 2008/0027461 A1 | 1/2008 | Vaquero et al. |
| 2008/0033449 A1 | 2/2008 | Cole et al. |
| 2008/0039862 A1 | 2/2008 | Tran |
| 2008/0058830 A1 | 3/2008 | Cole et al. |
| 2008/0082078 A1 | 4/2008 | Berlin |
| 2008/0086146 A1 | 4/2008 | Ishii et al. |
| 2008/0097379 A1 | 4/2008 | Dacquay et al. |
| 2008/0097459 A1 | 4/2008 | Kammerlander et al. |
| 2008/0097460 A1 | 4/2008 | Boukhny et al. |
| 2008/0097461 A1 | 4/2008 | Boukhny et al. |
| 2008/0103432 A1 | 5/2008 | Sanchez et al. |
| 2008/0103433 A1 | 5/2008 | Nazarifar et al. |
| 2008/0147080 A1 | 6/2008 | Pynson |
| 2008/0147081 A1 | 6/2008 | Pynson |
| 2008/0147082 A1 | 6/2008 | Pynson |
| 2008/0154361 A1 | 6/2008 | Pynson et al. |
| 2008/0173835 A1 | 7/2008 | Tomassetti |
| 2008/0208110 A1 | 8/2008 | Sanchez |
| 2008/0208114 A1 | 8/2008 | Landau |
| 2008/0208176 A1 | 8/2008 | Loh |
| 2008/0255579 A1 | 10/2008 | Wollenhaupt et al. |
| 2008/0269770 A1 | 10/2008 | Pynson et al. |
| 2009/0005788 A1 | 1/2009 | Rathert |
| 2009/0018548 A1 | 1/2009 | Charles |
| 2009/0024136 A1 | 1/2009 | Martin et al. |
| 2009/0030425 A1 | 1/2009 | Smiley et al. |
| 2009/0036898 A1 | 2/2009 | Ichinohe et al. |
| 2009/0036900 A1 | 2/2009 | Moll |
| 2009/0043313 A1 | 2/2009 | Ichinohe et al. |
| 2009/0112222 A1 | 4/2009 | Barrows et al. |
| 2009/0118680 A1 | 5/2009 | Goldbrunner et al. |
| 2009/0198247 A1 | 8/2009 | Ben Nun |
| 2009/0204122 A1 | 8/2009 | Ichinohe et al. |
| 2009/0234366 A1 | 9/2009 | Tsai et al. |
| 2009/0248031 A1 | 10/2009 | Ichinohe et al. |
| 2009/0254023 A1 | 10/2009 | Akduman |
| 2009/0270876 A1 | 10/2009 | Hoffmann et al. |
| 2009/0292293 A1 | 11/2009 | Bogaert et al. |
| 2009/0318933 A1 | 12/2009 | Anderson |
| 2010/0010498 A1 | 1/2010 | Biddle et al. |
| 2010/0042071 A1 | 2/2010 | Reynolds |
| 2010/0057095 A1 | 3/2010 | Khuray et al. |
| 2010/0076450 A1 | 3/2010 | Yoshida et al. |
| 2010/0082037 A1 | 4/2010 | Kobayashi et al. |
| 2010/0087776 A1 | 4/2010 | Warren |
| 2010/0087832 A1 | 4/2010 | Seyboth |
| 2010/0106160 A1 | 4/2010 | Tsai |
| 2010/0121340 A1 | 5/2010 | Downer |
| 2010/0125278 A1 | 5/2010 | Wagner |
| 2010/0125279 A1 | 5/2010 | Karakelle et al. |
| 2010/0160926 A1 | 6/2010 | Artsyukhovich et al. |
| 2010/0161049 A1 | 6/2010 | Inoue |
| 2010/0185206 A1 | 7/2010 | Ichinohe et al. |
| 2010/0193050 A1 | 8/2010 | Job |
| 2010/0204704 A1 | 8/2010 | Davies et al. |
| 2010/0204705 A1 | 8/2010 | Brown et al. |
| 2010/0217273 A1 | 8/2010 | Someya et al. |
| 2010/0217274 A1 | 8/2010 | Lee et al. |
| 2010/0228260 A1 | 9/2010 | Callahan et al. |
| 2010/0228261 A1 | 9/2010 | Feingold et al. |
| 2010/0256651 A1 | 10/2010 | Jani et al. |
| 2010/0280521 A1 | 11/2010 | Vaquero et al. |
| 2010/0286704 A1 | 11/2010 | Ichinohe et al. |
| 2010/0305577 A1 | 12/2010 | Muchhala et al. |
| 2010/0312254 A1 | 12/2010 | Downer et al. |
| 2011/0046546 A1 | 2/2011 | Rasor et al. |
| 2011/0046633 A1 | 2/2011 | Pankin et al. |
| 2011/0046634 A1 | 2/2011 | Rathert |
| 2011/0046635 A1 | 2/2011 | Pankin et al. |
| 2011/0082463 A1 | 4/2011 | Inoue |
| 2011/0098717 A1 | 4/2011 | Inoue |
| 2011/0144653 A1 | 6/2011 | Pankin et al. |
| 2011/0152872 A1 | 6/2011 | Seyboth et al. |
| 2011/0152873 A1 | 6/2011 | Shepherd |
| 2011/0172676 A1 | 7/2011 | Chen |
| 2011/0190777 A1 | 8/2011 | Hohl |
| 2011/0196232 A1 | 8/2011 | Kim et al. |
| 2011/0213380 A1 | 9/2011 | Han |

(56) References Cited

U.S. PATENT DOCUMENTS

| | | |
|---|---|---|
| 2011/0224677 A1 | 9/2011 | Niwa et al. |
| 2011/0245840 A1 | 10/2011 | Seyboth et al. |
| 2011/0264101 A1 | 10/2011 | Inoue et al. |
| 2011/0270264 A1 | 11/2011 | Shoji et al. |
| 2011/0282273 A1 | 11/2011 | Evans et al. |
| 2011/0288557 A1 | 11/2011 | Kudo et al. |
| 2011/0295264 A1 | 12/2011 | Cole et al. |
| 2011/0313425 A1 | 12/2011 | Han |
| 2012/0016374 A1 | 1/2012 | Han |
| 2012/0016375 A1 | 1/2012 | Peterson et al. |
| 2012/0022547 A1 | 1/2012 | Hildebrand et al. |
| 2012/0022548 A1 | 1/2012 | Zacharias |
| 2012/0071888 A1 | 3/2012 | Putallaz et al. |
| 2012/0130390 A1 | 5/2012 | Davies et al. |
| 2012/0158007 A1 | 6/2012 | Brown et al. |
| 2012/0165824 A1 | 6/2012 | Tsai |
| 2012/0245530 A1 | 9/2012 | Oden |
| 2012/0245591 A1 | 9/2012 | Matthews |
| 2012/0253332 A1 | 10/2012 | Moll |
| 2012/0253356 A1 | 10/2012 | Niwa et al. |
| 2012/0289969 A1 | 11/2012 | Seyboth et al. |
| 2012/0289970 A1 | 11/2012 | Pynson |
| 2012/0323173 A1 | 12/2012 | Thorne, Jr. et al. |
| 2013/0012956 A1 | 1/2013 | Mirlay |
| 2013/0041382 A1 | 2/2013 | Ben Nun |
| 2013/0090603 A1 | 4/2013 | Hoyle, Jr. |
| 2013/0204130 A1 | 8/2013 | Mcarthur |
| 2013/0264266 A1* | 10/2013 | Shick .................. B01D 63/087 210/236 |
| 2013/0345619 A1* | 12/2013 | Auld ................ A61M 5/31553 604/24 |
| 2015/0314070 A1 | 11/2015 | Heintz |
| 2017/0325995 A1 | 11/2017 | Auld |
| 2019/0269850 A1* | 9/2019 | Shih ...................... A61F 9/0017 |
| 2020/0330687 A1* | 10/2020 | Maas ................ A61M 5/31511 |

FOREIGN PATENT DOCUMENTS

| | | |
|---|---|---|
| JP | 2005506139 A | 3/2005 |
| JP | 2010508074 | 3/2010 |
| RU | 2369368 C1 | 10/2009 |
| WO | WO 2003/033363 A1 | 4/2003 |
| WO | WO 2008/057672 A2 | 4/2003 |
| WO | WO 2005/102421 A1 | 11/2005 |
| WO | WO2005115529 A2 | 12/2005 |
| WO | WO 2007/098622 A1 | 9/2007 |
| WO | WO 2007/112130 A2 | 10/2007 |
| WO | WO 2010/028873 A1 | 3/2010 |
| WO | WO 2012/012127 A2 | 1/2012 |
| WO | 2012118762 A1 | 9/2012 |
| WO | 2015009746 A2 | 4/2015 |

OTHER PUBLICATIONS

International Search Report and Written Opinion in Application No. PCT/US2013/044183 dated Nov. 4, 2013 in 12 pages.
International Search Report and Written Opinion in Application No. PCT/US2013/045515 dated Sep. 5, 2013 in 19 pages.
International Preliminary Report on Patentability in Application No. PCT/US2013/045515 dated Dec. 2014 in 17 pages.
New Zealand Office Action in Application 702909 dated Jan. 22, 2016 in 6 pages.
Notice of Reasons for Refusal for Japanese Application 2015/157407 dated Apr. 11, 2017 in 6 pages (partial translation).
Office Action in Russian Application 2014053240 dated Nov. 28, 2017 in 2 pages, (partial translation).
Supplementary European Search Report in Application 13803578.7 dated Jan. 19, 2016 in 2 pages.

* cited by examiner

INTRAOCULAR GAS INJECTOR

TECHNICAL FIELD

The inventions disclosed herein generally relate to devices and methods for injecting gases into an eye of an animal.

BACKGROUND OF THE INVENTIONS

Surgical procedures can require gases or other fluids to be injected into a target area for treatment of certain injuries, disorders and diseases. In the treatment of eye conditions such as macular holes, retinal tears and detachments, part of the surgical procedure can include the injection of gases or other fluids into the eye.

For example, retinal detachment is an eye disorder involving the separation of the retina from the Retinal Pigment Epithelium (RPE), the tissue that holds the retina in place. Retinal detachment can occur due to a retinal tear, traction on the retina, or inflammation which allows fluid to build up in the subretinal space thereby causing the retina to begin to separate from supporting RPE tissue. This disorder can also occur due to Posterior Vitreous Detachment (PVD), Proliferative Diabetic Retinopathy (PDR), injury, or neovascularization of the fibrous or vascular tissue causing the retina to be detached from the RPE. Such a condition, if not treated immediately, could lead to partial vision loss and potentially even blindness.

Treatment approaches for uncomplicated retinal detachments may include non-surgical techniques such as pneumatic retinopexy, laser photocoagulation, or cryopexy. More complicated retinal detachments require surgical intervention. Due to the risk of infection, which can potentially cause blindness, such surgeries are performed under sterile conditions in order to significantly reduce the potential for infection. Surgical methods include vitrectomy, which is the removal of the vitreous humor; dissection and removal of membranes, in the case of traction retinal detachments; and photocoagulation or cryopexy, in the case of additional retinal tears. Following such a surgical procedure, an intraocular gas tamponade may be used to hold the retina tissue in contact with the RPE which enables the retina to remain attached during the healing process after the surgical procedure.

Since intraocular pressure must be maintained relatively constant during the healing process, the gas chosen is typically one that expands at constant pressure (isobaric process). As such, the intraocular gas tamponade can be a gas bubble of air mixed with an expansile gas such as sulfur hexafluoride ($SF_6$), hexafluroethane ($C_2F_6$), or octafluoropropane ($C_3F_8$). The intraocular gas tamponade dissolves over time depending on the gas and concentrations used. For example, sulfur hexafluoride dissolves within 1-2 weeks when mixed with air at a concentration of approximately 20 percent, hexafluoroethane dissolves in approximately 4-5 weeks when mixed with air at a concentration of approximately 16 percent, and octafluoropropane dissolves in approximately 6-8 weeks when mixed with air at a concentration of approximately 12%. Changing the concentrations of these gases affects the duration.

Current practice involves use of gases contained in separate, multi-dose pressurized containers which are then transferred into a syringe for mixing with air and injection into the patient's eye. Therefore, during a surgical procedure, multiple non-sterile and sterile steps are required in order to fill the syringe with a desired concentration of gas and air. These non-sterile and sterile steps are typically performed by the non-sterile operating room circulating nurse and the sterile scrub technician supporting the surgeon in the sterile field. During a first non-sterile step, the circulating nurse prepares the non-sterile re-usable gas container by setting a pressure regulator connected to the gas container at the proper pressure. During a second step, the scrub tech prepares a sterile syringe by connecting a stopcock, filter, and tubing, in series, onto the syringe. During a third step, the tubing is connected to the gas container. The scrub tech carefully passes the free end of the sterile tubing through the invisible sterile barrier to the awaiting non-sterile circulating nurse. The non-sterile circulating nurse receives the tubing and carefully ensures that he/she does not contaminate the scrub tech nor any other of the sterile surfaces; and connects the tubing to the regulator on the gas container. During a fourth step, the syringe is then filled with gas from the container. The scrub tech and circulating nurse coordinate the opening of the pressurized container valve to release gas through the connected tubing, filter, stopcock, and into the syringe. The pressure of the released gas is sufficient to push the syringe plunger along the length of the syringe barrel and thus fill the syringe with gas. The scrub tech ensures that the gas does not push the plunger out of the open end of the syringe barrel and signals to the circulating nurse to close the gas container valve when the syringe approaches a fully filled condition. During a fifth step, the syringe is then purged of all air and gas in order to ensure that a substantial majority of air which may have been present within the syringe, stopcock, filter, and tubing, prior to filling with gas has been purged. The scrub tech turns the stopcock, to provide a means for the air and gas in the syringe to be released to the atmosphere, presses on the syringe plunger, and empties the syringe of all of its contents. The scrub tech then turns the stopcock in the opposite direction, returning the connection pathway to the tubing and the gas container.

Steps four and five are repeated several times to further reduce the amount of air that was initially in the syringe, stopcock, filter, and tubing; flushing the majority of the air from the syringe, stopcock, filter, and tubing and purging the system of air. During a sixth step, the syringe is then refilled with gas from the container. The scrub tech detaches the tubing from the filter and signals the circulating nurse to carefully take the tubing, removing it from the sterile field. During a seventh step, the scrub tech does not expel the full contents of the syringe, stopping the plunger such that only a measured volume of gas remains in the syringe. For example, the gas may be expelled such that only 12 mL remains within the syringe. During an eighth step, the scrub tech replaces the used filter with a new sterile filter and draws filtered room air into the syringe until the total air/gas mixture in the syringe is at a proper volume for the desired gas concentration.

For example, atmospheric air may be drawn into the syringe such that the total volume of air and gas is 60 mL therefore achieving a concentration of 20 percent. Since the pressurized containers are non-sterile, and the syringe and surgical area are sterile, completing the above-mentioned steps must be performed by at least one party in the non-sterile field (typically the circulating nurse), a second party in the sterile field (typically the scrub tech), and requires the coordination and communication between the two parties.

The procedure requires a complex set of steps which may increase the potential for errors occurring. An error in one of these steps can result in an improper concentration of gas being used which may result in having either an elevated pressure or reduced retinal tamponade duration thereby potentially causing ischemia or failure of the reattachment surgery, both of which potentially causing blindness. Additionally, the current practice results in a significant amount of wasted gas which is both expensive and harmful to the environment. Thus handling of such gases, especially in pressurized containers containing more than one dose, may present potential danger to the operator if mishandled. As such, some countries may even prohibit storage of these pressurized containers in the operating room.

While there have been some approaches to improve the current procedure, such as U.S. Pat. No. 6,866,142 to Lamborne et al., single-dose containers capable of being placed in the sterile field, and the Alcon® Constellation® system which allows filling and purging of gas, these approaches have been insufficient to address all the potential issues. Another approach is disclosed in U.S. Pat. No. 8,986,242 in which a syringe apparatus includes an internal pressurized canister of expansile gas in a volume limiting mechanism. In use, the volume limiting mechanism is set to a volume of expansile gas corresponding to ultimate desired concentration of a gas tamponade which can include an expansile gas and air. The expansile gas is released into the chamber of the syringe until the plunger of the syringe hits the volume limiting mechanism structures and the remaining expansile gas is discharged to the atmosphere. The filter is then attached to the outlet of the syringe mechanism and atmospheric air is drawn into the chamber of the syringe, through the filter, so as to create a mixture of expansile gas and air at the desired concentration for later injection.

SUMMARY OF THE INVENTION

An aspect of at least one of the inventions disclosed herein includes the realization that an intraocular gas injector device can be assembled and packaged in a manner that reduces or eliminates manipulations required of a user and can further reduce potential sources of contamination. For example, as noted above with regard to the usage of the devices disclosed in U.S. Pat. No. 8,986,242, an expansile gas is provided into an internal mixing chamber of a syringe device, with some excess expansile gas being discharged through the outlet of the syringe. Thereafter, a filter is attached to the outlet of the syringe and atmospheric air is drawn into the mixing chamber, through the filter.

An aspect of at least one of the inventions disclosed herein includes the realization that an intraocular gas injection device can include a syringe body, a source of therapeutic gas, and a filter preattached to the outlet of the syringe, for example, before the discharge of excess therapeutic gas through the outlet. In some embodiments, the gas injection device having the filter preattached thereto can be packaged in a sterile container for use in a surgical procedure. As such, a user can open the sterile container, remove the intraocular gas injection device and operate it with the filter in place throughout the gas mixing process. For example, with the filter preattached, a user can provide the expansile gas into the mixing chamber of the syringe, at least partially filling the mixing chamber with expansile gas, or another gas of choice, and in some modes of use, allow excess expansile gas to be discharged out of the mixing chamber, through the outlet of the syringe body, and through the filter then to the atmosphere. During such discharge of the excess expansile gas, filtering of the expansile gas would not provide any known, substantial direct beneficial effects. However, using the intraocular gas injector in such a mode, with the filter in place during the discharge of excess expansile gas, provides a reduced risk of contamination of various volumes of space within the device including those between the plunger of the syringe and the filter membrane of the filter device. Further, once the discharge of excess expansile gas is completed, the user can then draw an atmospheric air into the mixing chamber, through the filter, without opening the intermediate volumes of space to the atmosphere. Thus, the intermediate volumes of space between the filter membrane and the plunger of the syringe remain closed to the atmosphere, only receiving atmospheric air that has been filtered through the filter device.

After the user has drawn in the desired amount of atmospheric air, filtered through the filter device, the filter device can be removed and a desired instrument can be attached to the outlet of the syringe. For example, in some embodiments, a user may attach a needle for injecting the mixed expansile gas and atmosphere air into the eye of an animal or patient doe treatment of a detached retina. After attachment of such a needle, the user can flush the needle with the mixed expansile gas and atmospheric air in the mixing chamber. Thus, prior to surgical use, no volume of space between the filter membrane and the syringe plunger would be exposed to unfiltered atmospheric air.

Another aspect of at least one of the inventions disclosed herein includes the realization that filling of a variable volume gas mixer with a fixed amount of source gas can result in an insufficient expansion of the variable volume chamber and thus a failure to produce the desired concentration of mixed gas. Thus, an aspect of at least one of the inventions disclosed herein includes the realization that providing a flow restriction device onto the outlet of a filter which is mounted to the outlet of an intraocular gas injection device can provide beneficial and/or additional back pressure that can be beneficial for better ensuring that the mixing chamber expands to the desired volume of a therapeutic gas or a component of a therapeutic gas, such as an expansile gas.

Another aspect of at least one of the inventions disclosed herein includes the realization that a flow restrictor attached to the outlet of a downstream filter of an intraocular gas injector can generate an undesirably strong flow restriction during a process of drawing in ambient air or atmospheric air through the filter after the mixing chamber has been filled with therapeutic gas. Thus, an aspect of at least one of the inventions disclosed herein includes the realization that providing a removable flow restrictor to the outlet of a filter of an intraocular gas injection device can provide two beneficial modes of operation; generating a desirable back pressure during discharge of excess therapeutic gas during a filling phase of a mixing chamber, ensuring that the mixing chamber fully expands to the desired volume for containing a desired amount of therapeutic gas, then with the flow restrictor is removed, a user can manually expand the mixing chamber and draw atmospheric air through the filter, without the increased difficulty that would be associated with such an operation if the flow restrictor were in place. Thus, an aspect of at least one of the inventions disclosed herein includes an intraocular gas injection device having a downstream filter device and a removable flow restrictor at the downstream end of the filter device.

Another aspect of at least one of the inventions disclosed herein includes the realization that if a filter device is attached to the outlet of the syringe in an operating room, there is potential for foreign materials or contamination to enter the upstream end of the filter device and thus be contained in a volume disposed between the filter membrane and the plunger. Thus, even if some excess expansile gas is subsequently discharged through the filter, such contamination and/or foreign materials may be captured by the filter membrane then subsequently back flushed into the mixing chamber when atmospheric air is drawn in the reverse direction through the filter. Thus, an aspect of at least one of the inventions disclosed herein includes configurations and methods of operation in which the potential for contamination and/or foreign materials to enter volumes of space disposed between the filter membrane and the plunger are reduced.

DETAILED DESCRIPTION OF THE PREFERRED EMBODIMENT

Figure 1A:
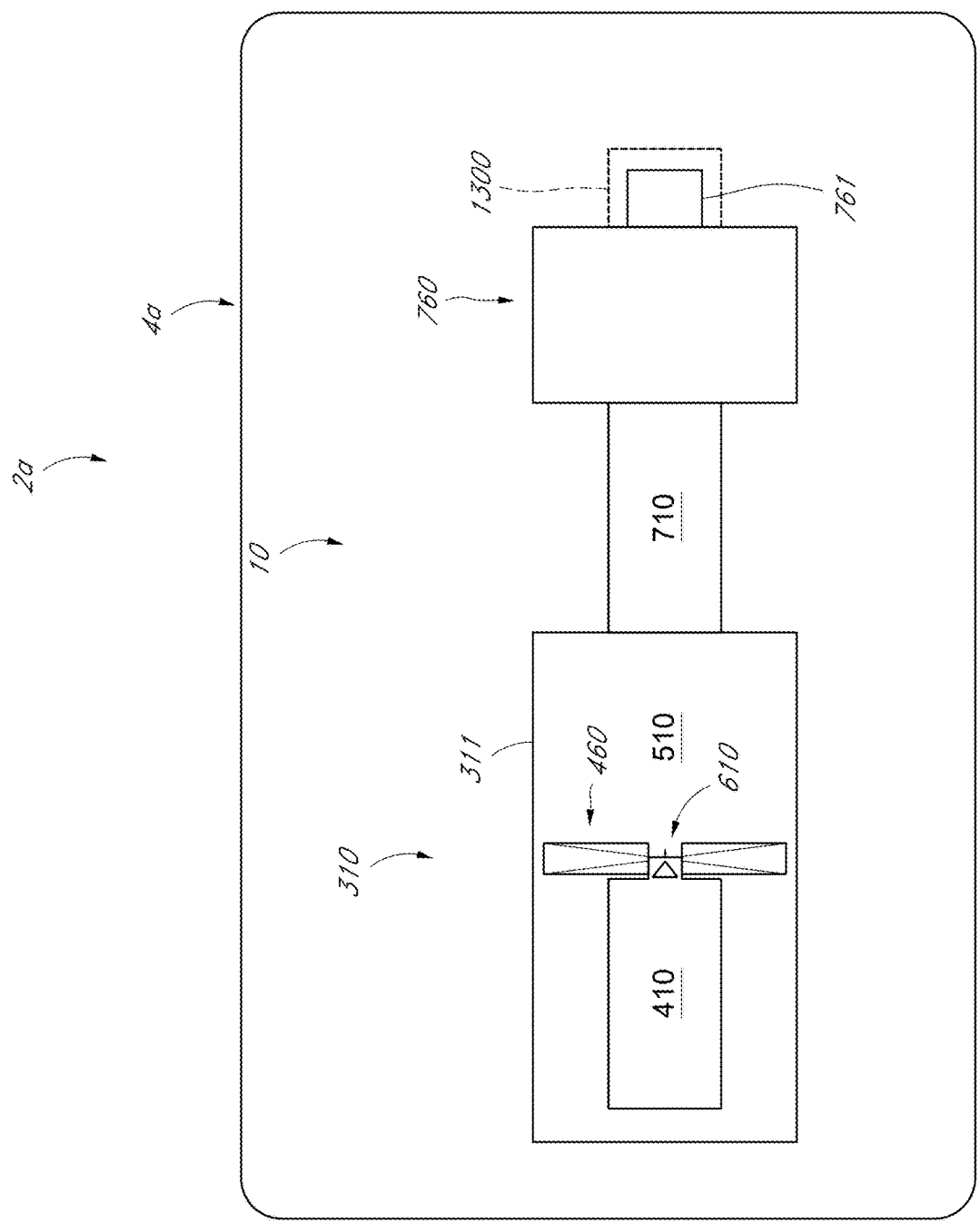
FIG. 1A is a schematic diagram of an embodiment of a gas mixing device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the proceeding technical field, background, brief summary, or the following detailed description.

Certain terminology may be used in the following description for the purpose of reference only, and thus are not intended to be limiting. For example, terms such as "upper", "lower", "above", and "below" refer to directions in the drawings to which reference is made. Terms such as "proximal", "distal", "front", "back", "rear", and "side" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures.

As used herein, the terms "front" and "distal" refer to the parts of the subject apparatus which are located further away from the user (e.g., surgeon) of the apparatus during an injection operation. As used herein, the terms "rear" and "proximal" refer to the parts of the apparatus which are located closer to the user (e.g., surgeon) of the apparatus during an injection operation.

Apparatus for Mixing Two Gases

FIG. 1A illustrates an embodiment of a gas mixture kit 2 that can include a gas mixture apparatus 10 enclosed in a container 4. The container 4 can be any type of container appropriate for use in containing components of a surgical kit, with a sterilized internal environment, for use in a surgical room, such as within a sterilized field of a surgical room, for use during a surgery. In some such containers, a thermoformed plastic tray includes structures for retaining the components that contain surgical components in a predetermined arrangement and a frangible seal made with a thin membrane-type material. The surgical components, in some embodiments, including the gas mixture apparatus 10 are sterilized and inserted into the container 4 in a sterilized environment, and in some embodiments, with an inert gas sealed therein. Other types of containers can also be used.

The gas mixture apparatus 10 can be configured to form a therapeutic gas or components for a therapeutic gas. For example, the gas mixture apparatus 10 can be configured to receive a therapeutic gas or a component of a therapeutic gas and a second gas, which can be in some embodiments, atmospheric air, into a mixing chamber for subsequent discharge for therapeutic use. For example, in some embodiments, the gas mixing apparatus 10 can be used for creating a therapeutic gas mixture for injection into a patient, and in some embodiments, the eye of a patient.

With continued reference to FIG. 1A, the gas mixture apparatus 10 can comprise a mixing system 310, a pressure regulation system 710, and a filter device 760. The mixing system 310 can include an outer housing 311, a therapeutic gas source 410, and a mixing chamber 510. The mixing chamber 510 can be defined by a portion of the housing 311 and a movable wall, such as a plunger 460. The plunger 460 can be in the form of a plunger typically provided in a syringe device.

The mixing system 310 can also include a pressure regulation system 610 disposed between the source 410 and the mixing chamber 510. The pressure regulation system 610 can include a valve configured to retain the source 410 in a closed condition and, upon actuation, release the contents of the source 410 into the mixing chamber 510, through the valve 610.

The pressure regulation system 710 can be configured to control a flow of gas into an out of the mixing chamber 510. For example, the pressure regulation system 710 can be configured to allow excess gas, originally from the source 410, provided into the mixing chamber 510, to escape to the atmosphere. For example, the pressure regulation system 710 can be configured to controllably release gas from the mixing chamber 510 that is at a pressure greater than atmospheric pressure. Additionally, the pressure regulation system 710 can be configured to allow a gas to enter the mixing chamber 510 when the pressure within the mixing chamber 510 is below atmospheric.

The filter device 760 can include a filter membrane (not shown) or another filtering device configured to remove particles, foreign materials, or other substances from gases flowing therethrough. The filter device 760 can include an outlet end 761 communicating with the atmosphere. The outlet 761 can be used to discharge gas from the mixing chamber 510, as well as allow the admission of atmospheric air into the filter device 760 for mixing in the mixing chamber 510. Optionally, the filter device 760 can include a further flow restrictor 1300 configured to restrict a flow out of and/or into the outlet 761.

The kit 2 can be prepared in a sterilized environment, and receive the gas mixture apparatus 10, with or without the optional flow restrictor 1300, such that the filter member 760 is attached to the mixing apparatus 310 and sealed within the container 4. In use, a practitioner can open the container 4 and release a therapeutic gas or gas component from the source 410 into the mixing chamber 510.

By way of the introduction of the gas in the mixing chamber 510, the plunger 460 would move to the left (as viewed in FIG. 1A) thereby allowing the volume of the mixing chamber 510 to expand in accordance with the introduction of the therapeutic gas from the source 410 into the mixing chamber 510. For example, in some embodiments, the source 410 is a pressurized container of a therapeutic gas or component thereof. Thus, the release of the pressurized gas into the mixing chamber 510, would raise the pressure within the mixing chamber 510, thereby urging the plunger 460 to move and thereby expand the volume of mixing chamber 510.

The pressure regulation system 710 can include a valve mechanism configured to open when subject to pressures greater than atmosphere and, simultaneously, provide a flow restriction thereby creating some back pressure sufficient to cause the plunger 460 to move and allow the mixing chamber 510 to expand. When the plunger 460 has moved sufficiently to allow the mixing chamber 510 to expand to the desired volume of therapeutic gas, the pressure regulation device system 710 will allow the release of the remaining excess gas from the source 410 to flow out through the filter device 760 and the outlet 761. As excess gas flows through the filter device 760, the upstream side of the filter device 760 would not be expected to capture any foreign materials or contaminants as all interior spaces within the device 10 would have been presterilized and stored in a sterilized environment within the container 4. Thus, during the discharge of excess gas from the mixing chamber 510, the filter device 760 would not likely serve any desired filtering functions.

After the chamber 510 has been filled with the desired volume of therapeutic gas or component thereof, the plunger 460 can be manually moved, for example, toward the left (as viewed in FIG. 1A), so as to draw atmospheric air into the outlet 761, through the filter device 760, through the pressure regulation system 710 and into the mixing chamber 510. As such, the filter device 760 can capture foreign material and/or other undesirable gases that may be present in the atmosphere from entering and prevent those substances from entering the mixing chamber 510.

The plunger 460 can be moved to a desired location corresponding to the desired mixture of gases from the source 410 and atmospheric air. After the desired mixture has been formed in the mixing chamber 510, the user can remove the filter 760, and attach a delivery device (not shown), such as a hypodermic needle to the pressure regulation device 710, for further discharge.

For example, in the context of using the device 10 for mixing expansile gas from the source 410 with atmospheric air for the treatment of a detached retina, a user may attach a hypodermic needle to the downstream side of the pressure regulation system 710, in the illustrated location of the filter device 760. With the needle attached as such, a user can manually move the plunger 460 to the right (as viewed in FIG. 1A) and flush the hypodermic needle with uncontaminated mixed gas from within the mixing chamber 510, then continue the procedure for providing therapy to a patient, for example, by introducing a bubble of mixed expansile gas and atmospheric air from the mixing chamber 510 into the eye of a patient.

In some embodiments, as described above, the device 10 can include a flow restrictor 1300. The flow restrictor 1300 can provide additional restriction of flow out of and into the outlet 761. Thus, during the addition of therapeutic gas into the mixing chamber 510, the flow restrictor 1300 can provide additional back pressure and thus assurance that sufficient positive pressure will be generated in the mixing chamber 510 so as to move the plunger 460 (to the left) and thus allow the mixing chamber 510 to fully expand to the desired volume associated with the desired final concentration of the mixture in the mixing chamber 510.

Figure 1B:
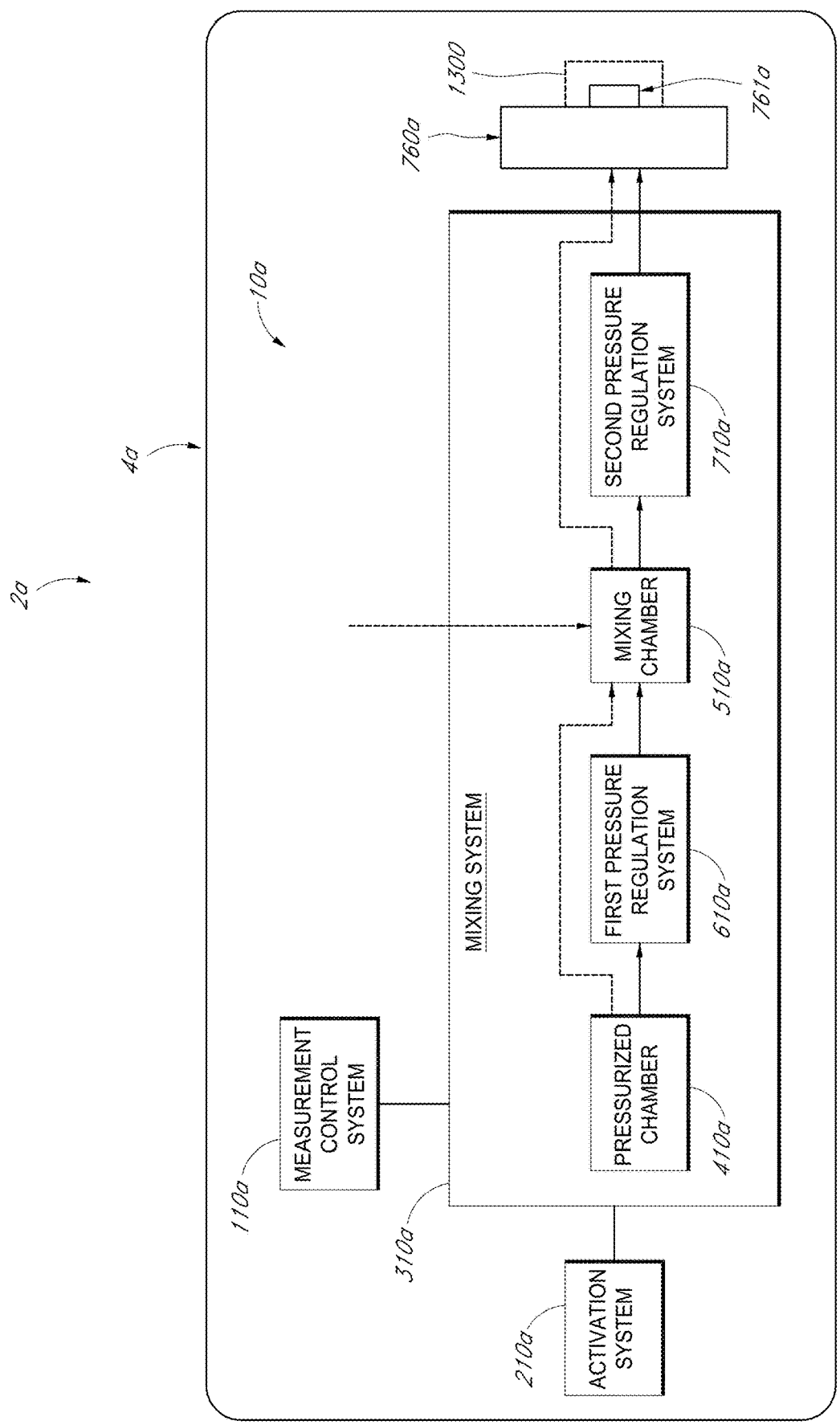
FIG. 1B is a further embodiment of a gas mixture apparatus.

FIG. 1B illustrates a further embodiment of the gas mixture kit 2, identified generally by the reference numeral 2a. The kit 2a includes a gas mixture apparatus 10a contained within a container 4a. As described above with reference to the container 4, the container 4a can contain the system 10a in a sterilized state for opening and use in a surgical environment. The gas mixture apparatus 10a can comprise a measurement control system 110a, an activation system 210a, and a mixing system 310a configured to create a mixture of two or more gases at a desired concentration ratio, and a preattached filter 760a. Further, optionally, the kit 2a can include a removable flow restrictor 1300 attached to an outlet 761a of the filter device 760a. The mixing system 310a can also optionally include a pressurized chamber 410a and a mixing chamber 510a.

The mixing system 310a can also include a pressure regulation system to enhance the operation of the mixing system 310a. In some embodiments, the mixing system 310a additionally includes a first pressure regulation system 610a and a second pressure regulation system 710a.

The measurement control system 110a can be in the form of a metering mechanism contained within the mixing system 310a to control certain aspects of the devices contained therein. In some embodiments, the measurement control system 110a can be a variable and user-adjustable device. The activation system 210a can be operatively coupled to the pressurized chamber 410a in order to activate operation of the device and commence the mixing of gases within the mixing system 310a.

The optional pressurized chamber 410a can contain at least one of the two or more gases to be mixed within the mixing system 310a. In some embodiments, the gas contained within the pressurized chamber 410a can be at a pressure higher than surrounding ambient conditions. Additionally, the pressurized chamber 410a can contain gases at concentrations different from that in the atmosphere. The pressurized chamber 410a can be configured such that it is in fluid communication with the first pressure regulation system 610a. In other embodiments, the pressurized chamber 410a can be in direct fluid communication with the mixing chamber 510a. The pressurized chamber 410a can be configured such that it is internally contained within an injector apparatus. The pressurized chamber 410a can also be configured such that it is external to the injector apparatus. The first pressure regulation system 610a can be configured to maintain a pre-configured pressure differential between the pressurized chamber 410a and the mixing chamber 510a.

The mixing chamber 510a can be configured to receive gas from the pressurized chamber 410a either directly or via the first pressure regulation system 610a. In some embodiments, the mixing chamber 510a can additionally be configured to receive a second gas to be mixed from outside the mixing system 310a such as an external gas container or the atmosphere. The mixing chamber 510a can be configured such that it is in fluid communication with the second pressure regulation system 710a at a mixing chamber 510a exit point. In other embodiments, the mixing chamber 510a can be in direct fluid communication with the atmosphere at a mixing chamber exit point. Examples of each of these subsystems are described separately below.

In some embodiments, the measurement control system 110a is configured to control concentrations of the gas within the gas mixture apparatus 10a. In some embodiments, the measurement control system 110a is operatively coupled with the mixing system 310a. Preferably, the measurement control system 110a is operatively coupled with either the pressurized chamber 410a or the mixing chamber 510a such that the measurement control system 110a can modify variable aspects of the pressure chamber 410a and/or the mixing chamber 510a.

In some embodiments, the measurement control system 110a is capable of controlling characteristics such as, but not limited to, the volume of gas contained within the mixing chamber 510a. Other characteristics, such as pressure, are also contemplated as being controllable by the measurement control system 110a. Preferably, the measurement control system 110a is variable such that a user can be able to select a desired concentration ratio of gas that can be expelled from the gas mixture apparatus 10a. This advantageously allows a user to have only a single gas mixture apparatus 10a for a wide range of desired concentration ratios. As such, the measurement control system 110a can include user-operable switches such as dials which vary the operation of components within the mixing system 310a such as the pressurized chamber 410a, the mixing chamber 510a, the first pressure regulation system 610a, and the second pressure regulation system 710a.

The pressurized chamber 410a can be configured to store one or more gases within an interior space of the pressurized chamber 410a for a period of time prior to mixing the two or more gases in the gas mixture apparatus 10a. The conditions within the interior space is configured to be different than those of atmospheric conditions and therefore the interior space should generally reduce the release of such gases out of the interior space or reduce the entry of non-stored gases into the interior space until mixing of the two or more gases is to be performed.

In some embodiments, the one or more gases within the interior space are at a higher pressure than ambient atmospheric conditions. Additionally, the one or more gases can also be gases at concentrations different than those at ambient atmospheric conditions. In some embodiments, the interior space can be divided into separate subsections or portions for holding one or more gases. These separate portions of the interior space can therefore be kept at different pressures and/or different concentrations of gases.

In some embodiments, the gases can additionally be placed in different structural units within the interior space. Such structural units can be used to more effectively reduce the release of stored gases and/or reduce the entry of non-stored gases. In some embodiments, the stored gases of the pressurized chamber 410a are pre-loaded from the time of manufacture. In other embodiments, it is contemplated that the contents of the pressurized chamber 410a can be loaded by a user of the gas mixture apparatus 10a. For example, the stored gases can be contained in a removable cartridge-like device which can advantageously facilitate the replacement of such gases.

In some embodiments, the activation system 210a is configured to activate the operation of the gas mixture apparatus 10a and commence the process of mixing the two or more gases within the mixing system 310a. As such, the activation system 210a is operatively coupled to the mixing system 310a and can be coupled to both the mixing chamber 310a and the pressurized chamber 410a. The activation system can cause the pressurized chamber 410a to activate and release gases contained therein into the mixing chamber 510a. In some preferred embodiments, the activation system 210a can cause the pressure within the pressurized chamber 410a to increase such that the first pressure regulation system 610a is activated thereby allowing fluid flow from the pressurized chamber 410a into the mixing chamber 510a. The activation system 210a can include a device configured to activate a separate portion of the pressurized chamber 410a that contains higher pressure gas than the remainder of the pressurized chamber 410a such that the pressure within a separate section of the pressurized chamber 410a increases. In a preferred embodiment, the activation system 210a can open a sealed device within the mixing chamber 510a to release pressurized gas and thereby release pressure throughout the pressurized chamber 410a. In such embodiments, the activation system 210a can include a puncturing device capable of piercing the seal. Other devices and techniques can also be used. Use of an activation system 210a provides advantages by allowing the gas mixture apparatus 10a to potentially be pre-filled prior to use and safely stored.

The activation system 210a can also be operably coupled to the mixing chamber 510a allowing a user to manually vary certain aspects of the device. In some embodiments, the activation system 210a can be used to modify the volume of the mixing chamber 510a. The activation system 510a can also be used to modify the pressure of the mixing chamber 510a.

In some embodiments, the first pressure regulation system 610a is configured to serve as a separation mechanism between both the pressurized chamber 410a and the mixing chamber 610a. The first pressure regulation system 610a can activate upon reaching a pre-configured pressure differential between both the pressurized chamber 410a and the mixing chamber 510a. In some preferred embodiments, the first pressure regulation system 610a can be comprised of at least one valve assembly. The valve assembly can open when pressure within a portion of the pressurized chamber 410a is higher than the pressure in the mixing chamber 510a. The valve assembly can be a check valve, clack valve, non-return valve, or one-way valve. Such valves can also include ball check valves, diaphragm check valves, swing check valves, stop-check valves, lift-check valves, in-line check valves, and duckbill valves. Other pressure regulation mechanisms can also be used. Additionally, it is contemplated that first pressure regulation system 610a can also be activated by other means other than pressure differentials across the system 610a.

In some embodiments, the mixing chamber 510a is configured to serve as a space within which the two or more gases can be mixed to obtain a desired concentration ratio of the gases. The mixing chamber 510a can be configured to have a variable volume, adjustable upon use of the activation mechanism. The mixing chamber 510a can receive the gases to mix solely from the pressurized chamber or from gases already existing within the mixing chamber 510a. The mixing chamber 510a can also receive gases from secondary sources. In some embodiments, the mixing chamber 510a can receive air from the atmosphere to mix with the gases received from the pressure chamber 310a and/or gases already existing within the mixing chamber 510a.

In some embodiments, the second pressure regulation system 710a is configured to serve as a separation mechanism between both the mixing chamber 510a and the surrounding atmosphere. The second pressure regulation system 710a can activate upon reaching a pre-configured pressure differential between both the mixing chamber 510a and the surrounding atmosphere. In some preferred embodiments, the second pressure regulation system 710a can be comprised of at least one valve assembly. The valve assembly can open when pressure in the mixing chamber 510a is higher than the pressure in the surrounding atmosphere. The valve assembly can be a check valve, clack valve, non-return valve, or one-way valve. Such valves can also include ball check valves, diaphragm check valves, swing check valves, stop-check valves, lift-check valves, in-line check valves, and duckbill valves. Other pressure regulation mechanisms can also be used. Additionally, it is contemplated that second pressure regulation system 710a can also be activated by other means other than pressure differentials across the system 710a.

The kit 2a can also include a filter device 760a attached to an outlet of the mixing chamber 510a and/or an outlet of the second pressure regulation system 710a. The filter device 760a can include an outer housing and an internal filtering component, such as a membrane with a desired porosity or aperture size, for filtering out undesired foreign particles, substances, and/or gases. The filter device 760a can include an outlet 761a communicating with the atmosphere. During assembly of the kit 2a, the mixing device 10a, with the components 110a, 210a, 310a, 410a, 510a, 610a, 710a, and the filter device 760a attached in a sterilized packaging room and sealed within the container 4a in a sterilized state, and optionally, packed with a sterilized, inert gas. Thus, all of the empty internal volumes within and between the components 110a, 210a, 310a, 410a, 610a, 510a, 710a, and 760a will be either sterilized and/or filled with an inert gas within the sealed package 410a. Optionally, as noted above, the kit 210a can also include an additional flow restrictor 1300 attached to the outlet 761a of the filter device 760a.

Operational Overview

Figure 2A:
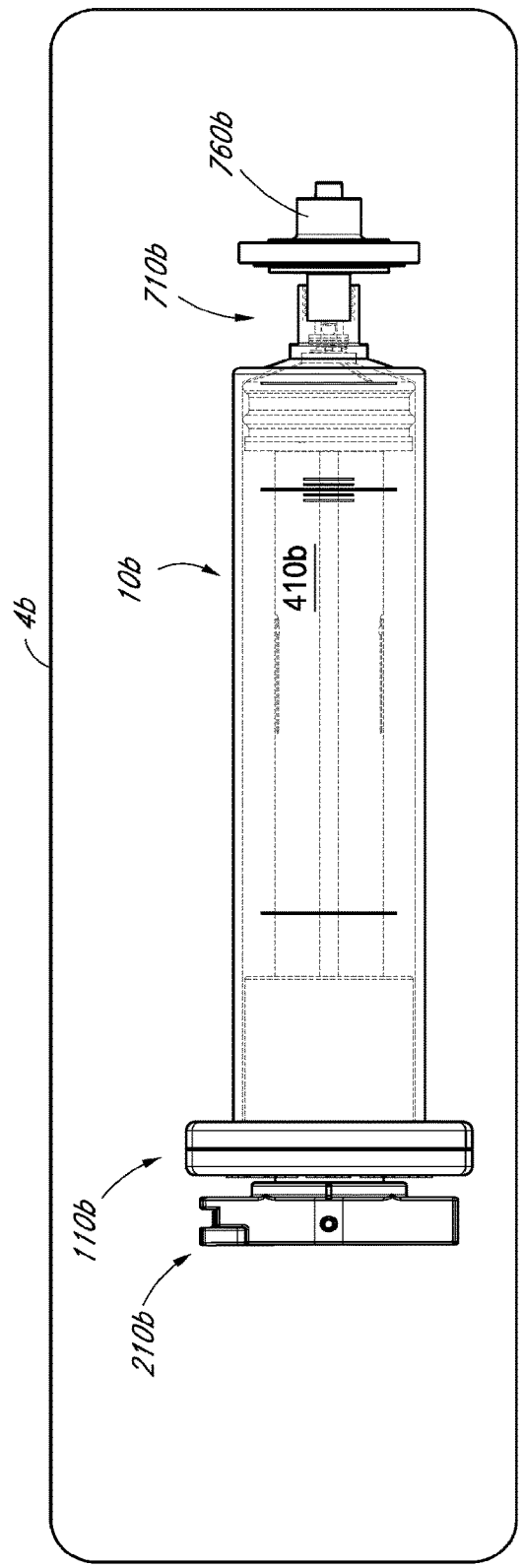
FIG. 2A is another embodiment of a gas mixture apparatus shown packaged in an enclosed container designed for deployment in a surgical room.

With reference to FIGS. 2A-2D, the operation of an embodiment of a gas mixture apparatus 10b is illustrated. With reference to FIG. 2A, the apparatus 10b can be in an initial phase with the activation system 210b in a first or "closed" position and contained in the package 4b. In this phase, the device 10b is in a fully sterilized state, with all internal volumes, including those between the filter element of the filter device 760 and the plunger 460 (not shown) sterilized and/or filled with a sterilized inert gas.

A practitioner or other user can remove the device 10b from the package 4b and use the measurement control system 110b to select the desired concentration of therapeutic gas for mixing. Then, the user can use the activation system 210b to release gas from the gas source 410b into the mixing chamber 510b.

Figure 2B:
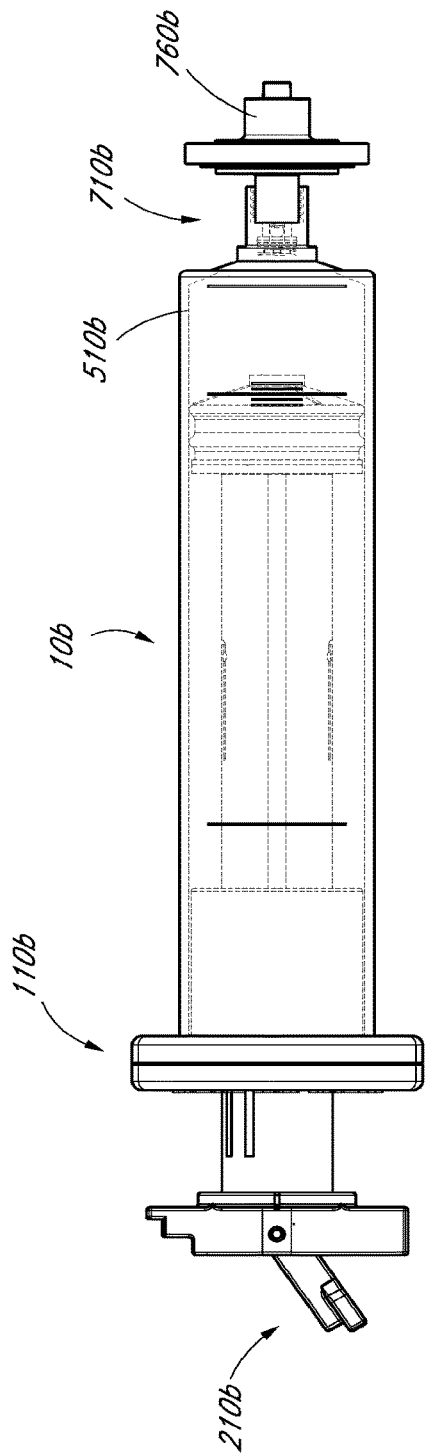
FIG. 2B is a schematic side elevational view of the gas mixture apparatus shown in a first phase of operation.

For example, with reference to FIG. 2B, gas contained within the pressurized chamber 410b can be released and, in embodiments containing a first pressure regulation system, the first pressure regulation system can open in response to a change in pressure within the chamber. As such, fluid can flow from the pressurized chamber into the mixing chamber 510b thereby causing an increase in the volume of the mixing chamber 510b. However, due to components of the measurement control system 110b, the plunger 460b of the mixing chamber 510b is stopped at the user-selected first volume and cannot expand beyond this first volume. This first volume can be set based on the desired concentration of the injectable volume. During this first phase of operation, excess gas can also be bled from the mixing chamber 510b via the second pressure regulation system 710b. Once the mixing chamber has reached this first volume, the first phase of operation is complete and the second phase of operation begins.

During the second phase of operation, the mixing chamber 510b can remain at the first volume while pressure within the mixing chamber 510b is bled from the system via the filter 760 and the second pressure regulation system 710b. By overfilling the mixing chamber 510b with the desired gas, and then bleeding off that gas, this helps to ensure that any amount of atmospheric gas or inert gas provided into the container at the time of packaging within the mixing chamber 510b, which may have been contained in the mixing chamber 510b prior to activation, is substantially purged from the mixing chamber 510b and displaced by the gas originally contained in the pressurized chamber. Once the pressure within the mixing chamber 510b has reached a configured value based on the configuration of the second pressure regulation system 710b, bleeding of the gas within the mixing chamber 510b ceases and the second phase of operation is complete.

Figure 2C:
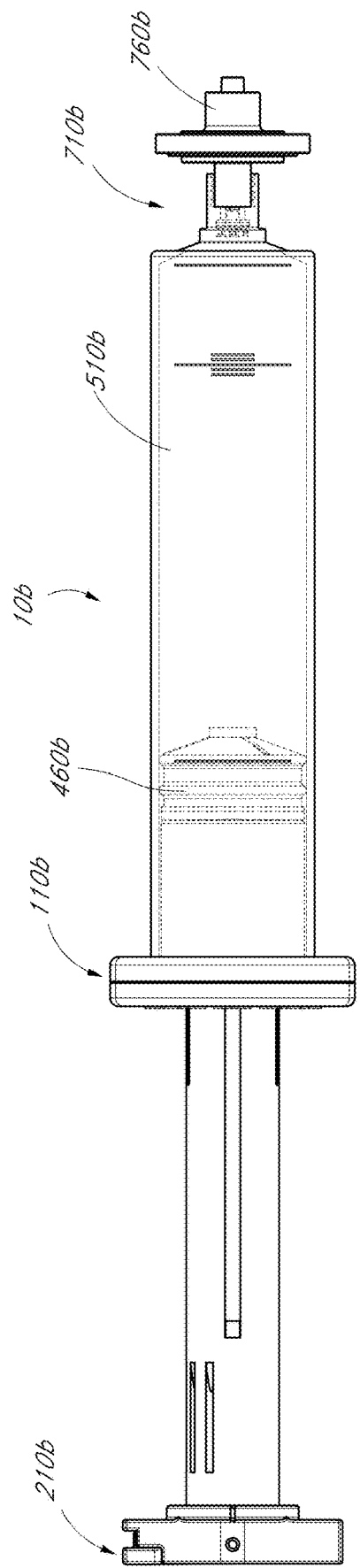
FIG. 2C is the gas mixture apparatus shown in a second phase of operation.

During a third phase of operation, as shown in FIG. 2C, once sufficient time has elapsed for the gas to reach ambient pressure, the user can then set the activation system 210b to the first or "closed" position thereby unlocking the measurement control system 110b. The user can then manually expand the volume of the mixing chamber 510b to the injectable volume. As the user manually expands the volume of the mixing chamber 510, ambient air is drawn from the atmosphere, through the filter device 760b, and into the mixing chamber 510b. The filter 760b thereby can filter out foreign particulates or gases from the ambient air before that air enters chamber 510b.

Figure 2D:
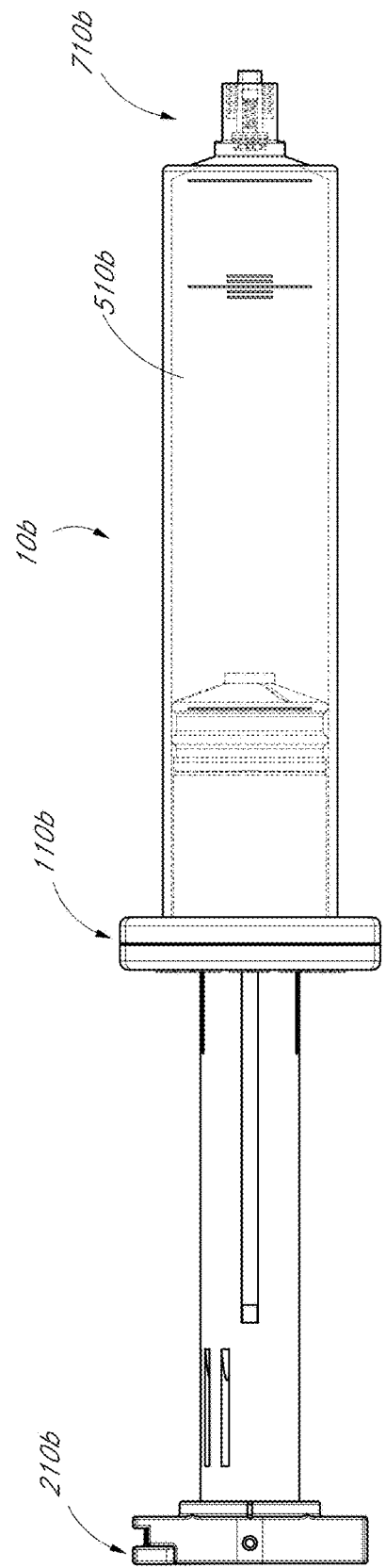
FIG. 2D is the gas mixture apparatus shown in a third phase of operation.

Once the third phase is complete, with reference to FIG. 2D, the filter device 760b can be removed and an additional device configured for the delivery of the therapeutic gas in the mixing chamber 510b, can be attached (not shown). For example, a hypodermic needle could be attached to the device 10b for supporting therapeutic delivery of the therapeutic gas within the mixing chamber 510b to a patient. In some embodiments, the gas within the mixing chamber 510b can be a mixture of expansile gas and filtered atmospheric air for the treatment of detached retinas. In such a scenario, a hypodermic needle attached to the device can be purged of any gas that may exist therein by depression of the plunger for 460b to discharge some of the gas from the mixing chamber 510b through the hypodermic needle. Thereafter, the needle can be inserted into a patient's eye and gas from the mixing chamber 510b can be used to generate one or more gas bubbles within the patient's eye for treatment of a detached retina. Other uses are also possible.

In other embodiments, a fewer or greater number of phases of operation can be performed. In some embodiments, only a single phase of operation can be performed. For example, the pressurized chamber 410a can contain a gas at a pre-set concentration level. During the single phase of operation, the user can activate the apparatus 10b such that a gas or fluid flows from the pressurized chamber 410a and into a second chamber, such as the mixing chamber 510a, until the chamber reaches a configured volume. The gas or fluid can also be expelled or bled off using a pressure regulation system until a desired pressure is achieved within the chamber. After expelling the gas, the apparatus 10b can be ready for use. As should be apparent to one of skill in the art, in such an embodiment, little to no mixing may in fact be performed.

System Overview

Figure 3:
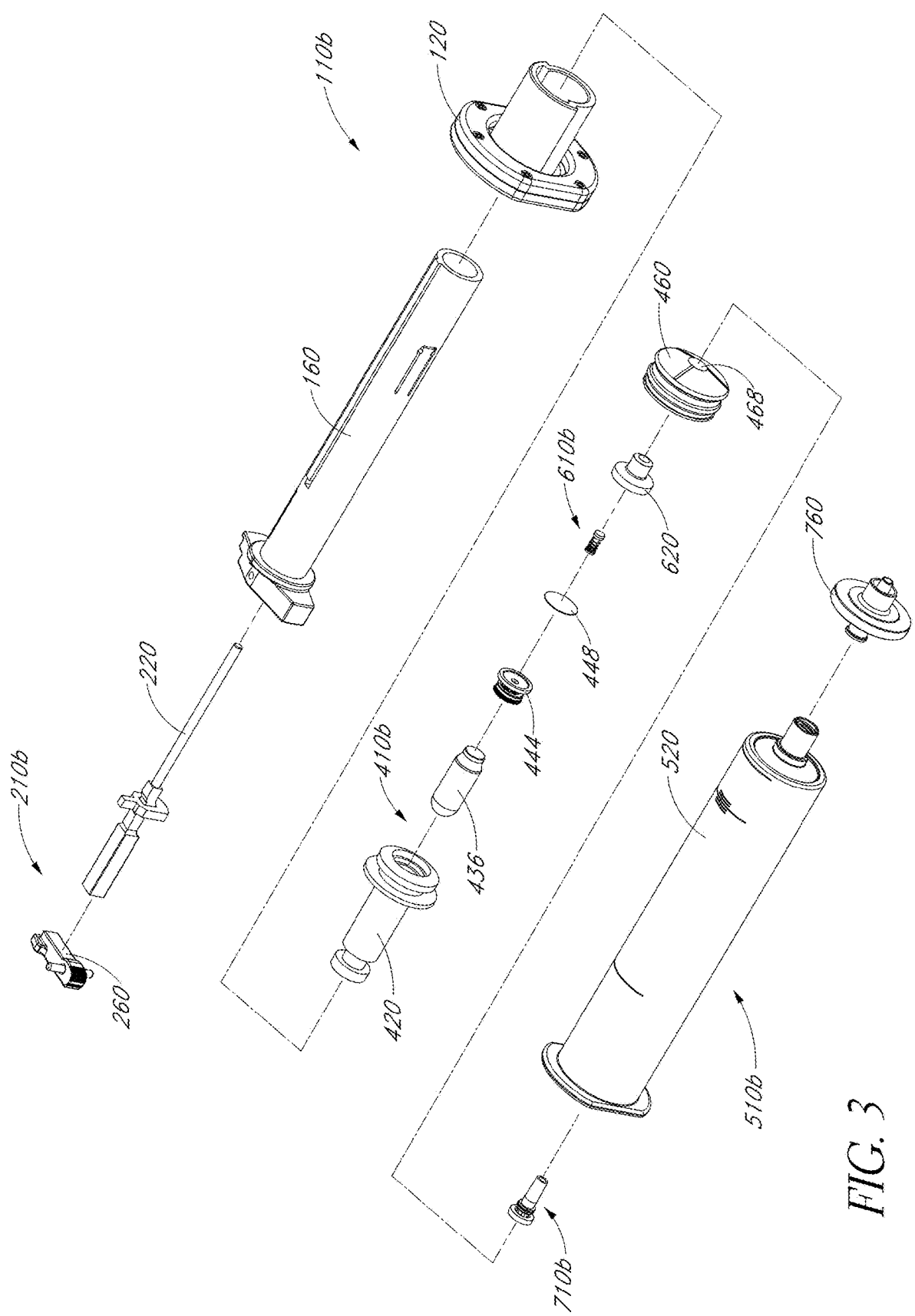
FIG. 3 is an exploded view of the components of the gas mixture apparatus.

With reference to FIG. 3, components of an embodiment of a gas mixture apparatus 10b are shown which comprise a measurement control system 110b, an activation system 210b, a pressurized chamber 410b, a mixing chamber 510b, a first pressure regulation system 610b, and a second pressure regulation system 710b. The measurement control system 110b can comprise a metering dial 120 and a plunger body 160 which can be inserted into the metering dial 120. The activation system 210b can comprise an actuation rod 220 and activation switch 260. The activation system 210b can be operatively coupled to the measurement control device 110b to control the operation of the gas mixture apparatus 10b. The activation system 210b can be inserted into the plunger body 160.

The pressurized chamber 410b can be comprised of a housing 420, a canister 436 containing a gas, a release mechanism 444 to release the gas contained within the canister 436, a filter 448 to reduce the amount of non-gas or bacteria material flowing out of the housing 420, and a plunger seal 460. The mixing chamber 510b can be comprised of a syringe body 520. The first pressure regulation system 610b can comprise a valve body and associated valve components. The second pressure regulation system 710b can also comprise associated valve components.

Measurement Control System and Activation System

Figure 4:
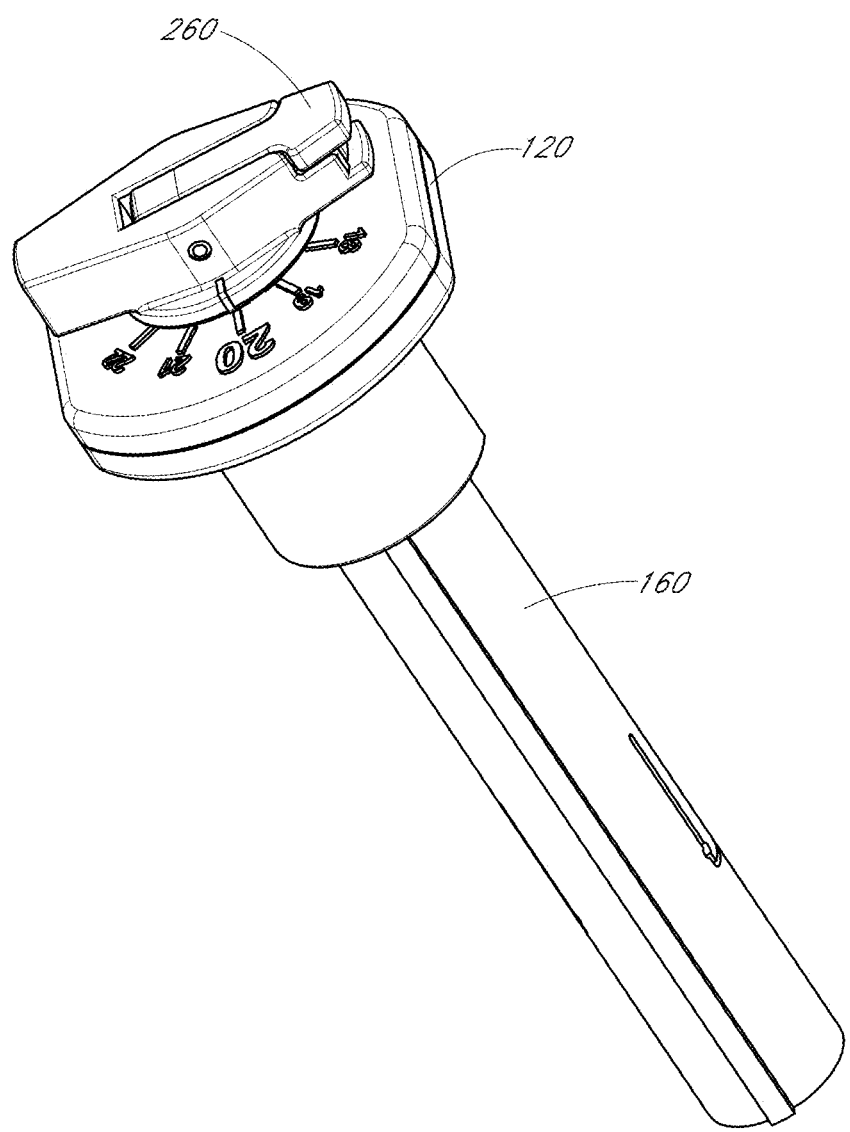
FIG. 4 is a perspective view of a measurement control system and activation system of the gas mixture apparatus.

With reference to FIG. 4, an embodiment of a combined measurement control system 110b and activation system 210b is shown. The measurement control system 110b can comprise a metering dial 120 and a plunger body 160. The activation system can comprise an actuation rod 220 (shown in FIG. 7) and an activation switch 260.

Figure 5B:
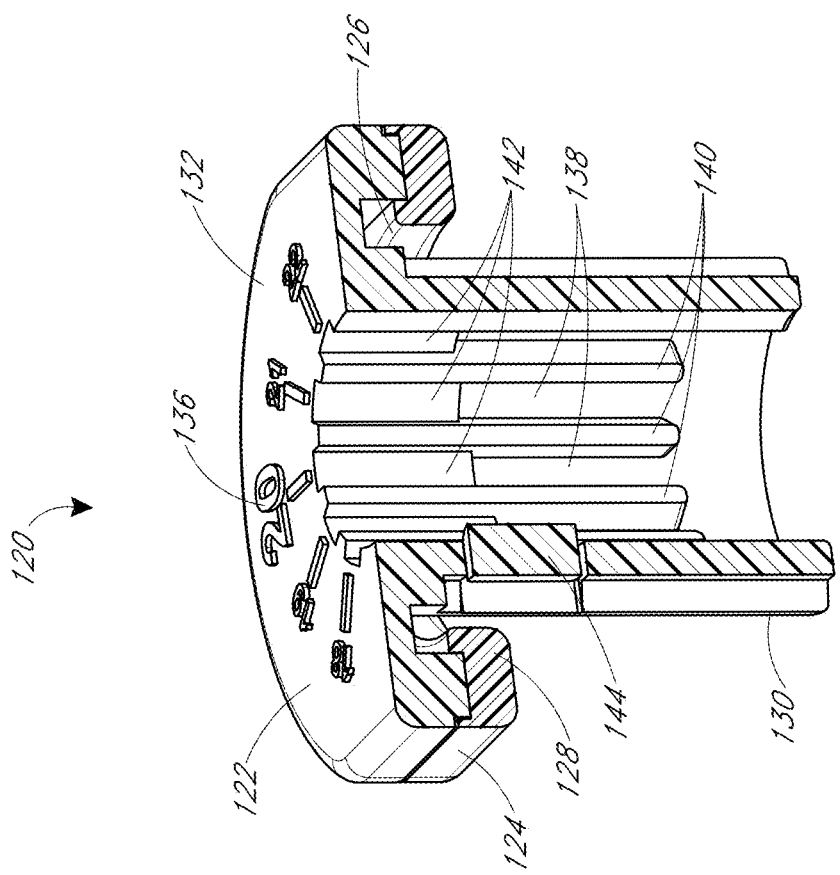
FIG. 5B is a sectional view of a metering dial of the measurement control system of FIG. 4.
Figure 5A:
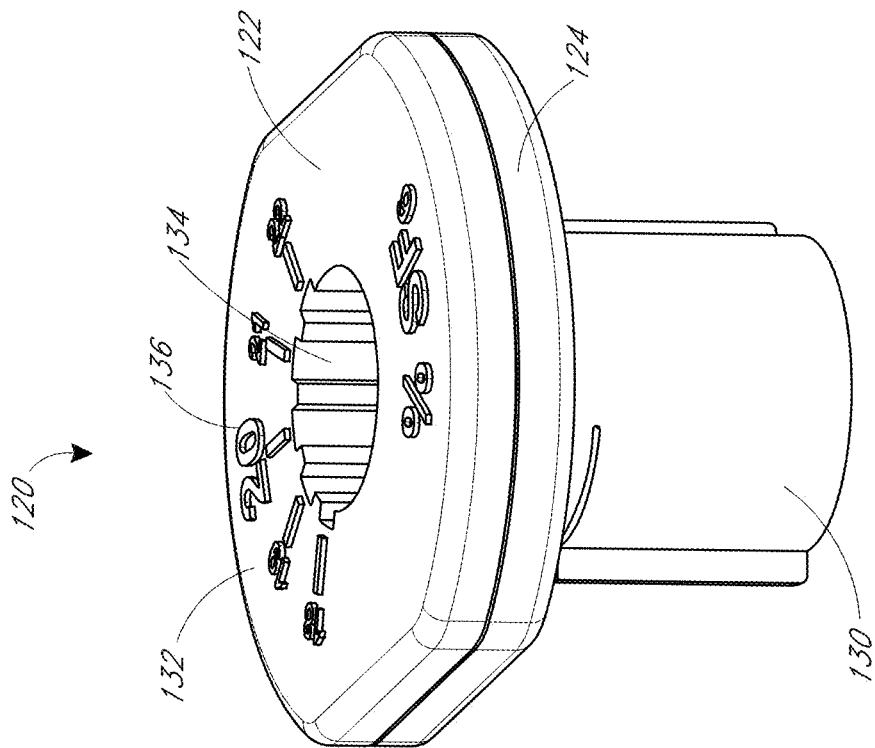
FIG. 5A is a perspective view of a metering dial of the gas mixture apparatus.

With reference to FIGS. 5A and 5B, an embodiment of a metering dial 120 of the gas mixture apparatus 10b is shown which is configured to allow a user of the apparatus 10b to selectively vary the concentration of an injectable volume. The metering dial 120 is comprised of two structural components—a metering body 122 and a metering cap 124 which can be coupled to the metering body 122 so as to allow the metering dial 120 to be releasably attached to another component of the apparatus 10b. This can advantageously facilitate assembly of the apparatus and, in some embodiments which are reusable, can facilitate disassembly for resterilization. In some embodiments, the metering cap 124 can be releasably attached to the metering body 122 using fasteners such as screws, rivets, clips, and other fastening mechanisms known in the art. Attachment of the metering cap 124 to the metering body 122 can form an annular slot 126 and an annular lip 128 such that the metering dial 120 can be attached to another component of the apparatus 10b. For example, the annular slot 126 and annular lip 128 can correspond to a flange 526 located on the syringe body 520.

The metering body 122 can have a generally cylindrical member 130 with a flange 132 at the top end and a channel 134 substantially centered on the cylindrical member 130 and running throughout the entire meter body 122. Since the meter body 122 is configured to control the concentration of the gas in the injectable volume, the meter body 122 can include metering indicators 136 along a surface viewable by a user of the apparatus 10b in a fully assembled state. In the illustrated embodiment, the metering indicators 136 are located on a top surface of the flange 132 although any location which can be viewed by the user can be used. The metering indicators 136 can provide the user of the device with information regarding the operation of the apparatus 10b. In the illustrated embodiment, the metering indicators 136 show a range of numbers from 18, 19, 20, 21, and 22 corresponding to concentrations of sulfur hexafluoride ($SF_6$) which would be produced in the injectable volume if the apparatus 10b is activated. As should be apparent to one of skill in the art, the ranges used can depend upon the gas used and the application for the gas. Furthermore, in some embodiments, this range can be further divided to provide enhanced control over the desired concentration.

The metering body 122 can have slots 138, slot 138, and variable stops 142 corresponding to the metering indicators 136. In the illustrated embodiment, the metering body 122 has five separate slots 138 located along an inner surface of the channel 134 which correspond to the five integer values stated above. In other embodiments, the metering body 122 can have fewer or greater slots than the number of values provided by the metering indicators 136.

Corresponding with each of these slots 138 are variable stops 142 which extend inwardly from the slots 138. As illustrated above, these variable stops 142 can be in the form of surfaces extending from the top surface of the flange 132 having lower end surfaces 142a disposed at set distances spaced from the bottom end of the tubular body 130. In some embodiments, the variable stops 142 need not extend from the top surface but instead are minor protrusions with lower end surfaces 142a disposed at set distances towards the bottom end of the cylindrical member 130. These variable stops 142 are configured to interact with components contained in the plunger body 160 such as a latch 228, or the plunger body 160 itself to control the expansion volume of the mixing chamber 510b during a first and second phase of operation by limiting the rearward extension of the plunger body 160 during these phases (see FIG. 2B). As such, the variable stops 142 extend different distances depending upon the concentration to which the stop 142 corresponds. For example, a concentration of 21 percent extends downwardly a lesser distance than a concentration of 20 percent thereby allowing the mixing chamber 510b to hold a larger amount of the first gas. The end of the third phase of operation (FIG. 2C) prior to the addition of filtered ambient air during the fourth phase (FIG. 2D). As such, when a concentration of 21 percent is chosen, the plunger body 160 can be allowed to extend rearwardly a greater distance thereby allowing a greater expansion of the mixing chamber 510b during the first phase of operation. Therefore, as should be apparent, the variable stops 142 are used to control the first expansion volume of the first phase of operation.

On both sides of slots 138 are slot 138 which extend inward from an inner surface of the channel 134. In some embodiments, the slot 138 extend inwardly from the inner surface of the channel 134 a greater distance than the variable stops 142. The slot 138 can be configured to prevent the apparatus 10b from switching to a different concentration value once the apparatus 10b has been activated. This can be particularly important in applications where a specific concentration of gas can be necessary and any minor change in this value can have significantly adverse effects. In the illustrated embodiment, the slot 138 are configured to substantially reduce the likelihood that the plunger body 160 will rotate to a different variable stop 142 during at least the first two phases of operation. In certain embodiments, these rails can be removed if a constantly variable metering device is desired. In such an embodiment, the variable stop 142 could instead have a ramp shape rather than have multiple steps.

Metering body 122 can additionally include a ratchet pawl 144 along an inner surface of channel 134 which extends inwardly toward the center of the channel 134. The ratchet pawl 144 can be hinged and configured such that the ratchet pawl 144 is movably deformable and provides resistance during deformation. This ratchet pawl 144 can correspond to features located on the plunger body 160 to facilitate proper orientation with respect to the selected concentration. Such a mechanism can additionally provide tactile feedback to a user of the device indicating that the proper alignment has been achieved. This tactile feedback can advantageously reduce the likelihood of activation in an improper orientation. Other types of feedback mechanisms and alignment mechanisms can also be used.

Figure 6:
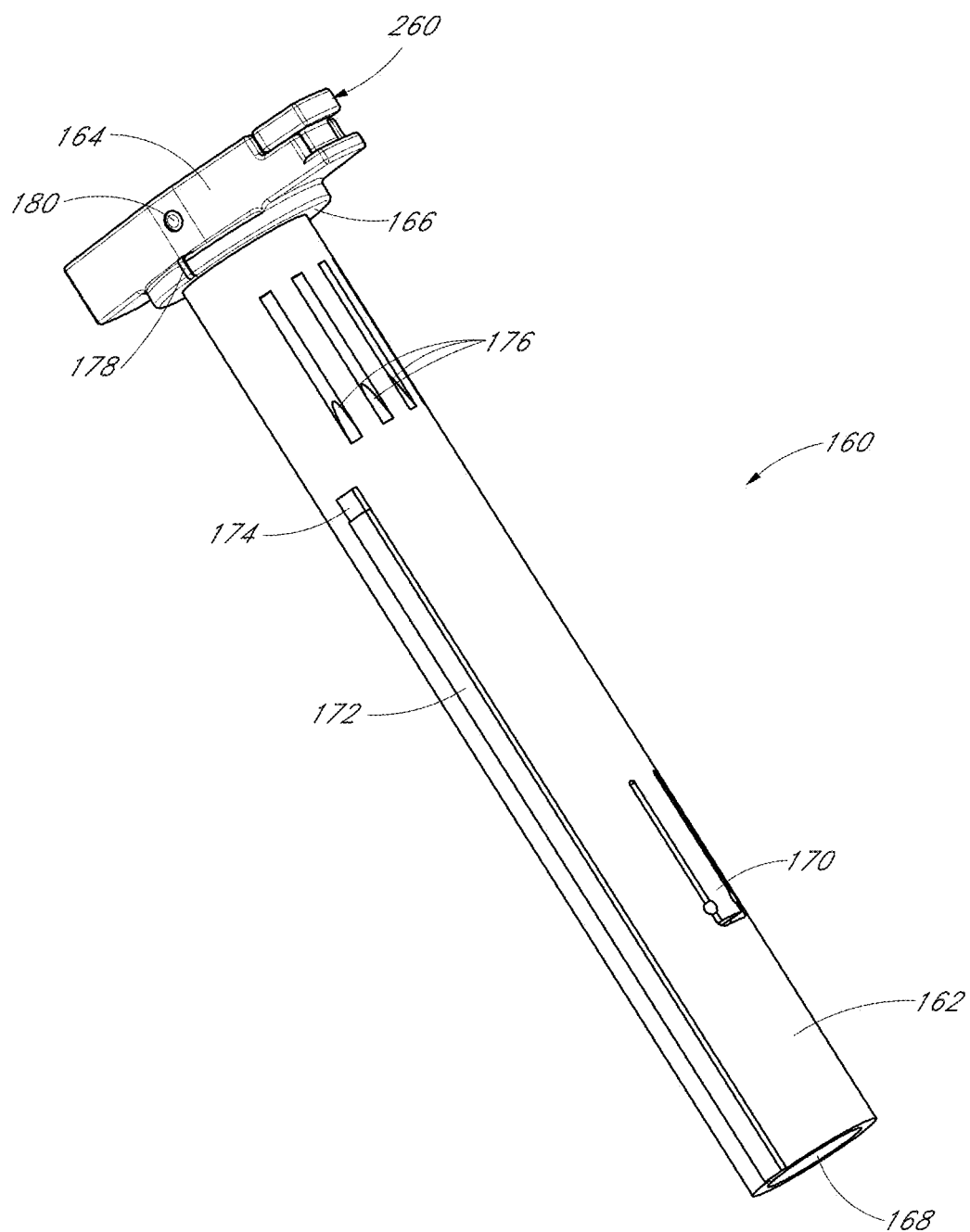
FIG. 6 is a perspective view of a plunger body of the measurement control system of FIG. 4.

With reference to FIG. 6, an embodiment of a plunger body 160 is shown which comprises a generally tubular frame 162, a handle 164 at one end of the plunger body 160, a selector ring 166 located therebetween, and a channel 168 centered on the tubular frame 162 and running throughout the entire length of the plunger body 160. The tubular frame 162 is configured to be slidably translatable and partially slidably rotatable within the channel 134 of the metering dial 120.

The tubular frame 162 has a retention mechanism 170 in the form of a clip which is hingedly attached to the tubular frame 162. The retention mechanism 170 can be configured to retain a component such as a housing 420 of the pressurized chamber 410b. The retention mechanism 170 advantageously allows the component to be attached without the use of tools thereby facilitating the process of assembling the entire device. Additionally, the retention mechanism 170 can also be configured such that the component can be removed from the tubular frame 162 thereby allowing the apparatus 10b to be reused or, in other embodiments which allow for reuse of the apparatus 10b, facilitating the process of resterilization if such a process is used for the device. Other types of retention mechanisms can also be used in lieu of the clips shown in the illustrated embodiment and can include fasteners such as screws.

Tubular frame 162 can additionally comprise a guide 172 which extends outward from the outer surface of the tubular frame 162. The guide 172 can run from the bottom end of the tubular frame 162 to a distance toward the top end of the tubular frame 162. The guide 172 is configured to fit within the slots 138 and slot 138 located along the inner surface of the channel 134 of the metering body 122. As such, the guide 172, when positioned between the slot 138, can prevent the plunger body 160 from rotating. This advantageously can prevent the plunger body 160 from moving to a different variable stop 142 after commencing the first phase of operation and thereby reduce the risk of an improper concentration in the injectable volume. The guide 172 is preferably sized such that, when the plunger body 160 is fully inserted, the guide 172 is only slightly below the slot 138 such that the plunger body 160 can rotate freely to different concentration values during the initial phase of operation (see FIG. 2A). However, because the guide 172 is only slightly below the slot 138, once extended a short distance, the guide 172 can become locked within the selected rail 140. This positioning advantageously allows the guide 172 to lock shortly after activation of the apparatus 10b. Furthermore, the guide 172 preferably extends outward from the tubular frame 162 only a sufficient distance such that it can contact the slot 138 but not enough such that it contacts the variable stops 142 located between the slot 138. This can therefore allow the guide 172 to not be interfered by the variable stops 142 during operation.

Tubular frame 162 can additionally comprise a latch aperture 174 configured to allow a latch 228 (FIG. 7) located on the activation rod 220 to protrude outward from the tubular frame 162. The latch aperture 174 is preferably centered just above the top-most portion of the guide 172. As will be discussed in detail below, in a first or "closed" position, the latch 228 is retracted such that it does not extend beyond the guide 172 and thus would not contact a variable stop 142 (see FIG. 8A). When in a second position, the latch 228 extends outwardly from the tubular frame 162 beyond the guide 172 such that the latch 228 can contact the variable stops 140 such as the lower surfaces 142a thereby preventing further extension of the plunger body 160 while the latch is in the second position (see FIG. 8B). As such, the volume to which the chamber 510b can expand is limited by the latch 228 and the surface 142a. In some embodiments, the latch aperture 174 can be placed such that, if the plunger body 160 is improperly oriented within the metering dial 120 during an initial phase of operation (shown in FIG. 2A), the latch 228 can be prevented from extending outward into the second or "open" position by a rail 140 of the metering dial 120. This can advantageously prevent the apparatus 10b from activating when improperly oriented.

Tubular frame 162 can additionally include ratchet slots 176 in the form of cut-outs located along its outer surface. The ratchet slots 176 are configured to receive the ratchet pawl 144 of the metering body 122 thereby providing a mechanism for ensuring that the plunger body 160 is properly oriented within the metering body 122 by providing resistance against rotation when the pawl 144 is received within one of the ratchet slots 176. Furthermore, advantageously, at each point where the ratchet pawl 144 is received within the ratchet slots 176, a user of the apparatus 10b can also receive tactile feedback when the plunger body 160 is properly oriented within the metering body 120.

With continued reference to FIG. 6, ring 166 can include an annular protrusion extending from the outer surface of the tubular frame 162. The selector ring 166 can additionally include a selector indicator 178 which can take the form of a minor protrusion located on the selector ring 166. Selector indicator 178 can correspond to and be alignable with the metering indicators 136 located on the metering body 122 (FIG. 5A) to indicate the concentration level that will be obtained when the plunger body 160 is oriented in that position which corresponds to the alignment of the latch 228 with a corresponding surface 142a. Such a system can advantageously provide a user of the device with easily viewed information regarding the selected concentration level. The selector indicator 178 can advantageously be colored to facilitate use of the apparatus 10b.

The handle 164 can extend in a radial direction relative to the longitudinal axis of the tubular frame 162. Handle 164 can be shaped such that a user of the apparatus 10b can grasp the handle 164 and use the handle to either further extend the plunger body 160 rearward and out of the apparatus 10b or further depress the plunger body 160 frontward into the apparatus 10b. Handle 164 can additionally include an aperture 180 for receiving a coupling mechanism for the activation switch 260. The activation switch 260 can thereby rotate about the coupling mechanism in order to operate the actuation rod 220 located within the plunger body 160.

Figure 7:
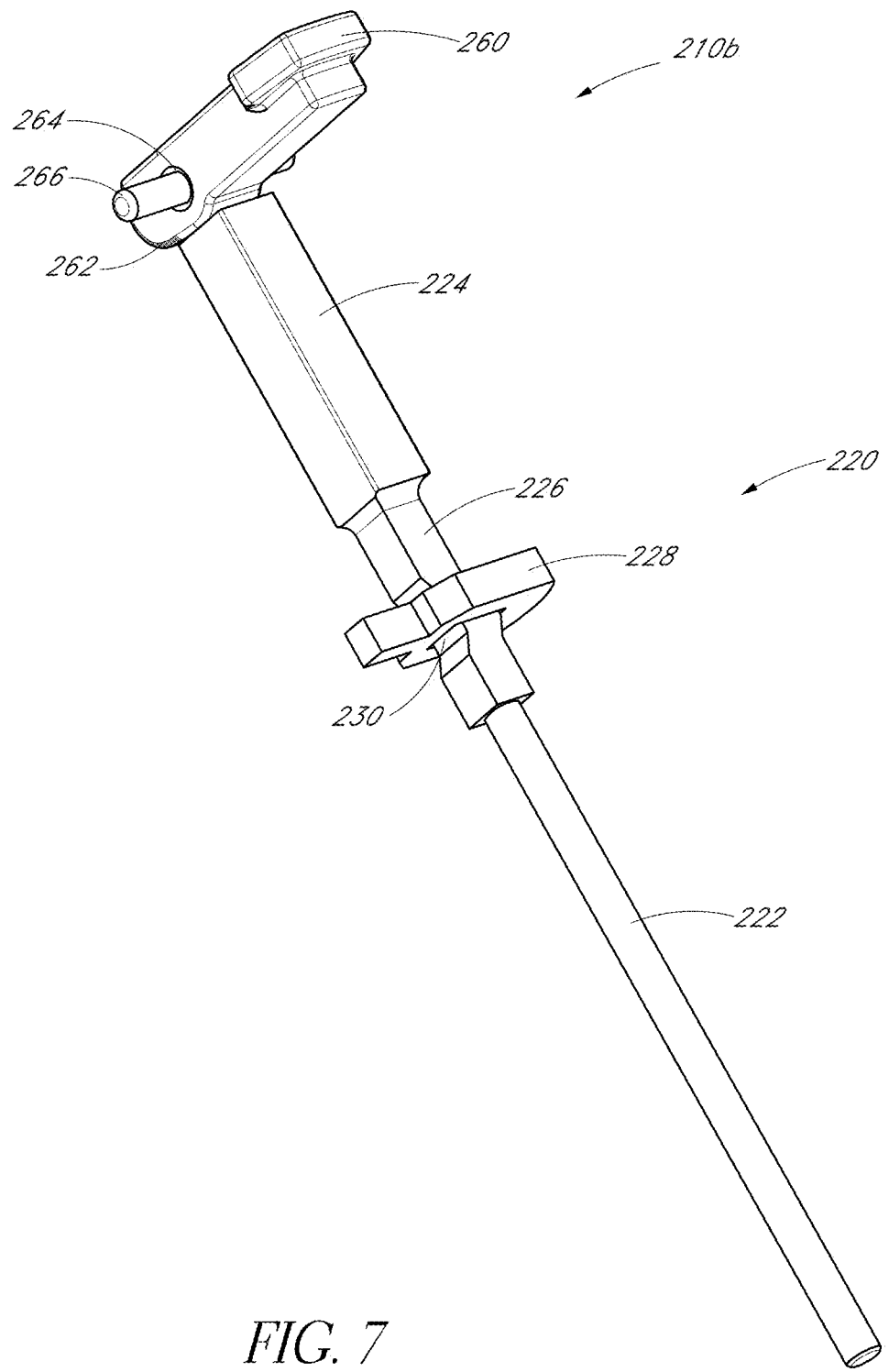
FIG. 7 is a perspective view of the activation system of FIG. 4.

With reference to FIG. 7, an embodiment of an activation system 210b is shown which comprises an actuation rod assembly 220 and an activation switch 260. The actuation rod assembly 220 has a generally elongate body with an actuator pin 222 at a first end, an actuator stem 224 at a second end, and a latch movement portion 226 located in an intermediate portion. The actuator pin 222 is configured to be received within a housing 420 of the pressurized chamber 410b and activate the release of gas contained therein when in a second or "open" position.

The actuator stem 224 is configured to abut and follow the contoured surface 262 (FIG. 9) of the activator switch 260. The actuator stem 224 is also preferably shaped such that the cross-sectional profile matches the cross-sectional profile in a top portion of the channel 169 (as shown in FIG. 8) located near the handle 164 of the plunger body 160. Preferably, the cross-sectional profile is not substantially circular such that the actuator rod 220 is substantially prevented from rotating within the channel 168 of the plunger body 160. The latch movement portion 226 is shaped such that the latch 228 is translated when the latch 228 slidably translates along the latch movement portion 226 of the actuation rod 220. As such, the latch 228 has an aperture 230 which has a cross-sectional shape similar to that of the cross-sectional shape of the latch movement portion 226.

The activator switch 260 is configured to translate the actuator rod 220 through portions of the plunger body 160 and through the housing 420 of the pressurized chamber 410b to activate the release of gas contained therein. As such, the activator switch 260 can include a cam with a contoured profile 262 along the surface configured to contact the actuator stem 224. Activator switch 260 can also have an aperture 264 configured to receive a pin 266 such that the activator switch 260 can rotate about the pin 266. In the illustrated embodiment, the activator switch 260 is shown in a first or "closed" position. In this first position, the distance between the pin 266 and the contoured surface 262 in contact with the actuator stem can be a reduced distance such that the actuator rod remains in a first or "closed" position.

When rotated about the pin 266 to a second or "open" position, the distance between the pin 266 and the contoured surface 262 in contact with the actuator stem 224 is increased distance thereby translating the actuator rod 220 to a second or "open" position further into the housing 420 of the pressurized chamber 410b. As will be described below in greater detail with respect to FIGS. 10 and 11, movement into the second or "open" position can be configured to release gas in the pressurized chamber 410b. The activator switch 260 can preferably be any type of switch that can remain in a first or second position without the user needing to maintain the switch in that position. In the illustrated embodiment, a rotating lever is used. Other switches can also be used such as a screw, latch, spring loaded pin, or any other switch known in the art.

Figure 8A:
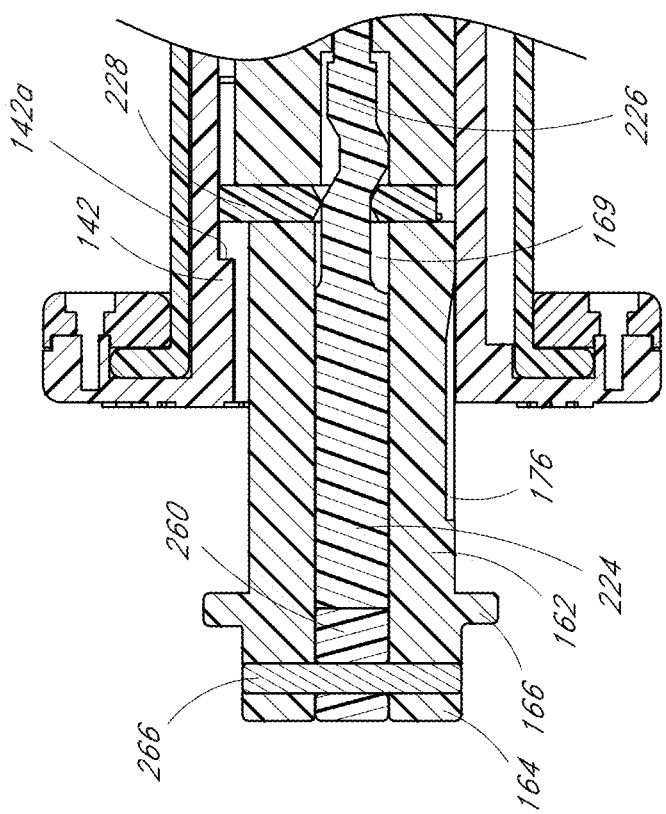
FIG. 8A is a sectional view of the measurement control system and activation system of FIG. 4 in a first or "closed" position.
Figure 8B:
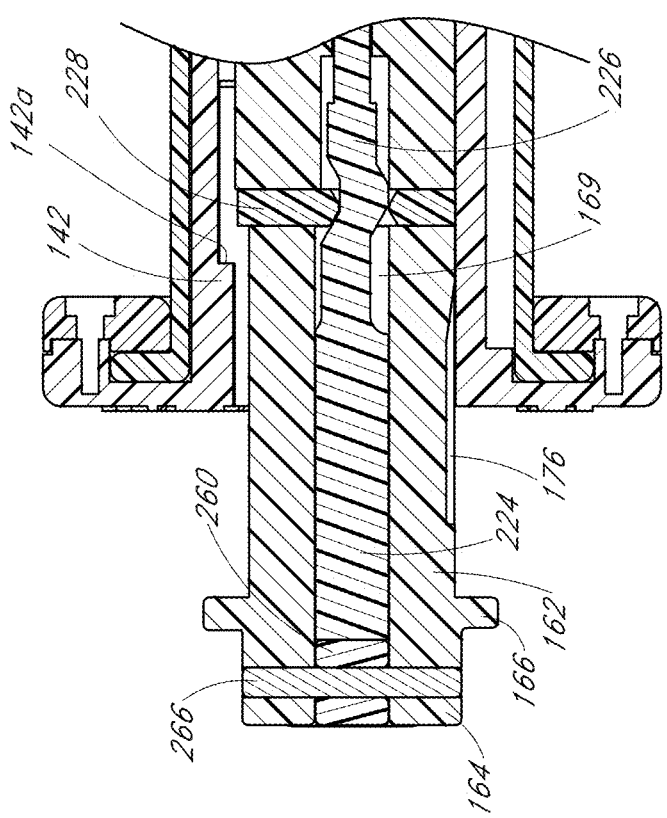
FIG. 8B is a sectional view of the measurement control system and activation system of FIG. 4 in a second or "open" position.

With reference to FIGS. 8A and 8B, an illustration of the operation of the activation system 210b is shown which includes some components of the measurement control system 110b and the activation system 210b. As shown here, the latch 228 is contained within the latch aperture 174 such that the latch cannot translate toward a front end or rear end of the plunger body 160. As such, when the actuator rod 220 translates in a frontward or rearward direction, the latch 228 must follow the profile of the latch movement portion 226 of the actuator rod 220. As such, this provides the advantage of coupling movement of the latch 228 in the second position when the activator switch 260 and thus the actuator rod 220 are in a corresponding second position. Furthermore, because movement of the latch 228 is coupled with movement of the other activator switch 260 and actuator rod 220, if the latch 228 is prevented from moving into the second position, the activator switch 260 and activator rod 220 are also prevented from moving into the second position. Note that, as described above, while in the second or "open" position, the latch 228 can protrude from the plunger body 160 thereby restricting extension of the plunger body 160 as shown in FIG. 8B.

Pressurized Chamber and First Pressure Regulation System

Figure 9:
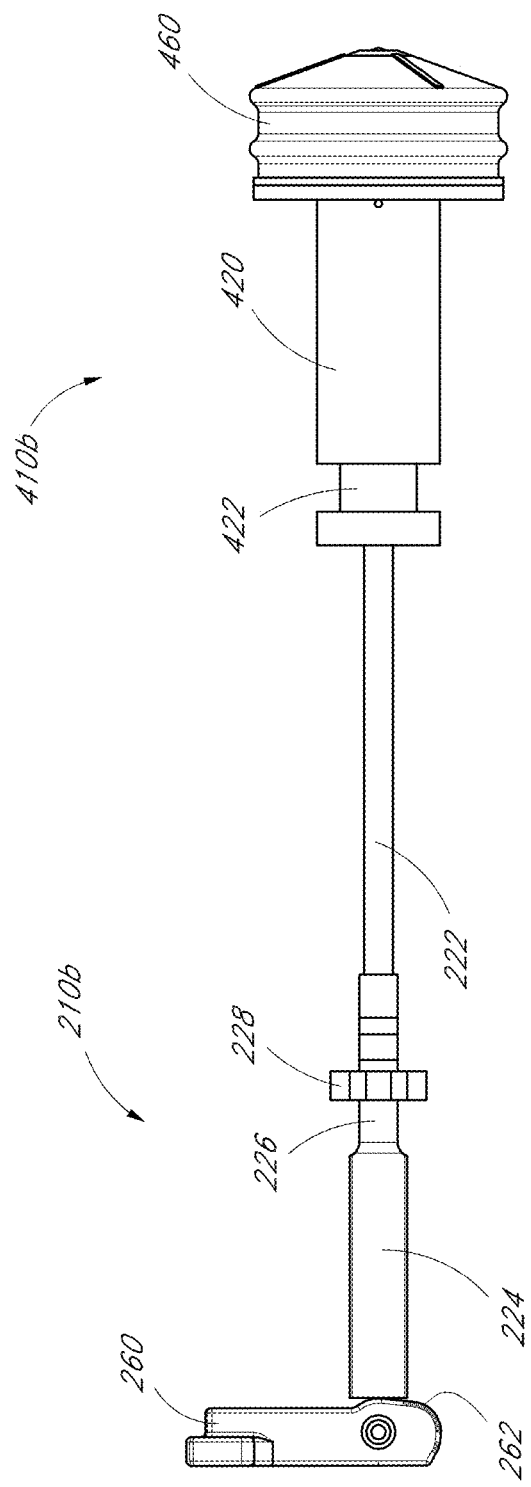
FIG. 9 is a side view of an embodiment of an activation system, pressurized chamber, and first pressure regulation system of the second embodiment of a gas mixture apparatus.

With reference to FIG. 9, an embodiment is shown including some components of both the activation system 210b, the pressurized chamber 410b of the mixing system 310b, and the first pressure regulation system 610b of the mixing system 310b. As illustrated, the pressurized chamber 410b can have a housing 420 with an annular slot 422 located near a first end of the housing 420. The annular slot 422 can be configured to receive the retention mechanism 170 located on the plunger body 160. Housing 420 can also have a plunger seal 460 located at a second end of the housing 420. The plunger seal 460 is configured to provide an airtight seal for defining the mixing chamber 510b.

Figure 10:
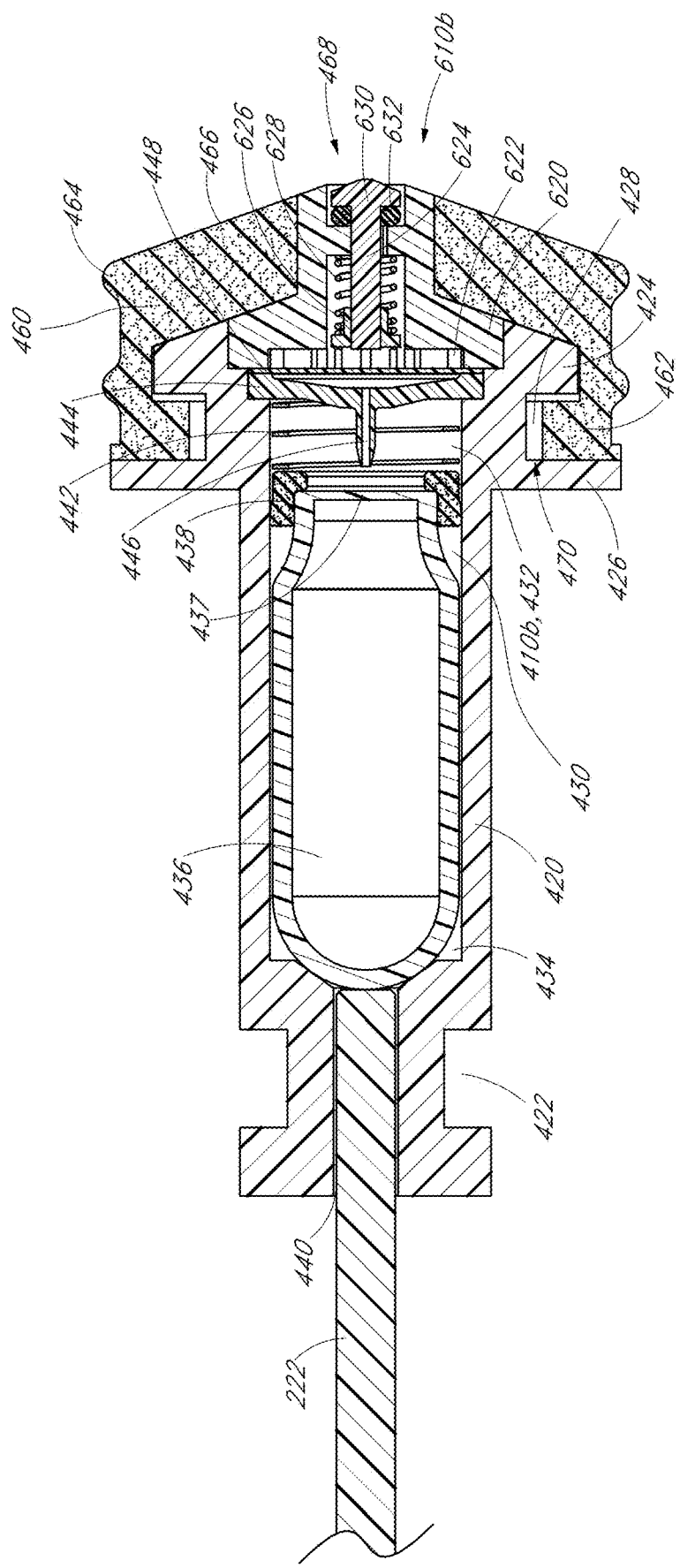
FIG. 10 is a sectional view of the activation system, pressurized chamber, and first pressure regulation system of FIG. 9 in a first position.

With reference to FIG. 10, which is a sectional view of the pressurized chamber 410b and the first pressure regulation system 610b. The annular slot 422 is located at the first or rearward end and a conical or frusto-conical surface 424 located at the second or frontward end corresponding to the shape of the plunger seal 460. Housing 420 can additionally be shaped such that it has an annular protrusion 426 and an annular slot 428 configured to receive a lip 462 of the plunger seal 460. This configuration advantageously ensures that the plunger seal 460 remains connected to the housing 420 and forms a seal to prevent the leakage of any gas contained in the housing body 420. Lip 462 of the plunger seal 460 can fit snugly within the annular slot 428 of the housing 420 to provide an enhanced seal.

An interior space 430 is substantially enclosed by the housing 420 and can be separated into a first separate portion 432 and a second separate portion 434. Contained within the second separate portion 434 of the housing 420 can be a third separate portion in the form of a structural unit such as a canister 436. This canister can contain the gases for mixing into the mixing chamber 510b. Provision of the gases in a canister is advantageous as it facilitates manufacturing of the apparatus 10b as it can allow the canisters to be manufactured separately from other components of the pressurized chamber 410b. In some embodiments where the apparatus 10b is reusable, canisters can be replaced.

The canister 436 has a first or rearward end in contact with the actuator pin 222 and a sealed second or frontward end 437. At one end of the canister 436 is a seal 438 which substantially reduces leakage of any gas from the first separate portion 432 to the second separate portion 434. This advantageously reduces the likelihood of gases from leaking out of the actuator aperture 440 and out of the apparatus 10b.

The housing 420 can also include a biasing mechanism 442, such as a spring, which exerts a force on the seal in a direction away from the second end of the housing 420. In the illustrated embodiment, the biasing mechanism 442 is located in the first separate portion 432. This reduces the likelihood of the canister 436 moving into the first separate portion 432 and potentially releasing the gas contained therein without having been activated by the user. Furthermore, biasing mechanism 442 can also provide a counterforce against activation such that a user cannot accidentally activate the device. The biasing mechanism 442 can be configured to exert a sufficient force such that, after the first and second phases of operation are complete and the activation switch 160 is returned to a first or "closed" position, the biasing mechanism 442 exerts sufficient force such that actuator rod 220 is returned to its first or "closed" position thereby causing the latch 228 to return to its first or "closed" position. Once latch 228 returns to its first or "closed" position, the extension of the plunger body 160 is no longer limited and the third phase of operation can commence. If the biasing mechanism 442 does not exert sufficient force on the actuator rod 220, entering into the third phase of operation could be more difficult.

Housing 420 can also have a release mechanism 444, such as a needle or a pilot tip as illustrated in this embodiment of the apparatus 10b, which can be configured to puncture the sealed second end 437 of the canister 436 to release gas into the first separate portion 432 through the release mechanism 444 due to a channel 446 running axially through release mechanism 444. Due to the high pressure in the first separate portion 432, the first pressure regulation system 610b can open allowing the gas to escape to the front of the plunger seal 460 and into the mixing chamber 510b. In some embodiments, a filter 448 can be placed along the flow path such that there is a reduced likelihood of foreign materials entering into the mixing chamber 510b. In some embodiments, the filter 448 can be configured to filter out bacteria.

Plunger seal 460 is configured to partially define the injectable volume of the mixing chamber 510b by creating a seal for the mixing chamber 510b. Plunger seal 460 can have a generally cylindrical body with annular protrusions 464 configured to contact an inner surface of the mixing chamber 510b and a conical or frustoconical face 466 at a frontward end. The frustoconical face 466 can additionally comprise an aperture 468 centered about the cylindrical body configured to receive components of the first pressure regulation system 610b. Furthermore, the body can also have an opening 470, defined by the lip 462, on the rearward end configured to receive the housing 420.

With continued reference to FIG. 10, an embodiment of the first pressure regulation system 610b is shown in a first or "closed" position. The first pressure regulation system 610b can comprise a valve body 620 comprising multiple apertures 622 at one end, a valve stem 624 running through the valve body 620 with a seat 626 at a rear end configured to contact the biasing mechanism 628 and a head 630 at a front end configured to contact a sealing ring 632.

During operation, the biasing mechanism 628 can exert a biasing force against the seat 626 in a rearward direction such that the head 630 is biased against the sealing ring 632 and valve body 620 thereby reducing or preventing the flow of gas through the valve body 620 and ultimately into the mixing chamber 510b. Due to the orientation of the biasing mechanism 628, the first pressure regulation system 610b remains closed until pressure within the pressurized chamber 410b exceeds a threshold value. This threshold value can be configured by changing the amount of force necessary to compress the biasing mechanism 628.

Figure 11:
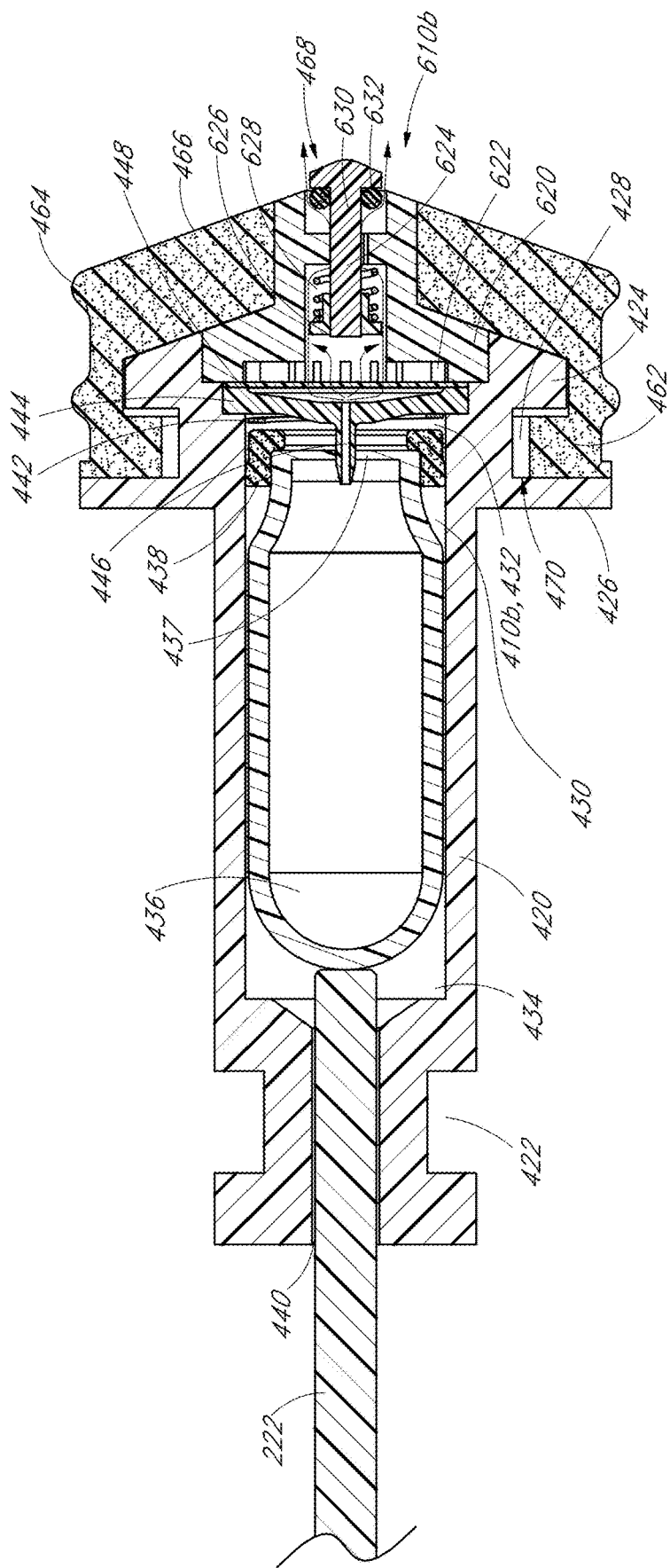
FIG. 11 is a sectional view of the activation system, pressurized chamber, and first pressure regulation system of FIG. 9 in a second position.

With reference to FIG. 11, an embodiment of the first pressure regulation system 610b is shown in an "open" position in which pressure within the pressurized chamber 410b exceeds the pressure within the mixing chamber 510b. In some preferred embodiments, the difference in pressure is substantial. Due to this pressure differential, sufficient force is placed upon the valve components causing the biasing mechanism 628 to be overcome thereby allowing gas to flow out of the valve body 620 and into the mixing chamber 510b.

This configuration for the first pressure regulation system 610b is advantageous due to the multiple phases of operation of the apparatus 10b. During the first and at least part of the second phase of operation, the pressure differential causes the valve to remain open. However, once the pressure differential is insufficient to overcome the threshold value, the valve remains in a closed position preventing any additional gas from flowing into the mixing chamber and potentially disrupting the calculated pressures/concentrations.

Figure 12:
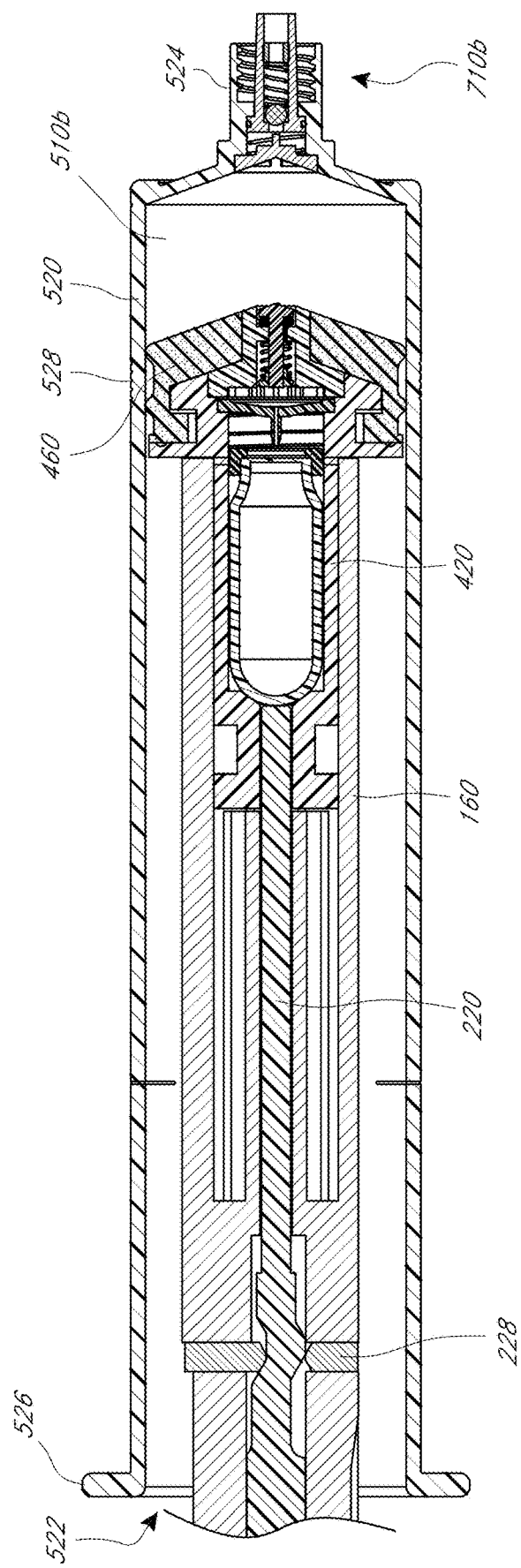
FIG. 12 is a sectional view of components including a mixing chamber and second pressure regulation system of the gas mixture apparatus.

With reference to FIG. 12, an embodiment of a mixing chamber 510b is shown comprising a syringe body 520, a second pressure regulation system 710b, and various components of the above-mentioned systems. Syringe body 520 can be a cylindrical body, and can include an aperture 522 at the rear end, and a threaded nozzle 524 at the front end. Syringe body also has flange 526 configured to be engaged with the metering device 120. The mixing chamber 510b can be defined by the inner walls of the syringe body 520 and the plunger seal 460. Furthermore, the syringe body can include indicators 528 along its outer surface corresponding to a chosen concentration. These indicators 528 can advantageously provide visual confirmation to the user of a selected concentration.

Figure 13:
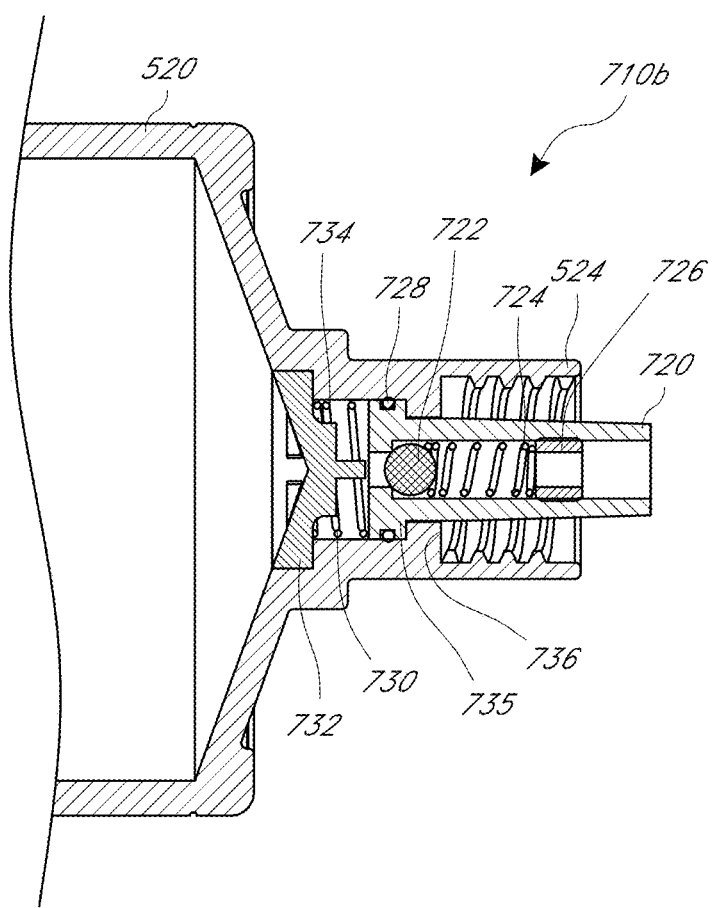
FIG. 13 is an enlarged sectional view of the mixing chamber and second pressure regulation system of FIG. 12.

With reference to FIG. 13, an embodiment of the second pressure regulation system 710b is shown comprising a valve body 720 which can include a ball 722, a biasing mechanism 724, a seat 726, and a sealing mechanism 728. The second pressure regulation system 710b can also comprise a second biasing mechanism 730 and a pin actuator 732.

The valve body 720 can be translatable within the interior space 734 near the nozzle 524 of the syringe body 520. In some embodiments, due to the second biasing mechanism 730, the valve body 720 is translated such that a flange 735 of the valve body 720 is pressed against the inner lip 736 of the nozzle 524. Furthermore, biasing mechanism 724 can seal and prevent flow through the valve body 720 until a sufficient force is placed on the ball 722 to overcome the biasing force. This can occur when the pressure differential between the mixing chamber 510b and the atmosphere is beyond a threshold value.

During operation, the second pressure regulation system 710b is opened during first and second phases of operation due to the increased pressure contained in the mixing chamber 510b. Once the pressure differential is insufficient to cause valve body 720 to open, the second phase of operation is complete and the user can move proceed to the third phase of operation.

Figure 14:
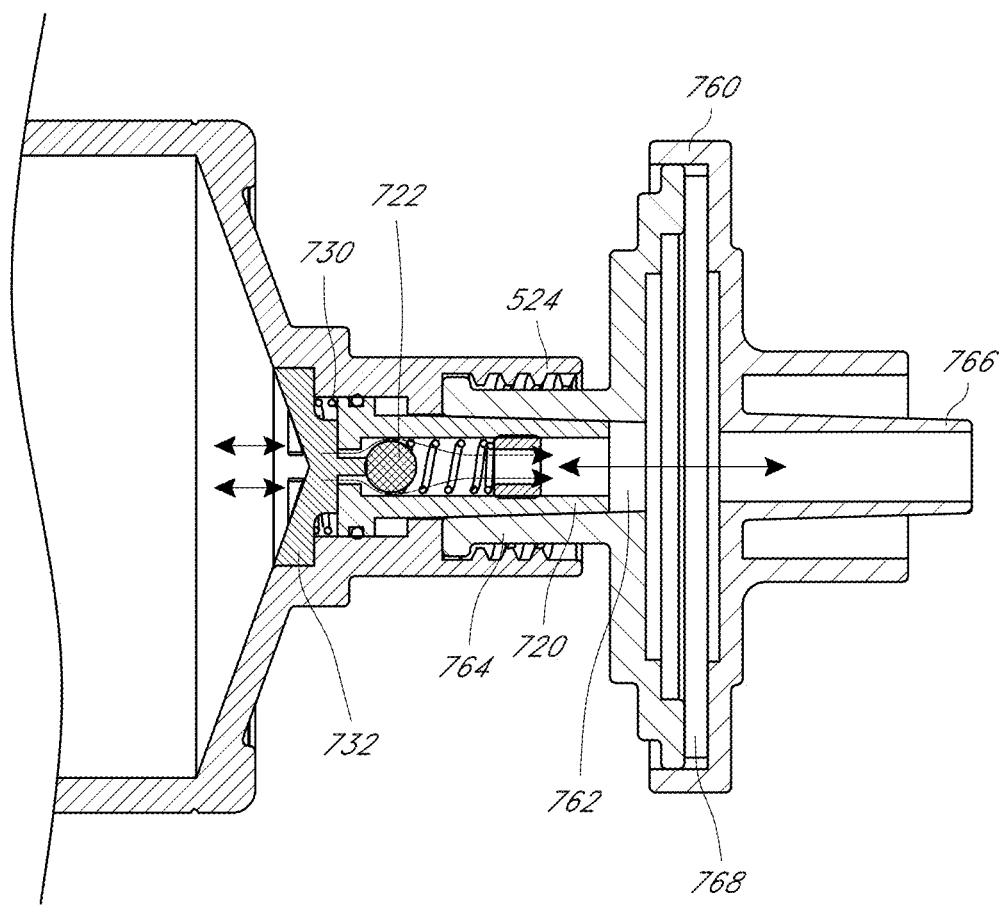
FIG. 14 is an enlarged sectional view of the mixing chamber and second pressure regulation system of FIG. 12 with an additional attachment.

With reference to FIG. 14, a filter 760 is attached to an outlet of the second pressure regulation system 710b. The filter 760 has a first open end 762 with a flange 764 configured to engage with the threads on the interior of the threaded nozzle 524, a second open end 766, and a filter element 768 located therebetween. As such, gas can pass in both directions between the first open end 762 to the second open 766 and be filtered in the process.

In some embodiments, the inner surface of the first open end 762 tapers in the direction of the second open end 766 such that the shape corresponds to the shape of valve body 720. As the attachment 760 is threaded into the threaded nozzle 524, the attachment 760 engages the valve body 720 and translates the valve body 720, against the biasing force of the second biasing mechanism 730 towards the rear end of the syringe body 520. This causes the ball 722 to contact the pin actuator 732 thereby causing the ball to move away from the inner surface of the valve body 720 to thereby allow gas to flow through the valve body 720 in either direction. This configuration can allow the mixing chamber 510b to be further expanded at ambient pressure and for filtering air drawn into the mixing chamber 510b. In this position, the third phase of operation can therefore be performed. Once the third phase of operation is completed, the filter 760 can be removed. Due to the force of the second biasing mechanism 730, the valve body 720 can be translated away from pin actuator 732 such that the valve body 720 remains closed until a user decides to use the therapeutic gas within the mixing chamber 510 by, for example, by attaching an injection needle for injection of the therapeutic gas into a patient.

Embodiment of Measurement Control System and Activation System

FIGS. 15-31 illustrate additional embodiments of components of a measurement control system of the apparatus.

Figure 15A:
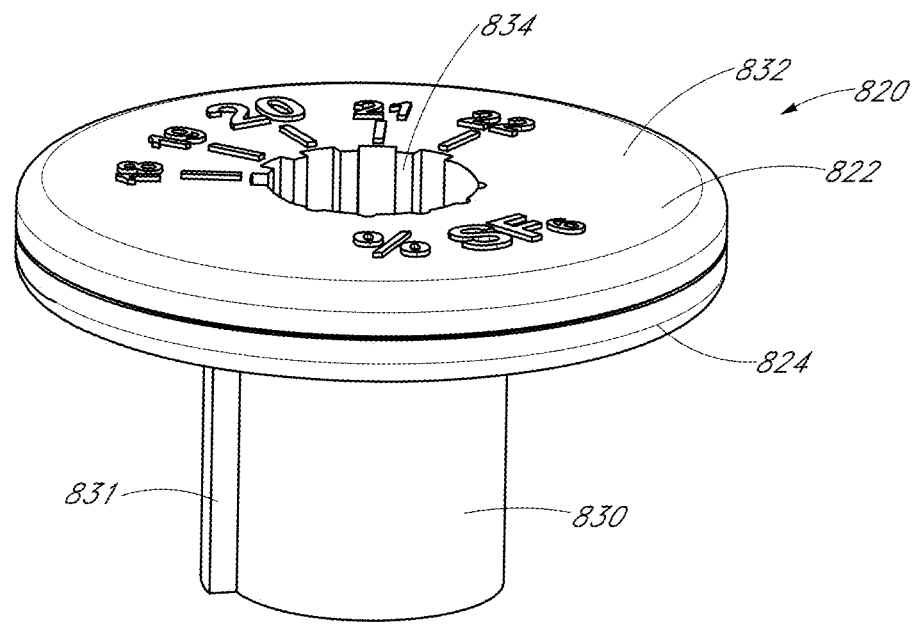
FIG. 15A is a perspective view of a metering dial of an embodiment of a measurement control system.
Figure 15B:
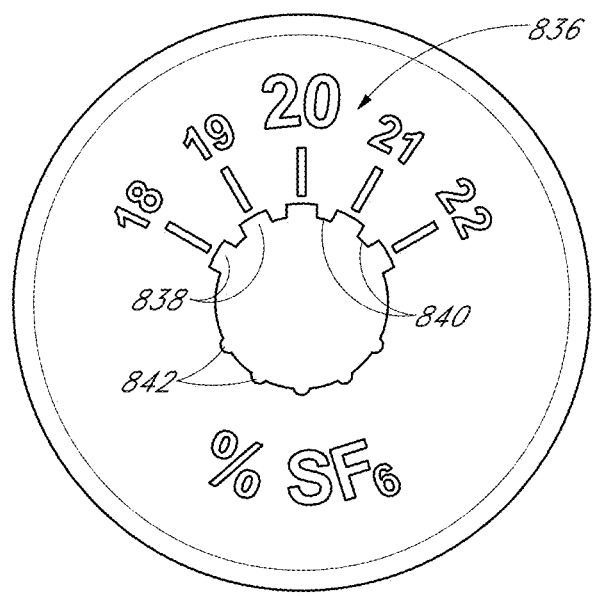
FIG. 15B is a sectional view of a metering dial of an embodiment of a measurement control system.

FIGS. 15A and 15B illustrate an embodiment of a metering dial 820 which can be configured to allow a user of the device to select a concentration of fluid for an injectable volume. Similar to other embodiments, the metering dial 820 can include two components such as a metering body 822 and a metering cap 824 which can be removably attached to the metering body 822.

With continued reference to FIG. 15A and FIG. 15B, the metering body 822 can have a generally cylindrical member 830 with a flange 832 located at top portion of the metering body 822. The metering body 822 can include a channel 834 substantially centered on the cylindrical member 830 and running throughout the entire metering body 822. In some embodiments, such as that illustrated in FIG. 15A, the generally cylindrical member 830 can include additional surface features, such as an increased diameter portion 831, which can potentially be keyed to the device into which it is inserted.

As with other embodiments of metering dials or similar metering mechanisms, this embodiment can also include metering indicators 836 located along a surface of the metering body 822. In this illustrated embodiment the metering indicators 836 are located on a top surface of the flange 832 although any other viewable location can be used such as, for example, along the perimeter portion of the flange 832. In the illustrated embodiment, the metering indicators 836 show a range of numbers from 18, 19, 20, 21, and 22 corresponding to concentrations of sulfur hexafluoride (SF6) which can be produced in an injectable volume of the assembly.

As with other embodiments of metering dials and other metering mechanisms, the metering body 822 can have slots 838, rails 840, and variable stops corresponding to the metering indicators 836.

The operation of the variable stops of the illustrated embodiment of the metering dial 820 can be similar to that of other embodiments of metering dials and metering mechanisms. The variable stops can be configured to interact with components contained within the plunger body 860, such as a latch 928 or similar protruding structure, to control expansion of a chamber for an injectable volume during at least some phases of operation. In some embodiments, the variable stops can perform this task by limiting the rearward extension of the plunger body 860 during different phases. As such, the variable stops extend different distances depending upon the concentration to which the stop corresponds.

Figure 16:
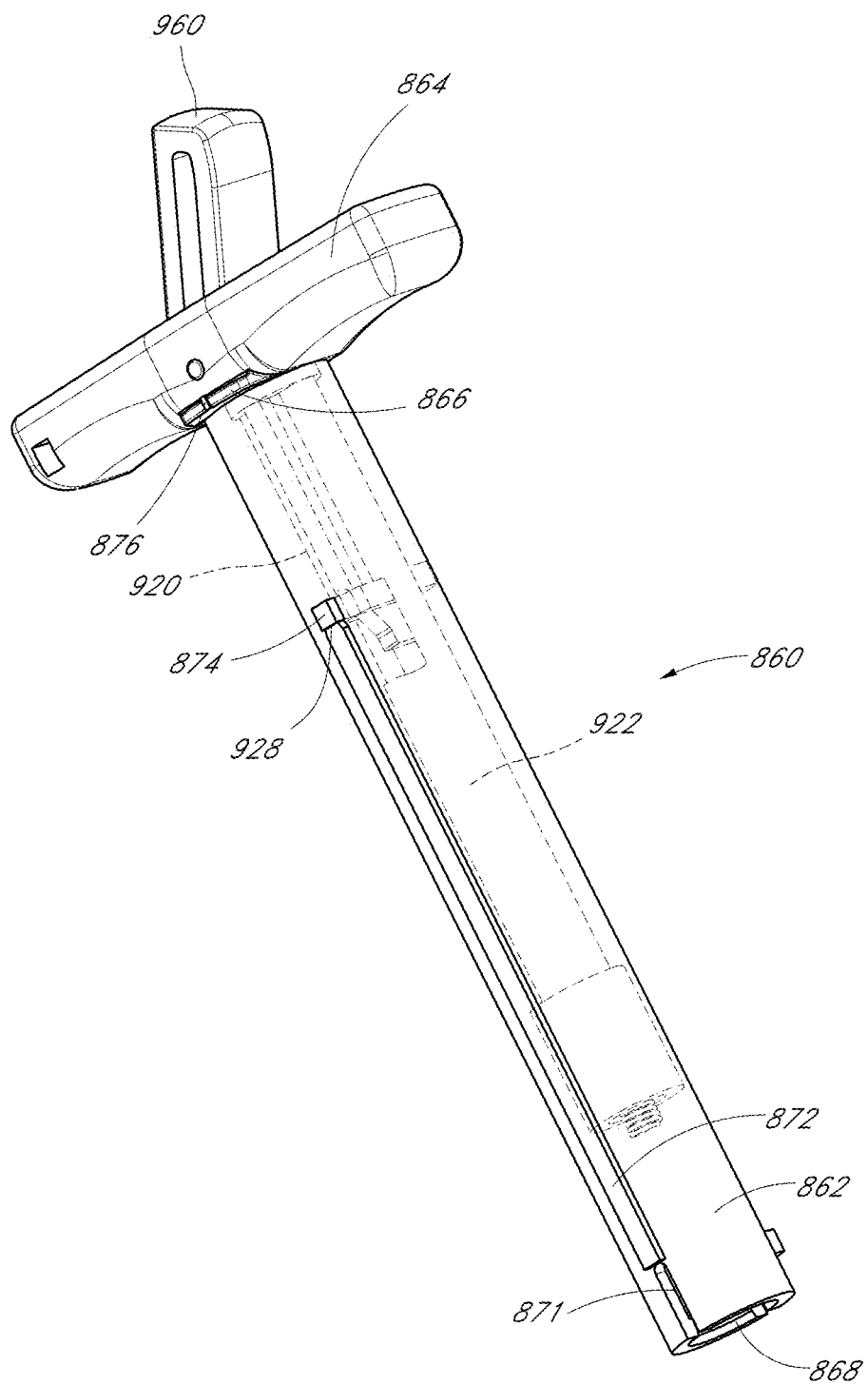
FIG. 16 is a perspective view of a plunger body of an embodiment of a measurement control system.
Figure 17:
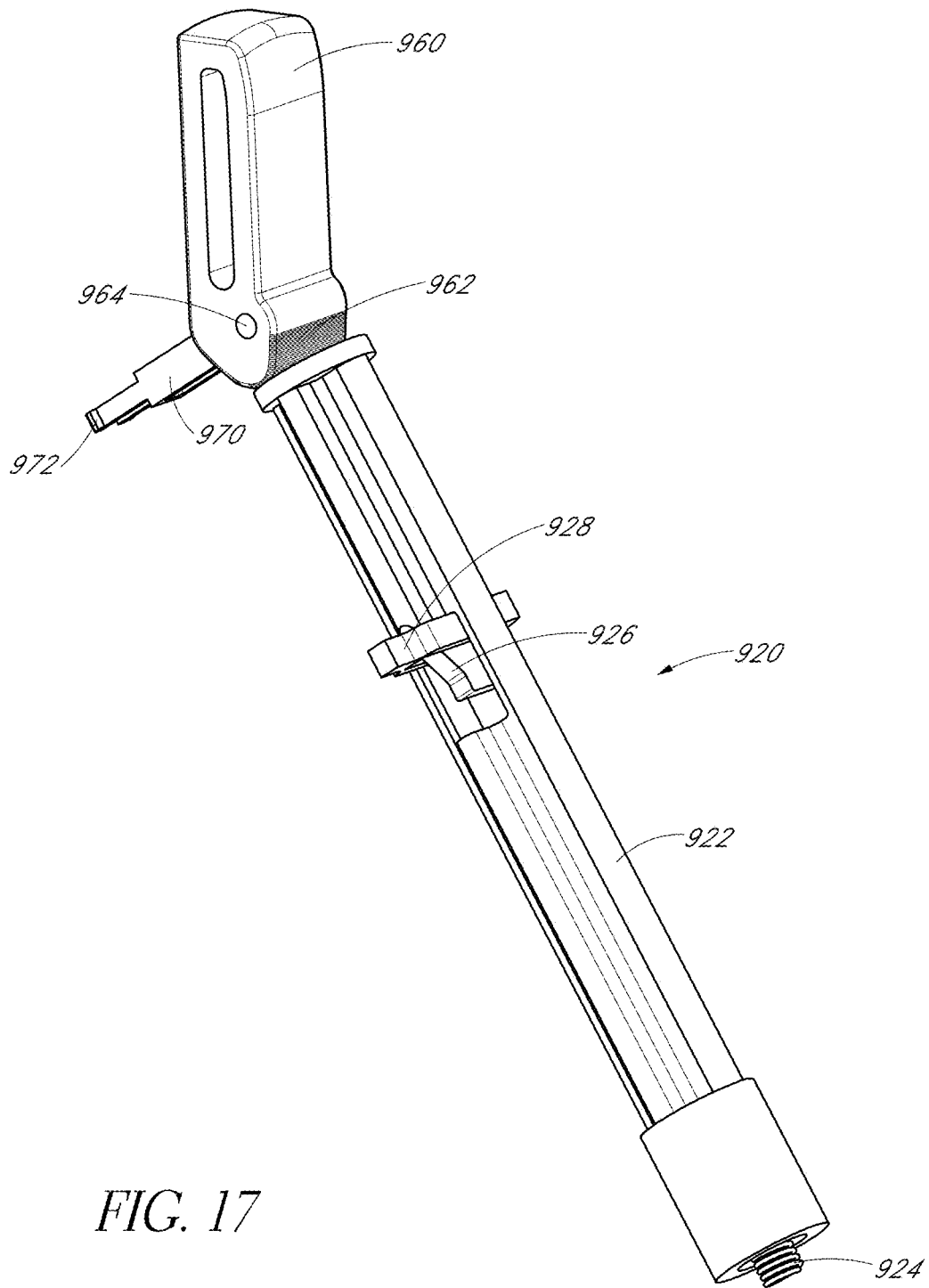
FIG. 17 is a perspective view of components of an embodiment of an activation system.

With reference to FIG. 16, an embodiment of a plunger body 860 is shown which can include a generally tubular frame 862, a handle 864 at one end of the plunger body 860, a selector member 866 located there between, and a channel 868 centered on the tubular frame 862 which can run throughout the entire length of the plunger body 860 or which can run throughout at least a part of the length of the tubular frame 862. The tubular frame 862 can be configured to slidably translate and slidably rotate within a channel of a metering dial.

With continued reference to FIG. 16, the tubular frame 862 can include a latch aperture 874 configured to allow a latch 928 located on the activation rod 920 and contained within the channel 868 to protrude outwardly from the tubular frame 862. As shown in the illustrated embodiment, the latch aperture 874 can be centered just above the topmost portion of the guard 872. In other embodiments, the latch aperture 874 can also be located at different positions along the tubular frame 862 and can contain more than one latch aperture if multiple latches are used.

As described in greater detail below, in a first, "initial", or "pre-activation" position, the latch 928 can be sized so as to not extend beyond the guard 872 and thus not contact a variable stop or similar structure. When in a second or "open" position, the latch 928 can extend outwardly from the tubular frame 862 beyond the guard 872 such that the latch 928 can contact the variable stops or similar structures thereby preventing or significantly reducing the likelihood of further extension of the plunger body 860 while the latch is in the second position.

Figure 25A:
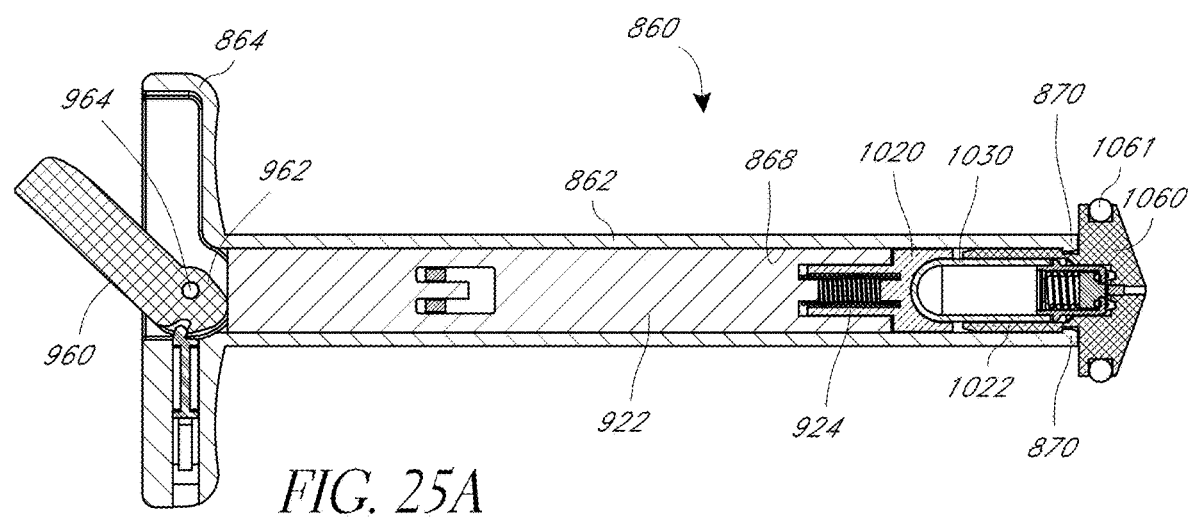
FIG. 25A is a sectional view of the embodiment of an activation system, pressurized chamber, and a storage member pressure regulation system of FIG. 24 in a first, "initial", or "pre-activation" position.
Figure 25B:
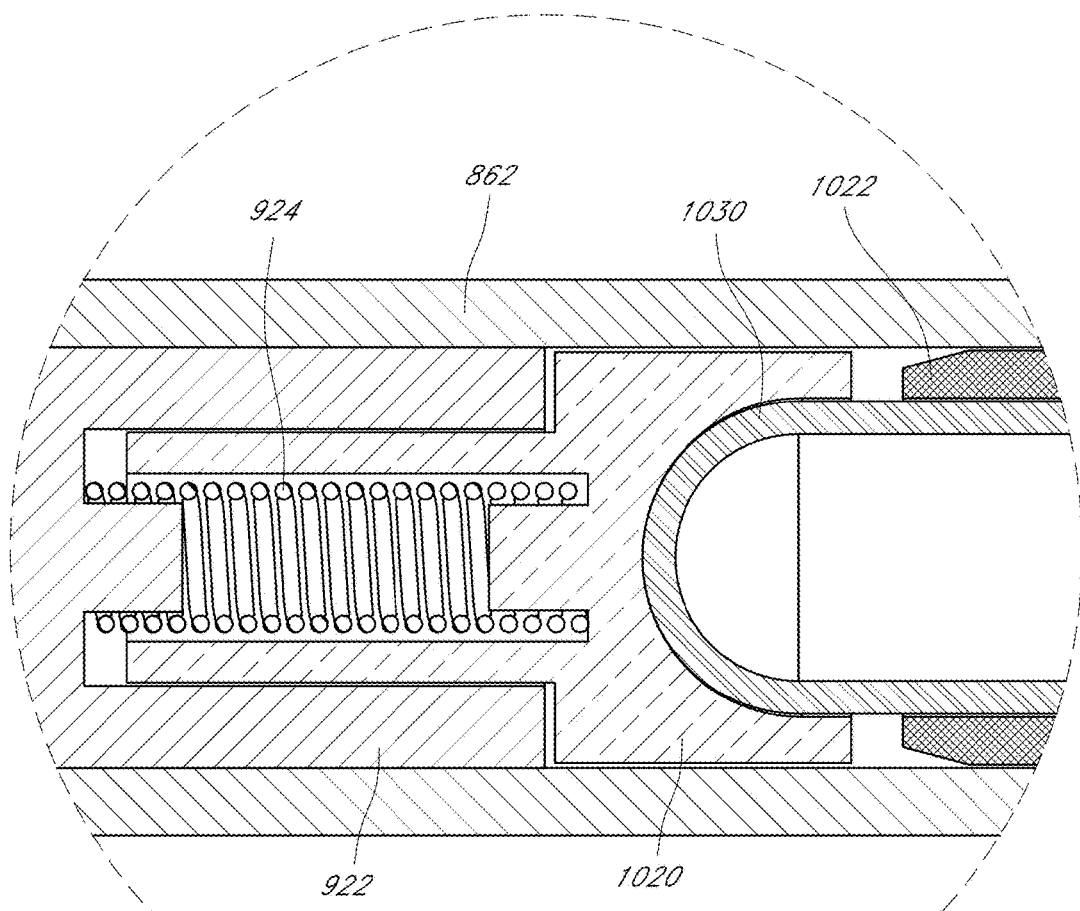
FIG. 25B is an enlarged view of the embodiment of an activation system, pressurized chamber, and a storage member pressure regulation system of FIG. 25A.

With continued reference to FIGS. 16, 25*a* and 25*b*, an activator switch 960 can be configured to translate the actuator rod 920 through the plunger body 860 towards the first housing member 1020 to activate a mechanism for releasing the gas contained therein. As such, the activator switch 960, like the activator switch of other embodiments, can be a cam with a contoured profile 962 located along the surface configured to contact the actuator body 922. Activator switch 960 can additionally include an aperture 964 configured to receive a pin such that the activator switch 960 can rotate about the pin. It should be appreciated by a person of skill in the art that the activation switch 960 can preferably be any type of switch that can remain in a first, second, or more positions without the user needing to maintain the switch in that position. In the illustrated embodiment, a rotating lever is used. Other switches can also be used such as a screw, latch, spring loaded pin, or any other switch known in the art.

Figure 18:
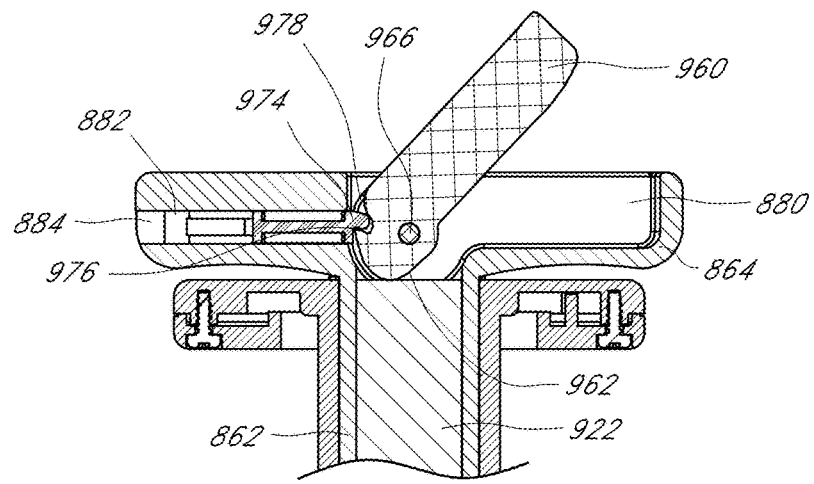
FIG. 18 is a sectional view of a measurement control system and activation system in a first, "initial", or "pre-activation" position showing operation of an interlock mechanism.

With reference to FIG. 18, the activator switch 960 is shown in a first, "initial", or "pre-activation" position. For example, this can be a position prior to a first phase of operation. In this first position, the distance between the pin 966 and the contoured surface 962 in contact with the actuator body 922 can be a first distance such that the actuator body 922 is located at a first distance from the end of the tubular frame 862 of the plunger body 860.

Figure 19:
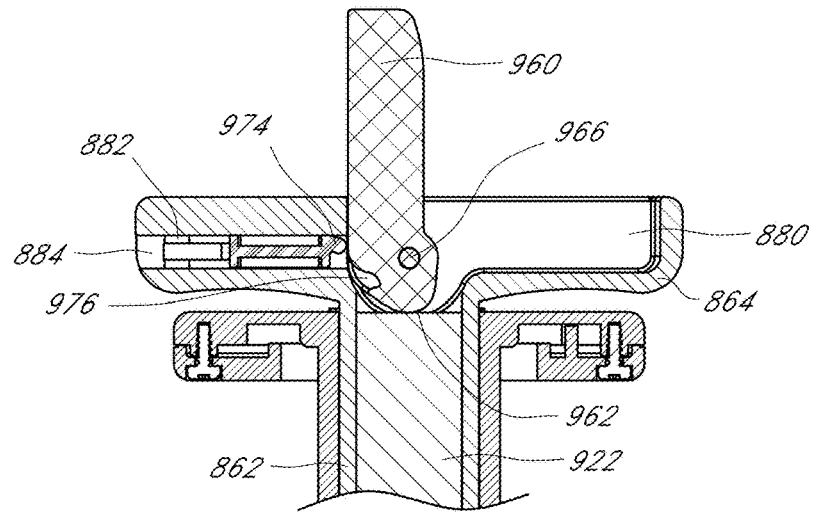
FIG. 19 is a sectional view of a measurement control system and activation system in a second or "open" position showing operation of an interlock mechanism.

As shown in FIG. 19, in some embodiments, the activator switch 960 can be rotated towards a more vertically oriented position, a second or "open" position, in which the distance from the pin 966 to the contoured surface 962 in contact with the actuator body 922 can be a second distance such that the actuator body 922 is located at a second distance from the end of the tubular frame 862 of the plunger body 860. This can correspond to the position of the activation switch 960 during a first and second phase of operation. In some embodiments, the second distance can be greater than the first distance. As will be described in more detail with respect to FIGS. 25-27, this can cause the actuator body 922 to translate towards the first housing member 1020 of the pressurized chamber. This translation can activate the release of fluid or gas contained in the pressurized chamber.

Figure 20:
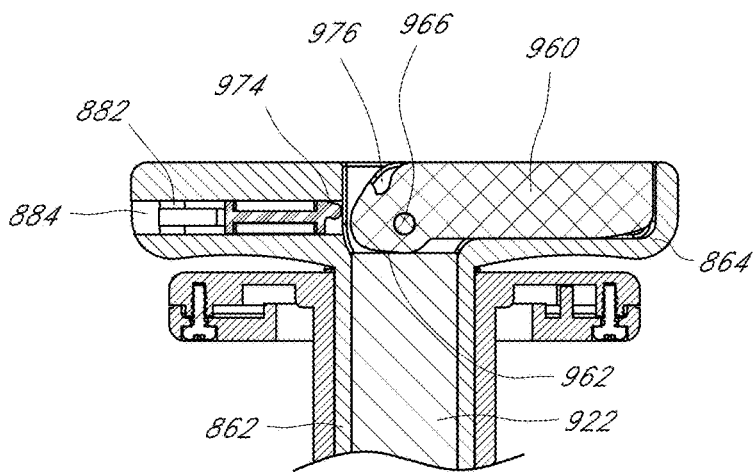
FIG. 20 is a sectional view of a measurement control system and activation system in a third or "closed" position showing operation of an interlock mechanism.

As shown in FIG. 20, in some embodiments, the activation switch 960 can also be rotated towards a more horizontally-oriented position, a third or "closed" position, in which the distance from the pin 966 to the contoured surface 962 in contact with the actuator body 922 can be a third distance such that the actuator body 922 is located at a third distance from the end of the tubular frame 862 of the plunger body 860. This can correspond to a third phase of operation and/or a final phase prior to injection of the injectable volume into a patient. This third distance can be less than or equal to the first and/or second distances. In some embodiments, rotation towards the third position can cause the actuator body 922 to translate away from the first housing member 1020 of the pressurized chamber such that no fluid or gas is released from the pressurized chamber.

Optionally, an interlock mechanism can be included to control and limit the movement of the activation switch 960.

Figure 21:
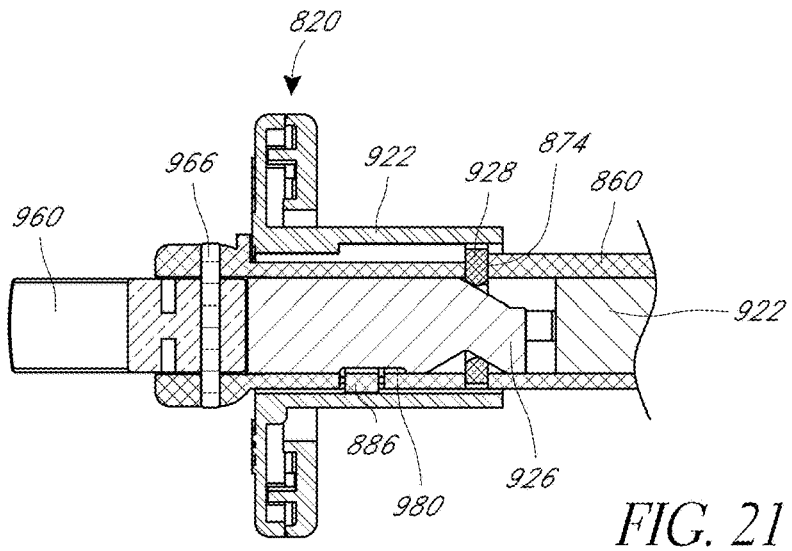
FIG. 21 is a sectional view of a measurement control system and activation system in a first, "initial", or "pre-activation" position showing operation of the latch.
Figure 22:
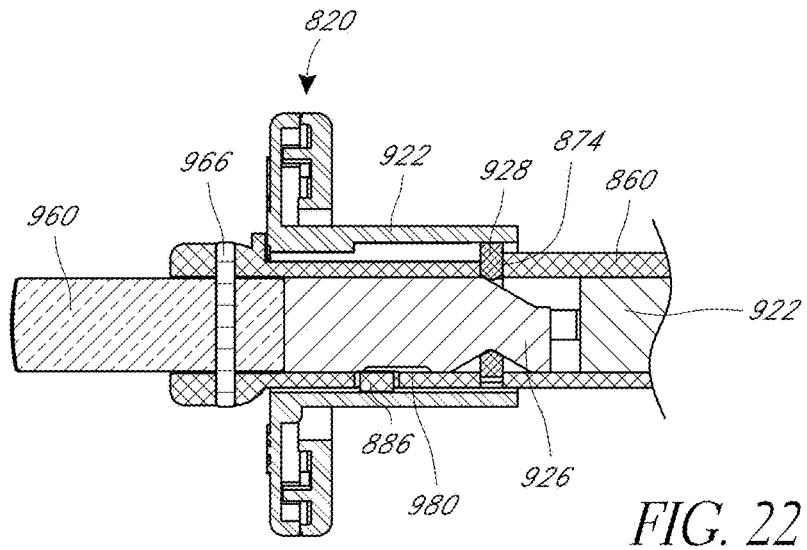
FIG. 22 is a sectional view of a measurement control system and activation system in a second or "open" position showing operation of the latch.
Figure 23:
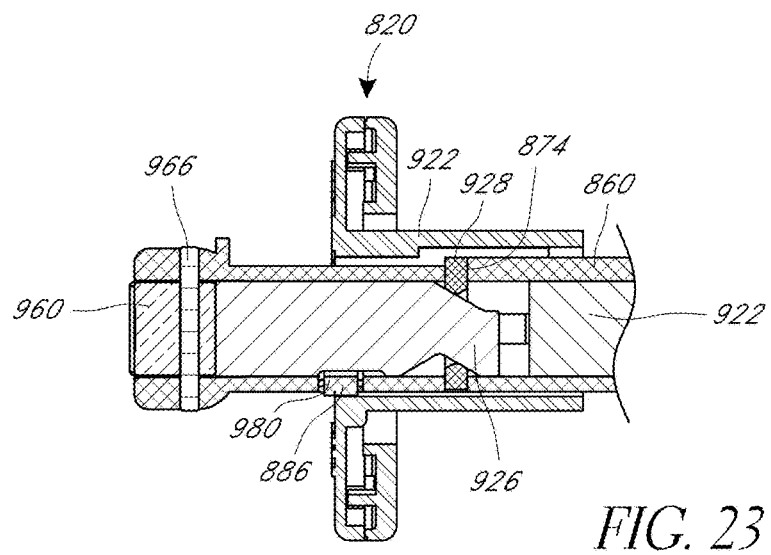
FIG. 23 is a sectional view of a measurement control system and activation system in a third or "closed" position showing operation of the latch.

With reference to FIGS. 21-23, operation of an embodiment of the activation system is shown. As shown in the illustrated embodiment, and similar to other embodiments, the latch 928 can be contained within the latch aperture 874 such that the latch cannot translate toward a front end or rear end of the plunger body 860. In such an embodiment, when the actuator rod 920 translates in a frontward or rearward direction, the latch 928 is configured to follow the profile of the latch movement portion 926 of the actuator rod 920.

FIG. 21 shows the embodiment in a first, "initial", or "pre-activation" position. As shown here, the latch 928 can be positioned such that it outwardly protrudes from the plunger body 860 sufficiently such that, if extended rearwardly, the latch 928 would contact a variable stop located on the metering body 922 and prevent any further extension. In other embodiments, when in the first position, the latch 928 can be configured so as to not outwardly protrude from the body 860 to prevent such extension. When moved to the second or "open" position, as shown in FIG. 22, the latch 928 can sufficiently outwardly protrude from the plunger body 860 such that the latch 928 can contact the variable stop or similar structure located on the metering dial 820 thereby preventing any further rearward extension. When rotated to the third or "closed" position, as illustrated in FIG. 23, the latch 928 can be sufficiently retracted within the latch aperture 874 such that the latch 928 no longer contacts the variable stop or similar structure located on the metering dial 820 thereby allowing the plunger body 860 to be further extended rearwardly.

With continued reference to FIGS. 21-23, a ratcheting member 886 such as a pawl can be attached to the plunger body 860. The ratcheting member 886 can be hinged and configured such that the ratcheting member 886 is movably deformable and provides resistance during deformation. The ratcheting member 886 can correspond to features located on the plunger body metering dial 820, such as notches 842, FIG. 15*b* to facilitate proper orientation with respect to the selected concentration. In order to allow inward deformation of the ratcheting member 886, the actuator body 924 can include a recess or indentation 980. This recess 980 can be configured such that the ratcheting member 886 is allowed to inwardly deform only in the first and third positions whereas the ratcheting member 886 is restricted from deforming inwardly while in the second position. This can provide a means of reducing the likelihood that the plunger body 860 can be rotated during operation of the device.

Embodiment of Pressurized Chamber

Figure 24:
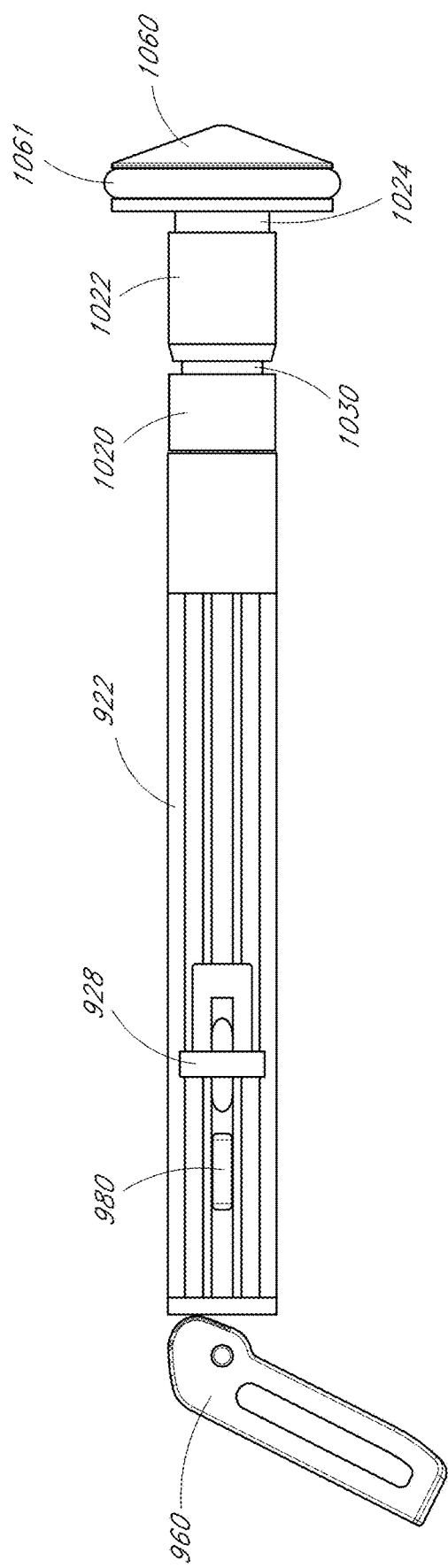
FIG. 24 is an enlarged view of an embodiment of an activation system, pressurized chamber, and a storage member pressure regulation system.

With reference to FIGS. 24-25B, an embodiment of a pressurized chamber is shown along with components of an activation system. As illustrated, the pressurized chamber can have a two-part housing with a first housing member 1020 and a second housing member 1022 which are translatable with respect to each other. As shown in the illustrated embodiment, the two members 1020, 1022 can have a generally cylindrical shape such that some or all portions of the two members 1020, 1022 can be received within a channel 868 of the plunger body 860. In some embodiments, the two members 1020, 1022 can be detached from one another to allow free translation of the two members 1020, 1022. In other embodiments, the two-part housing can be attached while still allowing translation of the members 1020, 1022 with respect to each other. Such attachment can be used to increase the stability of the two members 1020, 1022.

As shown in the illustrated embodiment and similar to other embodiments of the pressurized chamber, an annular slot 1024 can be located on the second housing member 1022. In the illustrated embodiment, the annular slot 1024 is located at an end opposite the first housing member 1020 however other possible locations can be chosen. The annular slot 1024 can be sized and configured to receive the retention wings 870 FIG. 25A of the plunger body 860 allowing the second housing member 1022 to be fastened to the plunger body 860 using a snap-fit connection. To facilitate insertion of the second housing member 1022 into the channel 868 of the plunger body 860, the inserted end portion can be slightly tapered. In some embodiments, the second housing member 1022 can be removably attached to the plunger body 860 thereby allowing replacement of certain parts contained therein. For example, in some embodiments, a storage member 1030 or canister can be contained within the two-part housing. The two-part housing can also have a plunger end 1060 with a plunger seal 1061 such as a rubber O-ring configured to sealingly contact the syringe body 1120 and form a seal for defining a chamber to contain an injectable volume, such chamber potentially serving as a mixing chamber. Other types of sealing members can be used around the plunger end 1060 to form such a seal.

FIGS. 25A and 25B are cross-sectional views of the embodiment shown in FIG. 24 when the apparatus is in a first, "initial", or "pre-activation" position. As illustrated more clearly in FIG. 25B, in the first position, the rod biasing member 924, such as a helical spring, can be in contact with both the actuator body 922 and the first housing member 1020; however, the actuator body 922 may not be in direct contact with the first housing member 1020. In the first position, the rod biasing member 924 can exert a force in a frontward direction upon the first housing member 1020 and a force in a rearward direction upon the actuator body 922 such that the actuator body 922 remains in contact with the activation switch 960. In this position, the frontward force upon the first housing member 1020 can cause the first housing member 1020 to apply a force upon a storage member 1030 contained therein as the first housing member 1020 attempts to translate towards the second housing member 1022. Preferably, in the first position, the force applied by the first housing member 1020 upon the storage member 1030 will be insufficient to translate the storage member 1030 towards the second housing member 1022 due to mechanisms contained in the storage member 1030 (as will be discussed in further detail in FIGS. 28-29). As such, while in the first position, any gas or fluid contained within the storage member 1030 will remain contained within the storage member 1030.

Figure 26A:
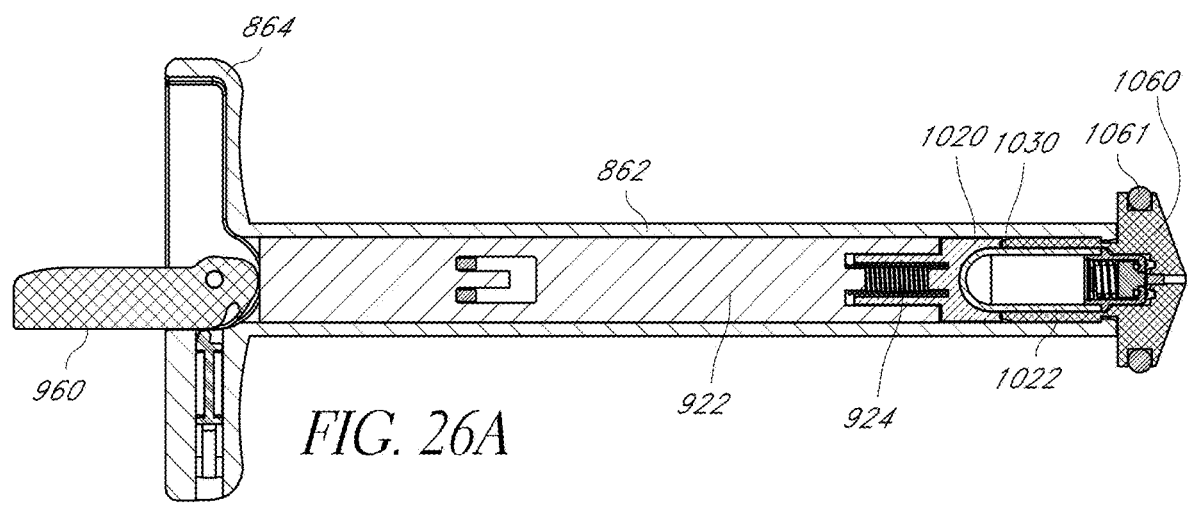
FIG. 26A is a sectional view of the embodiment of an activation system, pressurized chamber, and a storage member pressure regulation system of FIG. 24 in a second or "open" position.
Figure 26B:
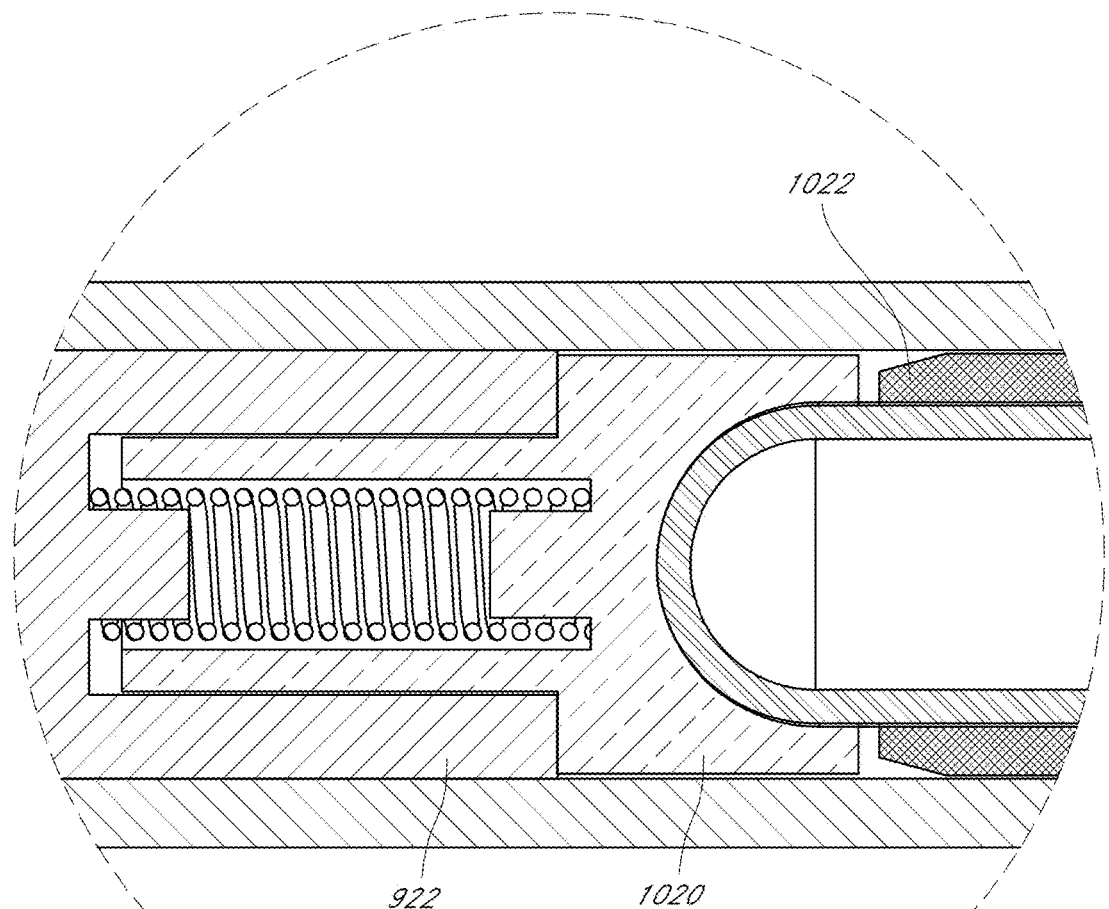
FIG. 26B is an enlarged view of the embodiment of an activation system, pressurized chamber, and a storage member pressure regulation system of FIG. 26A.

FIGS. 26A and 26B are cross-sectional views of the embodiment shown in FIG. 24 when the apparatus is in a second or "open" position. As illustrated more clearly in FIG. 26B, while in the second position, both the actuator body 922 and the rod biasing member 924 can be directly in contact with the first housing member 1020. Due to this direct contact, a more significant force can be applied to the first housing member 1020 such that the first housing member 1020 can translate in a frontward direction thereby causing the storage member 1030 to translate in a frontward direction. This frontward translation of the storage member 1030 can then activate the release of gas from the storage member 1030. In other embodiments, the actuator body 922 need not directly contact the first housing member 1020 since, in such embodiments, the increase in force applied by the rod biasing member 924 due to compression of the rod biasing member 924 can be sufficient to cause the first housing member 1020 to translate in a frontward direction to cause the activation of the release of gas from the storage member 1030.

Figure 27A:
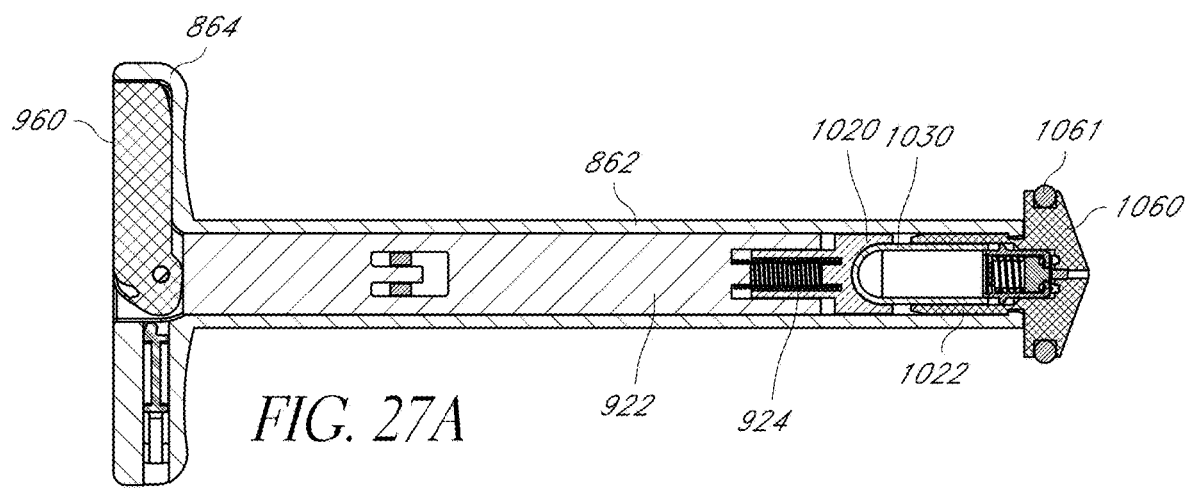
FIG. 27A is a sectional view of the embodiment of an activation system, pressurized chamber, and a storage member pressure regulation system of FIG. 24 in a third or "closed" position.
Figure 27B:
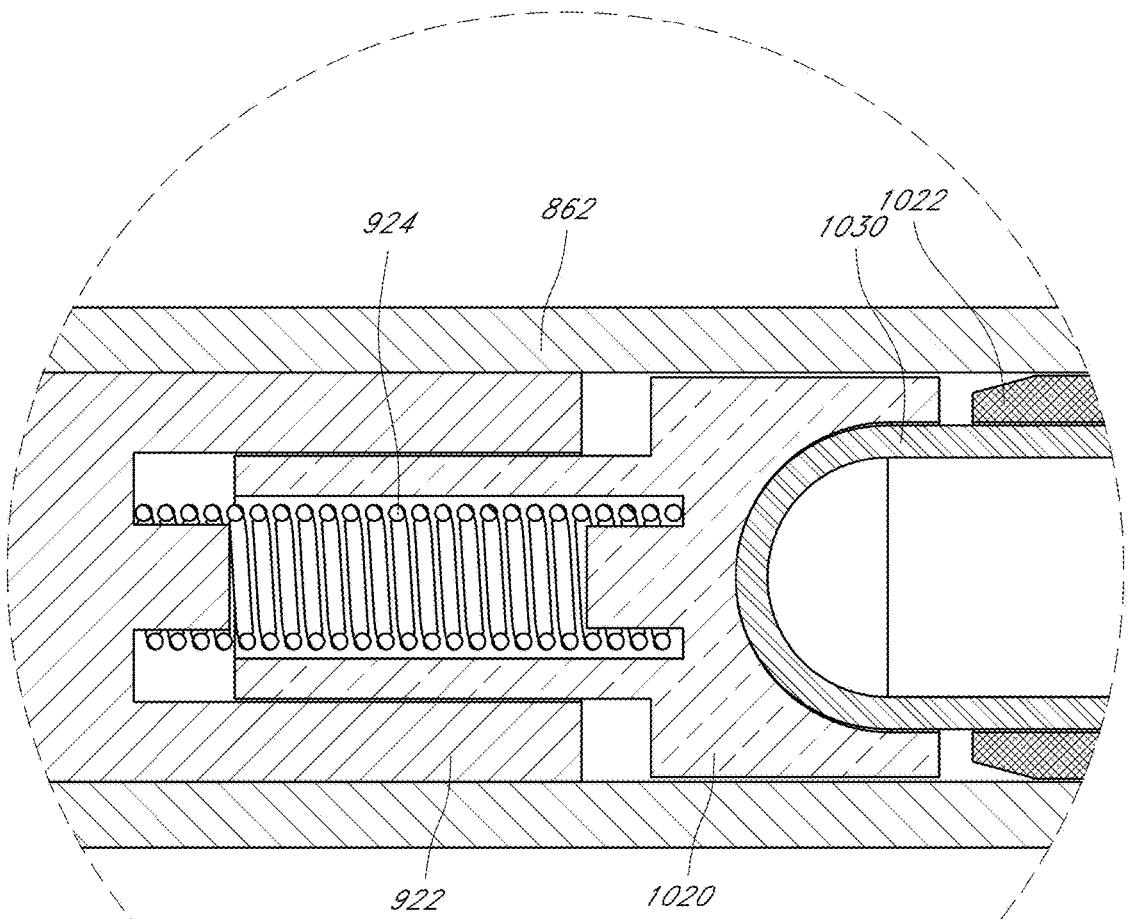
FIG. 27B is an enlarged view of the embodiment of an activation system, pressurized chamber, and a storage member pressure regulation system of FIG. 27A.

FIGS. 27A and 27B are cross-sectional views of the second embodiment shown in FIG. 24 when the apparatus is in a third or "closed" position. As illustrated in FIG. 27B, while in the third position, the actuator body 922 is in contact with the first housing member 1020. Furthermore, in some embodiments, due to the reduced distance between the pin 966 and the contoured surface 962, the force exerted by the rod biasing member 924 on the actuator body 922 in a rearward direction can cause the actuator body 922 to translate towards the contoured surface 962 such that the actuator body 922 remains in contact with the activation switch 960. This expansion of the rod biasing member 924 results in a reduction of force exerted by the rod biasing member 924 upon the first housing member 1020. As a result of this reduced force, and as a result of other mechanisms located within the storage member 1030 or canister, the storage member 1030 can be restored to a closed state thereby preventing any additional gas from being released into the chamber to contain the injectable volume, which can also serve as a mixing chamber.

Figure 28:
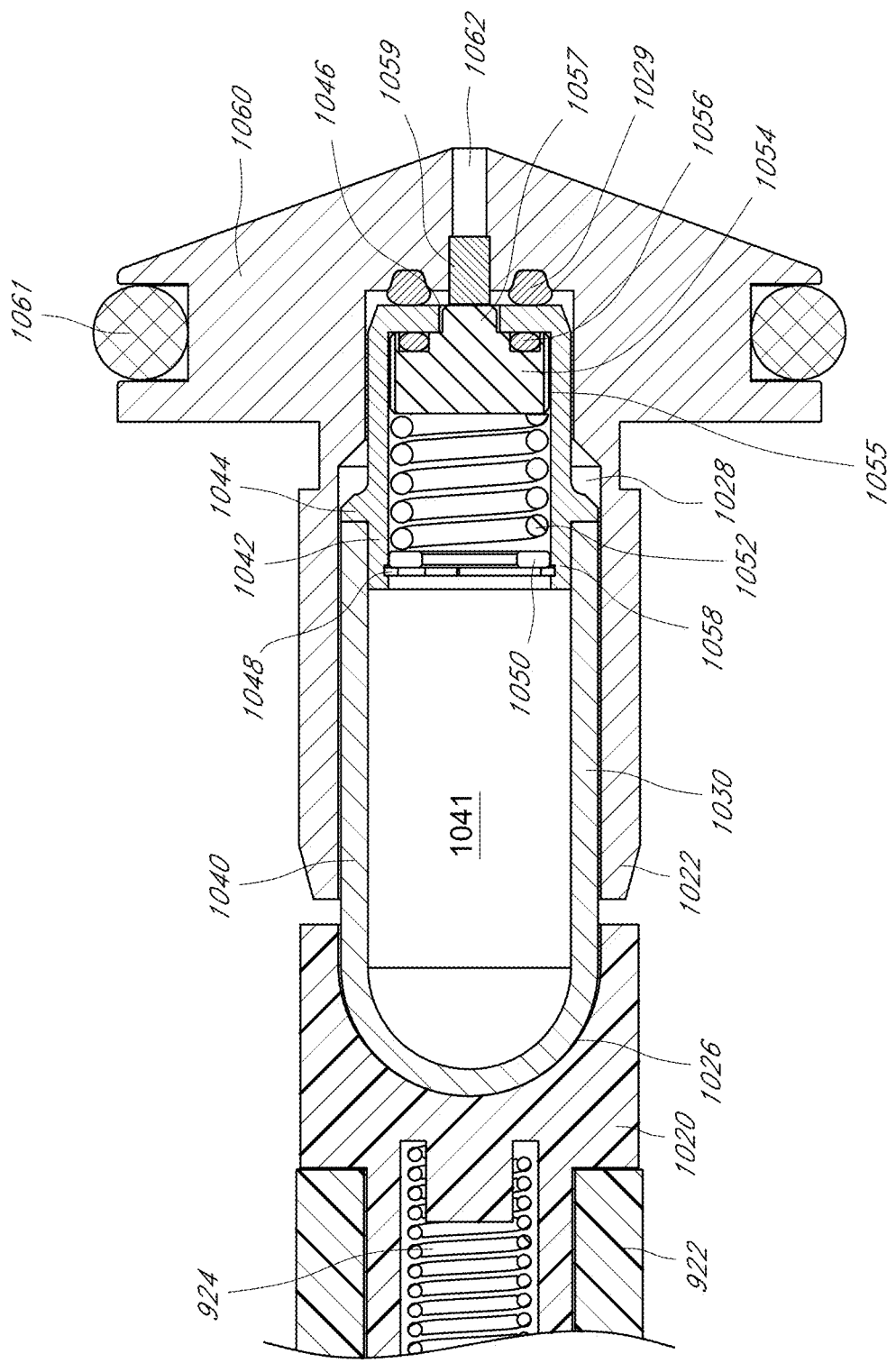
FIG. 28 is an enlarged view of the embodiment of an activation system, pressurized chamber, and a storage member pressure regulation system of FIG. 25A illustrating in more detail an embodiment of a storage member.

FIG. 28 is a sectional view of an embodiment of a pressurized chamber. The first and second housing members 1020, 1022 have contained therein a storage member 1030 or canister, such as a microcylinder, which contains a fluid such as gas. In some embodiments, the second member 1022 has at an end opposite the first member 1020 a conical or frusto-conical surface forming the plunger end 1060. In some embodiments, the second member 1022 and the plunger end 1060 form an integral unit. The plunger end 1060 can have an annular slot configured to receive a plunger seal 1061 such as a rubber O-ring to form a chamber for the injectable volume, which can also serve as a mixing chamber.

The first housing member 1020 can include a recessed portion 1026 or indented portion configured to contact and receive a first end of the storage member 1030. The shape of the recessed portion 1026 should preferably correspond to the shape of the first end of the storage member 1030. In other embodiments, the first housing member 1020 may not include a recessed portion 1026. The second housing member 1022 can include an interior space 1028 sized and configured to receive a second end of the storage member 1030. In some embodiments, the interior space 1028 can include a housing seal 1029 in contact with the second end of the storage member 1030. In some embodiments, the housing seal 1029 creates a sufficient seal such that little to no gas leaks rearward through the interior space 1028. In some embodiments, the interior space 1028 can also provide a generally snug fit around the storage member 1030 to ensure that the storage member 1030 generally only translates in a frontward and rearward direction. This advantageously reduces the likelihood of the seal between the second end of the storage member 1030 and the housing seal 1029 from being broken.

With continued reference to FIG. 28, the storage member 1030, such as the illustrated canister or microcylinder, can include a body portion 1040 and a head 1042. As shown in the illustrated embodiment, the body portion 1040 can have a generally cylindrical shape with a semi-spherical first end. The body portion 1040, in conjunction with the head 1042, can form an internal volume 1041 to contain a fluid such as a gas in either gaseous or liquid form, or a combination of both, at a first pressure and concentration which can be different than atmospheric gas. For example, such gases can include, but are not limited to, expansile gases, ophthalmic gases such as $SF_6$, $C_3F_8$, $C_2F_6$, or similar gases, propellant gases such as $CO_2$, refrigerant gases such as $N_2O$, and other various types of gases. The size of the interior space 1041 can be chosen such that a unit or single-use dose can be contained within the volume. Other shapes can be chosen for the body portion 1040.

The head 1042 can have a generally tubular shape with an outer diameter matching the inner diameter of the body portion 1040. The head 1042 can have an internal channel and a flange 1044. As shown in the illustrated embodiment, the first end of the head 1042 can have an opening with a diameter that matches the diameter of the channel and the second end of the head can have an opening 1046 with a diameter that is less than the diameter of the channel. In some embodiments, the body portion 1040 and the head 1042 can be separate components which are later attached. This potentially advantageously allows for the assembly of internal components of the head 1042 prior to assembly. Once all components are assembled within the head 1042, the head 1042 can be received within the body portion 1040 and fastened using devices and mechanisms such as adhesives, welding, or the like. In some embodiments, such as that illustrated in FIG. 28, the flange 1044 can abut the body portion 1040 and adhered or welded along this surface. In other embodiments, the body portion 1040 and head 1042 can form an integral unit.

The head 1042 can contain a storage member pressure regulation system, which can form part of a first pressure regulation system, and which can take the form of an internal valve mechanism within the channel. The internal valve mechanism can include a retaining ring 1048, a valve seat 1050, an internal biasing member or mechanism 1052 such as a spring, a valve piston 1054, and a piston seal 1056. The retaining ring 1048 can be placed within an annular slot 1058 located on the head 1042. The retaining ring 1048 can be made of an elastic material such that the retaining ring can be deformed prior to fitting into slot 1058. The valve seat 1050 can be placed between the retaining ring 1048 and the second end of the head 1042. In some embodiments, the valve seat 1050 can be a ring having an outer diameter approximately equal to the internal diameter of the head 1042.

The valve piston 1054 can have a generally cylindrical shape and be placed between the seat 1050 and the second end of the head 1042. The outer diameter of the valve piston 1054 can be chosen to be approximately equal to the internal diameter of the head 1042. As shown in the illustrated embodiment, the valve piston can include an annular slot configured to receive the piston seal 1056, fluid pathways 1055 or channels located along the perimeter of the piston, and a protrusion 1057. The fluid pathways 1055 can be configured to allow fluid to pass between the valve piston 1054 and the head 1042. In the illustrated embodiment, a total of four fluid pathways are included; however, fewer or greater numbers of pathways can be used. In some embodiments, the protrusion 1057 can be a cylindrical member having a smaller diameter that corresponds to the diameter of the opening 1046. The protrusion 1057 can be configured to fit within the opening 1046. In some embodiments, the protrusion 1057 can be flush with the end surface of the head 1042. In other embodiments, the protrusion 1057 can be recessed within the opening or extend beyond the end surface. A biasing mechanism 1052 can be placed between the seat 1050 and the piston 1054 to apply a force on the valve piston 1054 in a frontward direction such that a seal is formed between the piston seal 1056 and the head 1042. In other embodiments, other types of valve designs can be used such as a ball valve, poppet valve, or any other valve mentioned herein or known in the art.

In some embodiments, the internal biasing mechanism 1052 can be configured such that, when an activation switch is in a first or "pre-activation" position, the internal valve mechanism will not open as a result of any forces applied to it such as the force applied to the storage member 1030 via the first housing member 1020 as a result of the rod biasing mechanism 924. In some embodiments, the internal biasing mechanism 1052 can be configured such that, when an activation switch is in a second or "open" position, the internal valve mechanism will open as a result of forces applied to it. In some embodiments, the internal biasing mechanism 1052 can be configured such that, when an activation switch is in a third or "closed" position, the internal valve mechanism will not open as a result of any forces applied to it such as the force applied to the storage member 1030 via the first housing member 1020 as a result of the rod biasing mechanism 924.

In some embodiments, the storage member 1030 can include other structures such as filters integrated in portions of the storage member 1030 such as the head 1042. The storage member 1030 can include membranes or other sealing structures placed over the head 1042 and over the opening 1046 to provide an additional seal which can advantageously extend the shelf life of the storage member 1030. The membrane or sealing structure can be punctured by a protruding member, such as a pin 1059, or any other similar release mechanism. In some embodiments, the release mechanism can be a porous material, for example, known as "frit". The storage member 1030 can also include additional valve members which can serve as a relief valve to reduce the likelihood of rupturing if the pressure contained within the storage member 1030 exceeds certain operational limits. The storage member 1030 can also be configured to rupture in a controlled manner to reduce the likelihood of catastrophic failure.

In some embodiments, the storage member 1030, and the internal components such as the internal valve, is manufactured from materials that are both small and light-weight. The material can also be flexible. In some embodiments, the materials and dimensions of the storage member 1030 can be chosen such that the storage member 1030 resists diffusion of gas through the walls of the storage member 1030. This can provide the advantage of increasing storage life of the storage member 1030 when a gas is contained therein. In some embodiments, the length of the storage member 1030 from a rearward most end of the body 1040 and a frontward most end of the head 1042 can range from approximately 15 mm to approximately 65 mm, from approximately 20 mm to approximately 45 mm, and from approximately 25 mm to approximately 35 mm, such as 29 mm. In some embodiments, the outer diameter of the body 1040 can range from approximately 4 mm to approximately 25 mm, from approximately 6 mm to approximately 20 mm, and from approximately 8 mm to approximately 15 mm, such as 9.5 mm. In some embodiments, the outer diameter of the head 1042, not including a flange portion can range from approximately 2 mm to approximately 20 mm, from approximately 4 mm to approximately 15 mm, and from approximately 6 mm to approximately 10 mm, such as 7.5 mm.

Figure 29:
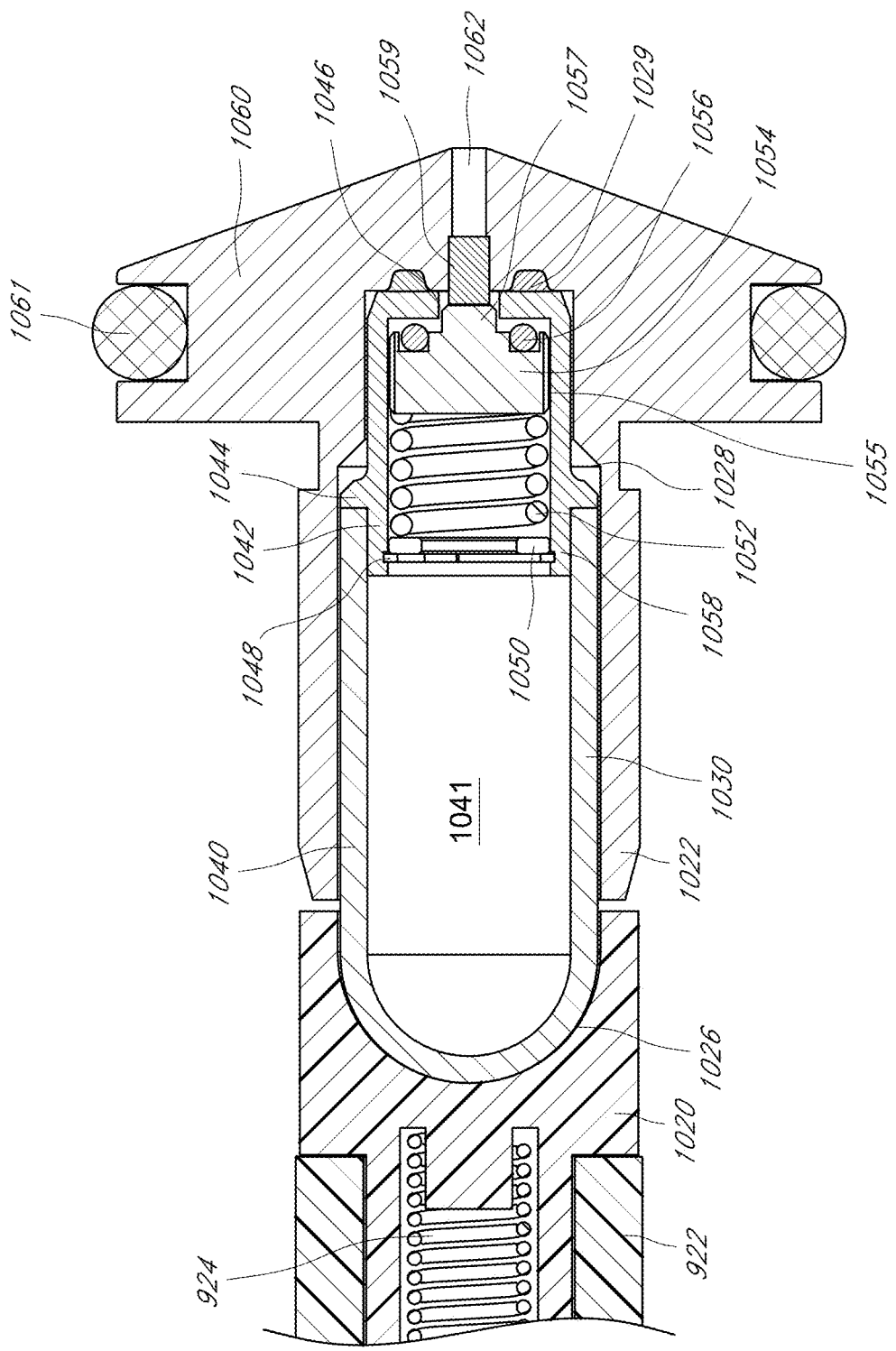
FIG. 29 is an enlarged view of the embodiment of an activation system, pressurized chamber, and a storage member pressure regulation system of FIG. 26A illustrating in more detail an embodiment of a storage member.

With continued reference to FIG. 28, the pin 1059 which can serve as a release mechanism, can be located within a channel 1062. The release mechanism 1059 can be substantially centered over the protrusion 1057 of the valve piston 1054 and have a diameter which matches the diameter of the opening 1046 and can define through passages (not shown). As illustrated in FIG. 29, during operation, when the storage member 1030 is translated in a frontward direction towards the release mechanism 1059, the release mechanism 1059 remains stationary such that the release mechanism 1059 can cause the valve piston 1056 to unseat from the head 1042 thereby allowing the flow of fluid from the storage member 1030, past the pathways 1055 and the release mechanism 1059, and through the channel 1062 where it ultimately can flow into a chamber for the injectable volume, such as a mixing chamber. In some embodiments, the release mechanism 1059 can include internal or external channels or can be made out of a porous material such that the release mechanism 1059 itself serves as a preliminary filtering mechanism for fluid flowing through channel 1062. In some embodiments, filters can be added between the release mechanism 1059 and the end of the channel 1062 or at any other location to filter out materials.

Figure 30:
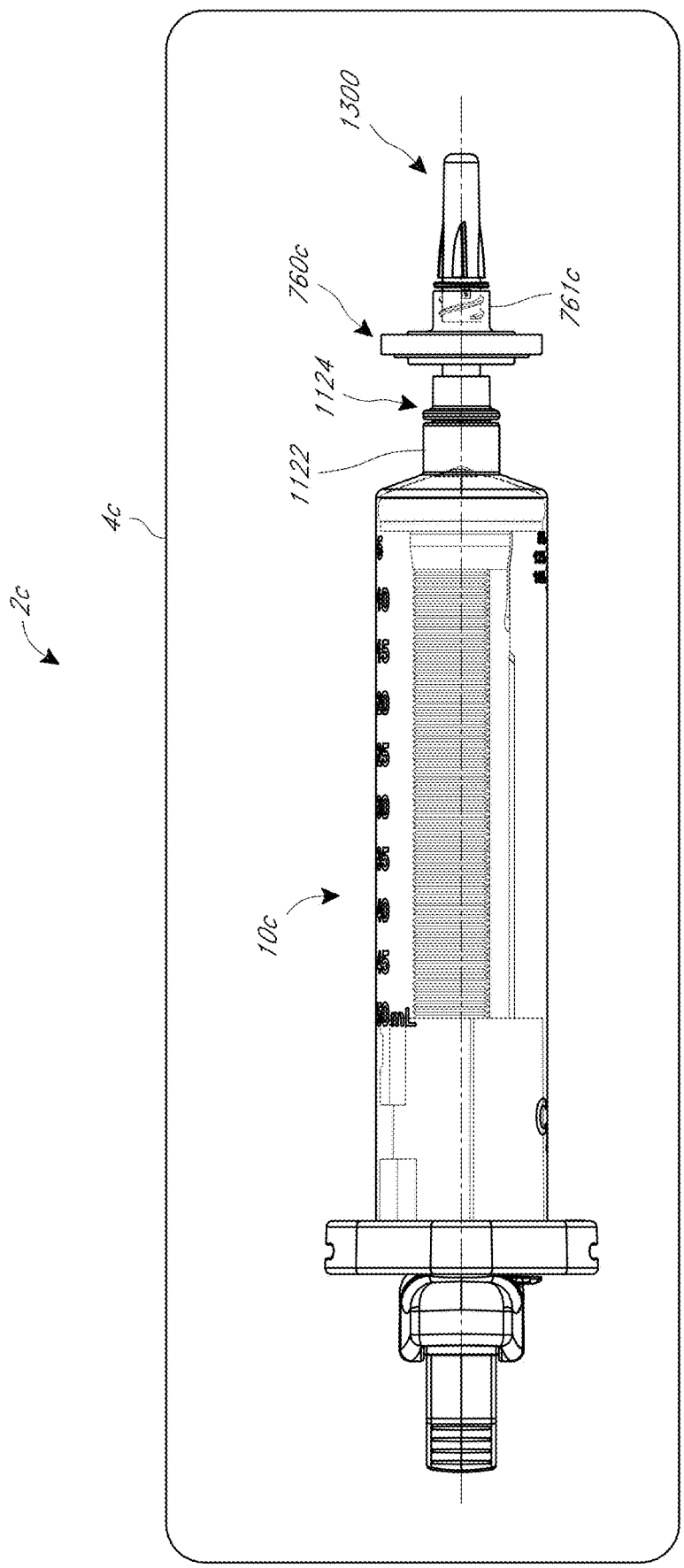
FIG. 30 is a schematic side elevational view of yet another embodiment of a hand-held gaseous injector assembly, removed from a package and prepared for the introduction of a therapeutic gas or gas component into a mixing chamber and including a flow restrictor connected downstream from a filter device.
Figure 31:
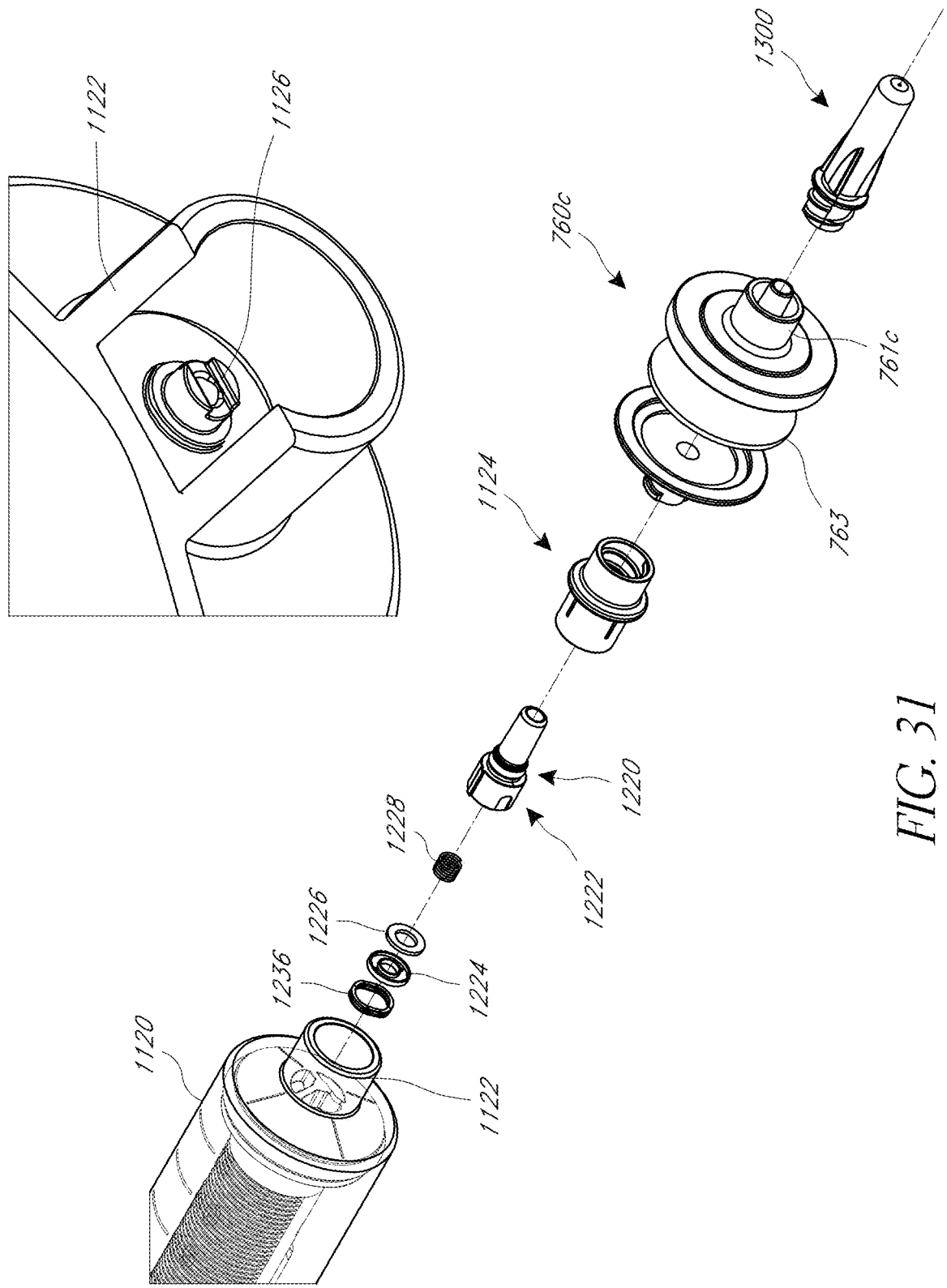
FIG. 31 is an exploded view of the hand-held gaseous injector device of FIG. 30.
Figure 32:
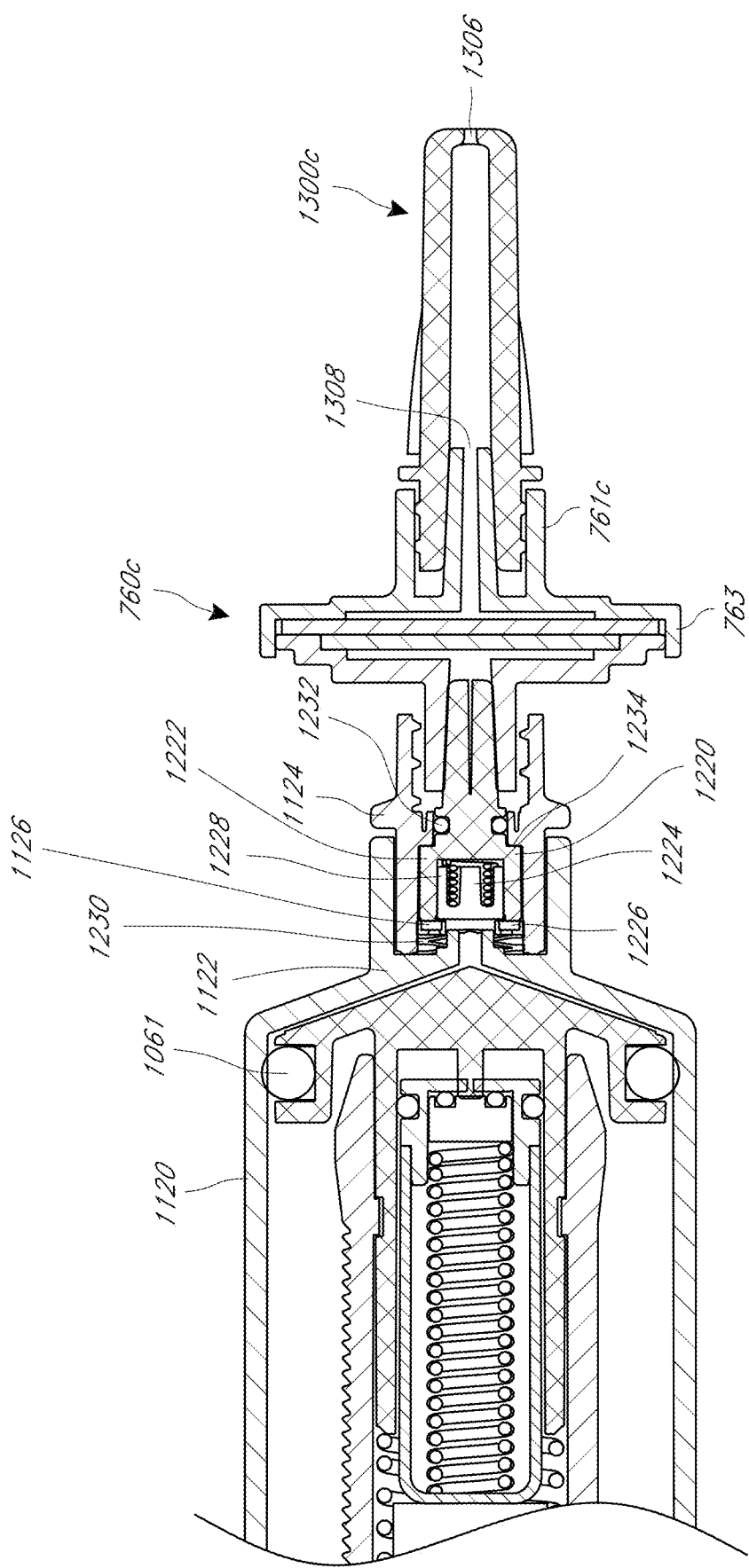
FIG. 32 is a sectional view of an enlarged portion of the injector assembly of FIG. 30.
Figure 35:
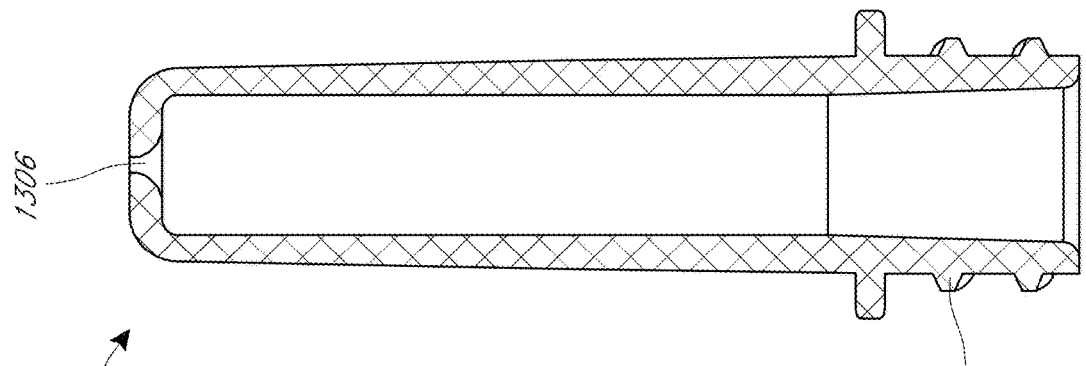
FIG. 35 is an enlarged cross-sectional view of the flow restrictor of FIG. 30.
Figure 34:
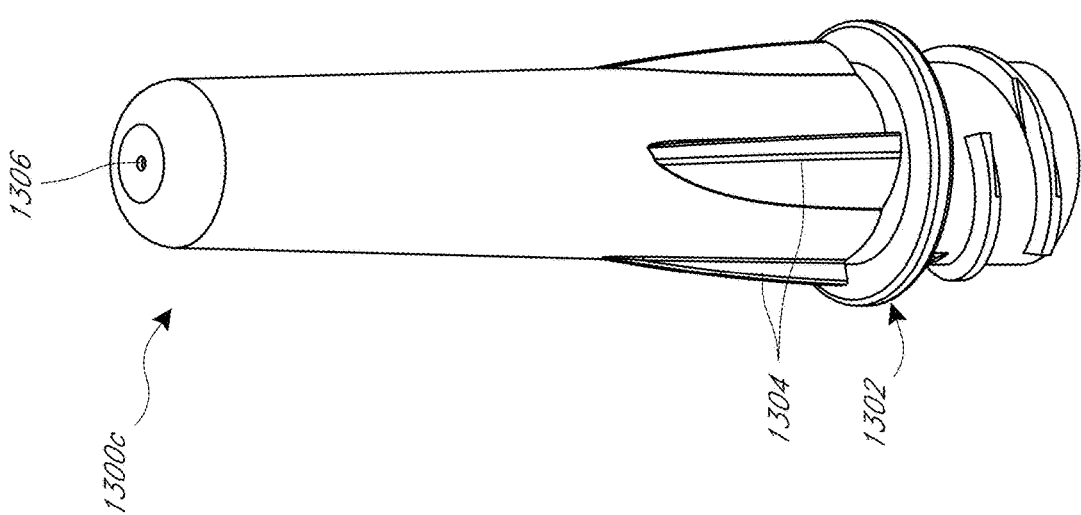
FIG. 34 is an enlarged perspective view of the flow restrictor of FIG. 30.
Figure 33:
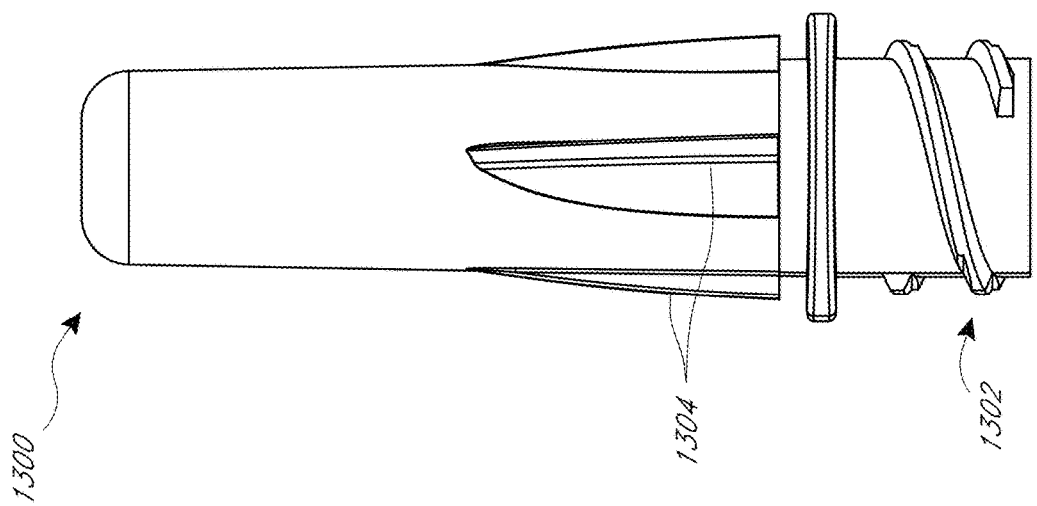
FIG. 33 is an enlarged side elevational view of a flow restrictor of the embodiment of FIG. 30.

With reference to FIGS. 30-32, a further embodiment of a surgical kit 2c is illustrated as including a container 4c with a gas mixing device 10c. The gas mixing device 10c can include the same or similar components described above with reference to gas mixing devices 10, 10a, and 10b, except as noted below.

The mixing device 10c can include a chamber for an injectable volume, such as a mixing chamber, which can include a syringe body 1120, a syringe pressure regulation system, which can form part of a second pressure regulation system, and various components of the above-mentioned systems. Syringe body 1120 can have a cylindrical body and a nose 1122 at a front end.

In some embodiments, a threaded nozzle 1124, which can include multiple components of a pressure regulation system, can be removably attached to the nose 1122 of the syringe body 1120. This can advantageously facilitate assembly of the apparatus by allowing the pressure regulation system to be assembled within the smaller nozzle 1124 prior to being incorporated with the syringe body 1120. The nozzle 1124 can be attached to the nose 1122 using multiple fastening devices and means such as screws, adhesives, snap fits, welding, or the like. The chamber for an injectable volume can be defined by the inner walls of the syringe body 1120 and the plunger seal 1061. Furthermore, as with other embodiments of the syringe, the syringe body 1120 can also include indicators along its outer surface corresponding to a chosen concentration and a flange at a rear end of the body 1120 configured to be attached to a metering dial. Optionally, the surgical kit 2c can include a flow restrictor 1300 connected to the 761c of the filter device 760c.

With continued reference to FIGS. 30-32, an embodiment of the syringe pressure regulation system is shown comprising a valve body 1220, a valve end 1222, a valve piston 1224, a piston seal 1226, a piston biasing member or mechanism 1228, a valve biasing member or mechanism 1230, and a valve end seal 1232. Similar to other embodiments of the pressure regulation system, the valve body 1220 and valve end 1222 can slidingly translate within the threaded nozzle 1124.

In a first position, such as that illustrated in FIG. 32, the valve end 1222 can rest against a shoulder 1234 of the threaded nozzle 1124 due to force exerted by the valve biasing member 1230 on the valve body 1220 and valve end 1222 in a frontward direction. In the first position, the valve piston 1224 and valve seal 1226 can form a seal and limit, or prevent, the passage of fluid through the valve body 1220. However, when the pressure in the chamber for an injectable volume increases beyond a threshold value to overcome the biasing force exerted by the piston biasing member 1228, the valve piston 1224 can be translated in a frontward direction against the force applied by the piston biasing member 1228 and fluid can pass through the valve body 1220 and valve end 1222 and into the atmosphere. Once the pressure reduces back to a threshold value, the equilibrium of forces allows the valve piston 1224 and valve seal 1226 to once again sealingly contact the valve body 1220.

In a second position, the valve body 1220 and valve end 1222 can be translated in a rearward direction against the valve biasing member 1230. For example, this can be accomplished by applying a force in the rearward direction upon the valve end 1222. In the second position, contact between the valve piston 1224 and an internal protruding member 1126 of the syringe body 1120 can cause the valve piston 1224 to move in a rearward direction relative to the valve body 1220 and valve end 1222 such that the valve piston 1224 no longer sealingly contacts the valve body 1220. This could, in some embodiments, allow the passage of fluid to and from the chamber for an injectable volume.

In some embodiments, the pressure regulation system can be forced into a second position when an inline filter 760c is threaded onto the threaded nozzle 1124. Other types of attachments, such as stopcocks, valves, tubing, or the like, can also be attached to the threaded nozzle 1124.

With reference to FIGS. 32-35, the flow restrictor 1300c can be in the form of a cap configured to engage the outlet and 761c of the filter device 760c. For example, the flow restrictor 1300c can include a threaded end 1302 configured to engage threads on an inner surface of the outlet 761c. Additionally, the flow restrictor 1300c can include optional finger grips 1304 configured to facilitate gripping with fingers so as to ease removal of the flow restrictor 1300c when wearing surgical gloves.

The flow restrictor can also include a flow restricting port 1306. In some embodiments, a minimum diameter of the port 1306 can be smaller than the smallest diameter of an outlet opening 1308 of the outlet 761c (FIG. 30). Thus, a minimum cross-sectional area of the outlet port 1306 can be smaller than a minimum cross-sectional area of the outlet opening 1308. As such, as described above with reference to FIG. 1A and the flow restrictor 1300c. With continued reference to FIG. 30, an operating, the mixing device 10c can be packaged in container 4c forming the surgical kit 2c. As with the other mixing devices 10, 10a, 10 and 10b, the mixing device 10c can be packaged in the container 4c with the filter device 760c preattached in a sterilized condition and optionally can also include the flow restrictor 1300.

In use, a practitioner or other user can remove the mixing device 10c from the package 4c having the filter 760c preattached. The user can then provide a therapeutic gas and/or component thereof into the mixing chamber of the device 10c which would move the plunger 1061 in a direction away from the filter device 760c (as viewed in FIG. 30) until the plunger 1061 has been moved to a position corresponding to the desired volume of therapeutic gas which would provide a desired mixed gas concentration. After the plunger 1061 has been moved to the desired position, excess therapeutic gas can be discharged through the filter device 760c. As such, because the filter device 760c is preattached to the mixing device 10c, at no time will any unfiltered atmospheric air reside in any open volumes between the filter member 763 of the filter device 760c and the plunger 1061. Thus, during discharge of the therapeutic gas through this filter device 760c, no contaminants, foreign matter, or undesirable gases will be captured on the upstream side of the filter member 763.

After the desired volume of therapeutic gas or a component thereof is contained in the mixing chamber, a user can manually further move the plunger 1061 in a direction away from the filter device 760c and thereby draw atmospheric air in through the outlet 761c of the filter device 760c, through the filter member 763, and into the mixing chamber. As such, the filter member 763 can filter out any particulates, foreign matter, or undesirable gases and prevent such from entering the mixing chamber. After the mixing chamber is expanded to the desired volume and thereby forming a desired concentration of a therapeutic mixture, the filter device 760c can be removed and a further delivery device can be connected in its place. For example, a hypodermic needle can be attached in place of the filter device 760c for delivery of a therapeutic gas.

As noted above, the mixing device 10c can optionally be packaged in the container 4c with the flow restrictor 1300c preattached. Having the flow restrictor 1300c preattached provides an optional additional benefit of providing additional back pressure during discharge of excess gas which can thereby help ensure the plunger 1061 is pushed fully against any limiting device for defining a predetermined volume of therapeutic gas or a component of therapeutic gas within the syringe body 1120.

In some embodiments, the pressurized chamber can be external to the apparatus. In such embodiments, the pressurized chamber can be a tank or other canister containing the gas in liquid or gaseous (or a combination) form. In some embodiments, the tank can be attached to the threaded nozzle via tubing or other mechanisms. The connection between the threaded nozzle and tubing can cause the pressure regulation system located on the apparatus to be forced open thereby allowing the gas from the tank to be input into the chamber. In some embodiments, introduction of the gas from the tank can be performed during a first phase of operation. As such, the gas from the tank can fill the apparatus with gas until the apparatus reaches a configured first volume. In some embodiments, the tank can have a regulator such that the apparatus is filled with gas at a regulated pressure. The connection can then be removed from the threaded nozzle, allowing the valve to function normally. In some embodiments, since the gas can be at a higher pressure than atmospheric air and can exceed a threshold value for the pressure regulation system, the gas can be expelled or bled from the system until a configured pressure is achieved in the apparatus. Once the configured pressure is achieved in the apparatus, the remaining phases of operation can then be completed in a similar manner to those in the above-described embodiments.

The foregoing description is that of an apparatus and method for mixing and/or injecting gases having certain features, aspects, and advantages in accordance with the present inventions. Various changes and modifications also can be made to the above-described gas mixture apparatus and method without departing from the spirit and scope of the inventions. Thus, for example, those skilled in the art will recognize that the invention can be embodied or carried out in a manner that achieves or optimizes one advantage or group of advantages as taught herein without necessarily achieving other objects or advantages as can be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of the specific features and aspects of the embodiments can be made and still fall within the scope of the invention. Accordingly, it should be understood that various features and aspects of the disclosed embodiments can be combined with or substituted for one another in order to form varying modes of the disclosed gas mixture apparatus.

What is claimed is:

1. A hand-held gaseous injector assembly for delivering therapeutic gas to a patient, comprising:
   a syringe body with an outlet;
   a plunger slidably disposed in the syringe body and with the syringe body, defining a first chamber within the syringe body;
   a second chamber disposed within at least one of the syringe body and the plunger, the second chamber comprising:
      an internal volume containing at least a first fluid in a concentration different than that in atmospheric air and at a pressure greater than that of the surrounding atmospheric air;

an opening at a first end of the second chamber; and a valve mechanism located adjacent the first end, the valve mechanism configured to seal the opening;

a channel and an aperture between the second chamber and the first chamber;

an activation system operatively coupled to the second chamber, the activation system being configured to cause a release of the first fluid from the second chamber into the first chamber through the channel;

an adjustable volume limiter configured to limit movement of the plunger to a plurality of user-selectable positions corresponding to a plurality of volumes of the first chamber;

a filter having a first end connected to the outlet of the syringe body, a second end with a filter orifice, and a filter element disposed between the first end and the second end; and a flow restrictor removably connected to the filter orifice and having a restrictor orifice that is smaller than the filter orifice and configured to restrict a flow of fluid from the first chamber through the filter orifice such that the first fluid from the second chamber travels from the second chamber, through the valve mechanism located adjacent the first end of the second chamber, through the first chamber, through the first end of the filter, through the filter, through the second end of the filter with the filter orifice and then through the restrictor orifice of the flow restrictor to an exterior of the hand-held gaseous injector assembly;

wherein the removable flow restrictor is configured to generate back pressure against the flow of fluid from the first chamber to expand the first chamber to a desired volume corresponding to a user-selected position of the adjustable volume limiter;

wherein the flow restrictor is removable, after expansion of the first chamber to the desired volume corresponding to the user-selected position, to allow a less restricted flow of atmospheric air from the exterior of the hand-held gaseous injector assembly, through the filter element, and into the first chamber for mixing of the fluid from the second chamber and the atmospheric air in the first chamber.

2. The hand-held gaseous injector assembly of claim 1, wherein the filter is removably connected to the syringe body.

3. The hand-held gaseous injector assembly of claim 1, wherein the flow restrictor comprises a lumen having a first end configured to receive fluid from the filter orifice and a second end comprising the restrictor orifice, wherein the lumen tapers between the first end and the second end.

4. The hand-held gaseous injector assembly of claim 1, wherein the flow restrictor is a cap configured to removably engage an outlet of the filter.

5. A hand-held gaseous injector assembly, comprising:
a syringe body with an outlet;
a plunger slidably disposed in the syringe body and with the syringe body, defining a chamber within the syringe body;
an adjustable volume limiter configured to limit movement of the plunger to a plurality of user-selectable positions corresponding to a plurality of volumes of the chamber;
a filter having a first end connected to the outlet of the syringe body and a second end with a filter orifice; and a flow restrictor removably connected to the filter orifice and having a restrictor orifice that is smaller than the filter orifice and configured to restrict a flow of fluid from the chamber through the filter orifice such that a fluid leaving the syringe, travels through the first end of the filter, through the filter, through the second end of the filter with the filter orifice and then through the restrictor orifice of the flow restrictor to an exterior of the hand-held gaseous injector assembly;

wherein the removable flow restrictor is configured to generate back pressure against the flow of fluid from the chamber to expand the chamber to a desired volume corresponding to a user-selected position of the adjustable volume limiter;

wherein the flow restrictor is removable, after expansion of the chamber to the desired volume corresponding to the user-selected position, to allow a less restricted flow of atmospheric air from the exterior of the hand-held gaseous injector assembly, through the filter, and into the chamber for mixing of the fluid and the atmospheric air in the chamber.

6. The hand-held gaseous injector assembly of claim 5, further comprising a filling mechanism configured to direct the fluid into the chamber.

7. The hand-held gaseous injector assembly of claim 5, wherein the filter is removably connected to the syringe body.

8. The hand-held gaseous injector assembly of claim 5, wherein the flow restrictor comprises a lumen having a first end configured to receive the fluid from the filter orifice and a second end comprising the restrictor orifice, wherein the lumen tapers from a larger size at the first end to a smaller size at the second end.

9. The hand-held gaseous injector assembly of claim 5, further comprising a valve mechanism having a first position and a second position, the valve mechanism configured to prohibit flow of the fluid from the chamber when in the first position and to permit flow of the fluid from the chamber when in the second position.

10. The hand-held gaseous injector assembly of claim 5, wherein the flow restrictor is a cap configured to removably engage an outlet of the filter.

11. A hand-held gaseous injector assembly, comprising:
a syringe body comprising an endwall and an outlet connected to the endwall;
a plunger slidably disposed in the syringe body and with the syringe body, defining a first chamber within the syringe body and between the plunger and the endwall, the plunger being disposed at the endwall of the syringe body such that the first chamber comprises a volume definable by movement of the plunger;
a second chamber, the second chamber comprising an internal volume containing at least a first fluid in a concentration different than that in atmospheric air and at a pressure greater than that of the surrounding atmospheric air, wherein the second chamber is fluidically coupled to the first chamber for release of the first fluid from the second chamber to the first chamber;
a filter having a first end connected to the outlet of the syringe and a second end with a filter orifice; and
a flow restrictor removably connected to the filter orifice and configured to restrict a flow of the first fluid from the first chamber through the filter orifice, wherein the flow restrictor comprises a restrictor orifice that is smaller than the filter orifice such that the first fluid leaving the syringe body travels through the first end of the filter, through the filter, through the second end of the filter with the filter orifice and then through the restrictor orifice of the flow restrictor to an exterior of the hand-held gaseous injector assembly;

wherein the removable flow restrictor is configured to generate back pressure against a flow of the first fluid from the first chamber to expand the first chamber to a desired volume corresponding to a user-selected position of an adjustable volume limiter of the hand-held gaseous injector assembly;

wherein the flow restrictor is removable, after expansion of the first chamber to the desired volume corresponding to the user-selected position, to allow a less restricted flow of atmospheric air from the exterior of the hand-held gaseous injector assembly, through the filter, and into the first chamber for mixing of the first fluid from the second chamber and the atmospheric air in the first chamber.

12. The hand-held gaseous injector assembly of claim 11, wherein the adjustable volume limiter is configured to limit movement of the plunger to a plurality of user-selectable positions corresponding to a plurality of volumes of the first chamber.

13. The hand-held gaseous injector assembly of claim 11, wherein the filter is removably connected to the syringe body.

14. The hand-held gaseous injector assembly of claim 11, wherein the flow restrictor comprises a lumen having a first end configured to receive the first fluid from the filter orifice and a second end comprising the restrictor orifice, wherein the lumen tapers between the first end and the second end.

15. The hand-held gaseous injector assembly of claim 11, further comprising a filling mechanism configured to direct the first fluid into the first chamber.

16. The hand-held gaseous injector assembly of claim 15, wherein the second chamber comprises an opening at a first end and an internal valve mechanism located adjacent the first end, the internal valve mechanism configured to seal the opening.

17. The hand-held gaseous injector assembly of claim 16, wherein the internal valve mechanism comprises a piston, a seal, and a biasing member, the internal valve mechanism configured to seal the opening at least prior to activation of the assembly.

18. The hand-held gaseous injector assembly of claim 11, further comprising a valve mechanism configured to move between a first position and a second position, the valve mechanism configured to prohibit flow of the first fluid from the first chamber when in the first position and to permit flow of the first fluid from the first chamber when in the second position.

19. The hand-held gaseous injector assembly of claim 18, wherein the valve mechanism comprises a valve body, a piston, a seal, a valve biasing member, and an internal protruding member.

20. The hand-held gaseous injector assembly of claim 18, wherein the filter is removably connected to the syringe body, the filter being configured to engage the valve mechanism when coupled to the syringe body so as to transition the valve mechanism from the first configuration to the second configuration.

* * * * *